US005733549A

United States Patent [19]
Yamada et al.

[11] Patent Number: 5,733,549
[45] Date of Patent: Mar. 31, 1998

[54] PEPTIDES INCLUDING AMINO ACID SEQUENCES SELECTED FROM LIPOPROTEIN (A) AND APOLIPOPROTEIN (A), ANTIBODIES RECOGNIZING THESE AMINO ACID SEQUENCES, AND METHODS OF DETERMINATION USING THESE ANTIBODIES

[75] Inventors: Shingo Yamada; Keiichi Inoue; Megumi Kitajime; Hajime Yoshimura, all of Sagamihara; Ikunosuke Sakurabayashi, Omiya, all of Japan

[73] Assignee: Shino-Test Corporation, Japan

[21] Appl. No.: 211,747

[22] PCT Filed: Aug. 12, 1993

[86] PCT No.: PCT/JP93/01142

§ 371 Date: Apr. 14, 1994

§ 102(e) Date: Apr. 14, 1994

[87] PCT Pub. No.: WO94/04563

PCT Pub. Date: Mar. 3, 1994

[30] Foreign Application Priority Data

Aug. 14, 1992 [JP] Japan .................................. 4-237621
Nov. 9, 1992 [JP] Japan .................................. 4-322237

[51] Int. Cl.⁶ ........................ A61K 39/00; A61K 39/385; C07K 4/12
[52] U.S. Cl. ........................ 424/185.1; 530/300; 530/327; 530/328; 530/329; 424/569
[58] Field of Search .................. 530/300, 328, 530/327, 329; 424/185.1, 569

[56] References Cited

U.S. PATENT DOCUMENTS

| | | |
|---|---|---|
| 4,839,343 | 6/1989 | Waeber et al. ............................. 514/12 |
| 4,877,746 | 10/1989 | Jansson et al. ........................... 436/518 |
| 4,945,040 | 7/1990 | Fless et al. ............................... 435/7.94 |
| 4,970,144 | 11/1990 | Fareed et al. ............................... 435/5 |
| 5,486,476 | 1/1996 | Burns et al. . |

FOREIGN PATENT DOCUMENTS

| | | |
|---|---|---|
| 327 418 | 8/1989 | European Pat. Off. . |
| 330 506 | 8/1989 | European Pat. Off. . |
| 333 517 | 9/1989 | European Pat. Off. . |
| 506 523 | 9/1992 | European Pat. Off. . |
| 614 912 | 9/1994 | European Pat. Off. . |
| 94 90 8101 | 4/1996 | European Pat. Off. . |
| 06-113880 | 4/1994 | Japan . |
| WO A 8604144 | 7/1986 | WIPO . |
| WO 89/03430 | 4/1989 | WIPO . |
| WO 89/05857 | 6/1989 | WIPO . |
| WO 89/09064 | 10/1989 | WIPO . |
| WO 91/16919 | 11/1991 | WIPO . |
| WO 92/09893 | 6/1992 | WIPO . |
| WO 90/05744 | 5/1994 | WIPO . |

OTHER PUBLICATIONS

Tomlinson et al., The Journal of Biological Chemistry, vol. 264, No. 10, pp. 5957–5965, 1989, "Rhesus Monkey Apolipoprotein (a)".

Chen et al., 1992, "Studies on epitopes on low–density lipoprotein modified by 4–hydroxynonenal", Biochem J 288:249–254.

Trieu et al., 1991, "Interaction of apolipoprotein(a) with apolipoprotein B–containing lipoproteins" J Biol Chem 266(9):5480–5485.

Lafferty et al., 1991, "Immunochemistry of human Lp[a]: Characterization of monoclonal antibodies that cross–react strongly with plasminogen", J Lipid Res 32:277–292.

Wong et al., 1990, "A monoclonal–antibody–based enzyme–linked immunosorbent assay of lipoprotein(a)" Clin Chem 26(2):192–197.

Morrisett et al., 1990, "Structural properties of Apo(a): A major apolipoprotein of human lipoprotein(a)", In: Lipoprotein(a), Scanu et al. (Eds.) Academic Press, Inc. San Diego pp. 53–74.

Menzel et al., 1990, "Abetalipoproteinemia with an apoB–100–lipoprotein(a) glycoprotein complex in plasma", J Biol Chem 265(2):981–986.

Abe et al., 1988, "Enzyme–linked immunoabsorbent assay of lipoprotein(a) in serum and cord blood", Clinica Chimica Acta 177:31–40.

Kraft et al., 1988, "Lp(a) phenotyping by immunoblotting with polyclonal and monoclonal antibodies", Arteriosclerosis 8(3):212–216.

Utermann et al., 1988, "Genetics of the qualitative Lp(a) lipoprotein trait" Hum Genet 78:41–46.

Utermann et al., 1987, "Lp(a) glycoprotein phenotypes", J Clin Invest 80:458–465.

Eaton et al., 1987, "Partial amino acid sequence of apolipoprotein(a) shows that it is homologous to plasminogen", Proc Natl Acad Sci 84:3224–3228.

(List continued on next page.)

*Primary Examiner*—Mary E. Mosher
*Assistant Examiner*—Laurie Scheiner
*Attorney, Agent, or Firm*—Pennie & Edmonds

[57] ABSTRACT

Amino acid sequences having specificity as lipoprotein (a) and low homology with LDL and plasminogen are selected from the amino acid sequence of lipoprotein (a), and antibodies to lipoprotein (a) which recognize these amino acid sequences specifically are obtained. At least one of these antibodies is used in immunological techniques for the determination of lipoprotein (a). Moreover, an amino acid sequence having specificity as apolipoprotein (a) and not having antigenicity as lipoprotein (a) or plasminogen is selected from the amino acid sequence of apolipoprotein (a), and antibodies to apolipoprotein (a) which recognize this amino acid sequence specifically are obtained. At least one of these antibodies is used in immunological techniques for the determination of apolipoprotein (a). As compared with prior art methods, antibodies to lipoprotein (a) and apolipoprotein (a) can be obtained according to a simplified procedure, and their use makes it possible to determine lipoprotein (a) and apolipoprotein (a) accurately.

9 Claims, 23 Drawing Sheets

OTHER PUBLICATIONS

McLean et al., 1987, "cDNA sequence of human apolipoprotein(a) is homologous to plasminogen", Nature 330:132–137.

Fless et al., 1986, "Physicochemical properties of apolipoprotein(a) and lipoprotein(a–) derived from the dissociation of human plasma lipoprotein (a)", J Biol Chem 261(19):8712–8718.

Schriewer et al., 1984, "The relationship of Lipoprotein (a) (Lp(a)) to risk factors of coronary heart disease" J Clin Chem Clin Biochem 22:591–596.

Kostner et al., 1981, "Lipoprotein Lp(a) and the risk for myocardial infarction", Atherosclerosis 38:51–61.

Berg et al., 1979, "Lp(a) phenotypes, other lipoprotein parameters, and a family history of coronary heart disease in middle–aged males", Clin Genet 16:347–352.

Albers et al., 1977, "Radioimmunoassay of human plasma Lp(a) lipoprotein", J Lipid Res 18:331–338.

Dahlén et al., 1972, Acta Med Scand (Suppl.) 531:1–29.

Enholm et al., 1971, "Purification and quantitation of the human plasma lipoprotein carrying the Lp(a) antigen", Biochim Biophys Acta 236:431–439.

Berg, 1963, "A new serum type system in man—The $L_p$ system", Acta Path Microbiol Scand 59:369–382.

Kiyama et al, "Studies on Preparation of Antibodies for Low Molecular Antigen", Synopses of Lectures Given at th 112th Annual Meeting of the Pharmaceutical Society of Japan, 3:122 (1992).

Hopp and Woods, "Prediction of protein antigenic determinants from amino acid sequences", Proceedings fo the National Academy of Sciences, USA 78(6):3824–3828 (1981).

Parker et al., "New Hydrophilicity Scale Derived from High–Performance Liquid Chromatography Peptide Retention Data: Correlation of Predicted Surface Residues with Antigenicity and X–ray–Derived Accessible Sites", Biochemistry 25:5425–5432 (1986).

Garnier, "Analysis of the Accuracy and Implication of Simple Methods for Predicting the Secondary Structure of Globular Proteins", Journal of Molecular Biology 120:97–120 (1978).

Karplus and Schultz, "Prediction of Chain Flexibility of Proteins", Naturwissenschaften 72:212–213 (1985).

Hudecz and Price, "Monoclonal antibody binding to peptide epitopes conjugated to synthetic branched chain polypeptide carriers", Journal of Immunological Methods 147:201–210 (1992).

Guo et al., "Characterization of five mouse monoclonal antibodies to apolipoprotein[a]: evidence for weak plasminogen reactivity", Journal of Lipid Research 30:23–37 (1989).

Kohler and Milstein, "Continuous cultures of fused cells secreting antibody of predefined specificity", Nature 256:495–497 (1975).

| PKNO | TIME | AREA | CONC |
|------|--------|-------|---------|
| 1 | 17.477 | 250 | 0.6306 |
| 2 | 18.643 | 39191 | 99.059 |
| 3 | 19.407 | 123 | 0.3104 |
| TOTAL | | 39563 | 100 |

2   1   N   P

P   N   1   2

B  I

S  P  N

B I

P N 2 3

PEPTIDES INCLUDING AMINO ACID SEQUENCES SELECTED FROM LIPOPROTEIN (A) AND APOLIPOPROTEIN (A), ANTIBODIES RECOGNIZING THESE AMINO ACID SEQUENCES, AND METHODS OF DETERMINATION USING THESE ANTIBODIES

TECHNICAL FIELD

This invention relates to peptides selected from apolipoprotein (a) that is a constituent of lipoprotein (a) being a risk factor involved in arteriosclerosis and having clinical significance, immunogens for producing antibodies which recognize lipoprotein (a) or apolipoprotein (a) or peptides comprising constituent parts thereof, antibodies recognizing lipoprotein (a) or apolipoprotein (a) or peptides comprising constituent parts thereof, and methods for the determination of lipoprotein (a) or apolipoprotein (a) using these antibodies.

BACKGROUND ART

Lipoprotein (a) [Lp(a)] was first reported in 1963 by Berg as a variant of β-lipoprotein [K. Berg, Acta Pathol. Microbiol. Scand., 59, 369–382(1963)]. As a result of subsequent various investigations, it has been found that lipoprotein (a) is a substance consisting of low-density lipoprotein (LDL) which usually plays a major role in transporting cholesterol esters within the living body, and of apolipoprotein (a) [apo (a)] which is a protein peculiar to lipoprotein (a), the protein moiety of LDL (i.e., apolipoprotein B-100) and apolipoprotein (a) being linked to each other by a disulfide bond (see FIG. 36).

Apolipoprotein (a) comprises at most 37 portions having high homology with a structure, called Kringle 4, of plasminogen, a portion having high homology with the Kringle 5 structure of plasminogen, and a serine protease structure portion with a region having high homology with plasminogen. Of these 37 Kringle portions, 28 have a completely repeating structure.

Moreover, it has been reported that various isotypes (phenotypes) of lipoprotein (a) exist [G. Utermann et al., J. Clin. Invest., 80, 458–465(1987); H. G. Kraft et al., Arteriosclerosis, 8, 212–216(1988); G. Utermann et al., Hum. Genet., 78, 41–46(1988)]. This is considered to be due to differences in the number of repetition of the Kringle 4-corresponding portion of apolipoprotein (a) [V. N. Trieu et al., J. Biol. Chem., 266, 5480–5485(1991)]. As a result of fractionation by a combination of SDS electrophoresis and an immunological blot technique, F, B, S1, S2, S3, S4 and O isotypes have been detected [G. Utermann et al., J. Clin. Invest., 80, 458–465(1987)].

Clinically, it has been found that the level of lipoprotein (a) is high in many patients with ischemic heart diseases such as angina pectoris and myocardial infarction [G. Dahlen et al., Acta Med. Scand., (Suppl.) 531, 1–29(1972); K. Berg et al., Clin. Genet., 16, 347–352(1979); G. M. Kostner et al., Atherosclerosis, 38, 51–61(1981)]. Moreover, it has been reported that lipoprotein (a) shows no correlation with known risk factors involved in ischemic heart diseases, such as cholesterol, LDL-cholesterol and HDL-cholesterol, and is a new independent risk factor involved in arteriosclerosis and ischemic heart diseases [C. Ehnholm et al., Biochim. Biophys. Acta, 236, 431–439(1971); H. Schriewer et al., J. Clin. Chem. Clin. Biochem., 22, 591–596(1984)].

In 1987, Eaton et al. determined the amino acid sequence of apolipoprotein (a) according to biochemical techniques [D. L. Eaton et al., Proc. Natl. Acad. Sci. U.S.A., 84, 3224–3228(1987)]. Then, McLean et al. determined it on the basis of the base sequence of cDNA [J. W. McLean et al., Nature, 330, 132–137(1987)].

Thus, it has been found that the greater part of the molecular structure of apolipoprotein (a) is composed of portions having high homology with the plasminogen molecule acting on the fibrinolytic system.

This suggests that lipoprotein (a) and apolipoprotein (a) will provide an important key when arteriosclerosis, lipoprotein and the blood clotting and fibrinolytic system are considered from an identical point of view.

Moreover, it has been reported that lipoprotein (a) is not only a risk factor involved in arteriosclerosis, but also shows an increasing tendency in patients with diabetic nephropathy or reconstriction after PTCA (percutaneous transluminal coronary angioplasty), and that lipoprotein (a) behaves like acute phase reactive proteins such as CRP. Thus, the determination of lipoprotein (a) and apolipoprotein present in biological samples such as blood has come to be of important significance from a clinical point of view and, therefore, there is a demand for a method which enables accurate determination of lipoprotein (a) and apolipoprotein (a).

The determination of lipoprotein (a) is being made according to immunological assay techniques such as single immunodiffusion, rocket immunoelectrophoresis, turbidimetric immunoassay, latex turbidimetric immunoassay, radioimmunoassay (RIA) [J. J. Albers et al., J. Lipid Res., 18, 331–338(1977)] and enzyme immunoassay (EIA, ELISA) [A. Abe et al., Clin. Chim. Acta, 177, 31–40(1988)]. If an antibody prepared by administering lipoprotein (a) as an immunogen to an animal is used directly in these immunological assay techniques, it is impossible to obtained accurate measured values for lipoprotein (a). The reason for this is that, lipoprotein (a) contains LDL in its molecule and includes portions having high homology with plasminogen, the antibody reacts with any LDL and plasminogen present in biological samples and, therefore, LDL and plasminogen are measured together with lipoprotein (a).

Accordingly, there has been proposed a method which comprises preparing an antiserum (polyclonal antibody) to lipoprotein (a) by using, as an immunogen, apolipoprotein (a) obtained by removing the LDL moiety from lipoprotein (a) [G. M. Fless et al., J. Biol. Chem., 261, 8712–8718 (1986); G. Utermann et al., J. Biol. Chem., 265, 981–986 (1990)]. Although the antiserum (polyclonal antibody) obtained by this method does not show a cross reaction with LDL, it has cross reactivity with plasminogen because apolipoprotein (a) contains a portion having high homology with plasminogen.

For that reason, this antiserum (polyclonal antibody) cannot be used before it is subjected to a troublesome procedure for removing antibodies reacting with plasminogen by an absorption treatment with plasminogen.

Where apolipoprotein (a) is determined specifically (i.e., where apolipoprotein (a) formed by breakage of the disulfide bond in lipoprotein (a) is determined), it is conceivable to prepare an antiserum (polyclonal antibody) by using apolipoprotein (a) as an immunogen and apply it to an immunological assay technique as described above.

However, since the antiserum (polyclonal antibody) prepared by using apolipoprotein (a) as an immunogen also reacts with lipoprotein (a), it is necessary to remove therefrom an antibody reacting with lipoprotein (a) by an absorption treatment with lipoprotein (a), in addition to the absorption treatment with human plasminogen. This is not only troublesome, but also disadvantageous in that it is difficult to obtain the an antiserum (polyclonal antibody) in large amount because of its low yield.

Moreover, the antisera and polyclonal antibodies to lipoprotein (a) or apolipoprotein (a) which are prepared in the above-described manner show very great lot-to-lot variation. As a result, if determinations of lipoprotein (a) or apolipoprotein (a) are made under the same conditions, the measured values may vary according to the lot of the antiserum or polyclonal antibody. Accordingly, it is necessary to readjust the measuring conditions from lot to lot.

Also known is a method which comprises preparing a monoclonal antibody to lipoprotein (a) or apolipoprotein (a) by using lipoprotein (a) or apolipoprotein (a) as an immunogen, and selecting a cell strain productive of an antibody not reacting with LDL or plasminogen [D. L. Eaton et al., Clin. Chem., 36, 192–197(1990); M. A. Lafferty et al., J. Lipid Res., 32, 277–292(1991)]. Among the antibody-producing cell strains obtained in this method, however, there are only a few cell strains productive of an antibody satisfying the requirements that they should be specific for lipoprotein (a) and should not show a cross reaction with LDL or plasminogen, or the requirements that they should be specific for apolipoprotein (a) and should not show a cross reaction with lipoprotein (a) or plasminogen. Thus, the selection of such antibody-producing cell strains from a great number of antibody-producing cell strains is an inefficient procedure requiring much labor and time.

Moreover, lipoprotein (a) and apolipoprotein (a), which are used as immunogens for producing the above-described antiserum, polyclonal antibody and monoclonal antibody, must be obtained by purification from biological samples. This purification procedure is delicate and troublesome.

Furthermore, lipoprotein (a) and apolipoprotein (a) used as immunogens have the disadvantage that they are not satisfactorily stable. Accordingly, even if they are purified through a troublesome procedure, it is difficult to store them for a long period of time.

In addition, when apolipoprotein (a) for use as an antibody-producing immunogen is prepared by removing the LDL moiety from lipoprotein (a), apolipoprotein (a) may be denatured during the course of its purification. Thus, it is very likely that the resulting product is not native apolipoprotein (a).

Accordingly, the conventional antibodies to lipoprotein (a) or apolipoprotein (a) and the conventional immunogens for producing these antibodies have the disadvantage that they require the above-described complicated procedures for absorption treatment, for the correction of lot-to-lot variation, for the selection of an antibody-producing cell strain, and for the purification of an immunogen, and involve much labor, time and cost.

DISCLOSURE OF THE INVENTION

In view of the above-described existing circumstances, the present inventors made exhaustive investigations for the purpose of developing antibodies specifically recognizing lipoprotein (a) which do not show a cross reaction with LDL or plasminogen and can hence be obtained without requiring troublesome procedures such as ones for absorption treatment with LDL or plasminogen, for the selection of a cell strain productive of an antibody showing no cross reaction with LDL or plasminogen, for the correction of lot-to-lot variation, and for the purification of an immunogen, and with less labor, time and cost as compared with prior art antibodies and methods, immunogens for producing these antibodies which can be obtained with less labor, time and cost as compared with prior art immunogens and methods, a method for the determination of lipoprotein (a) using these antibodies, and peptides selected from the amino acid sequence of lipoprotein (a) which peptides can be obtained with less labor, time and cost as compared with prior art peptides and methods.

The present inventors also made exhaustive investigations for the purpose of developing antibodies specifically recognizing apolipoprotein (a) which do not show a cross reaction with lipoprotein (a) or plasminogen and can hence be obtained without requiring troublesome procedures such as ones for absorption treatment with lipoprotein (a) or plasminogen, for the selection of a cell strain productive of an antibody showing no cross reaction with lipoprotein (a) or plasminogen, for the correction of lot-to-lot variation, and for the purification of an immunogen, and with less labor, time and cost as compared with prior art antibodies and methods, immunogens for producing these antibodies which can be obtained with less labor, time and cost as compared with prior art immunogens and methods, a method for the determination of apolipoprotein (a) using these antibodies, and peptides selected from the amino acid sequence of apolipoprotein (a) which peptides can be obtained with less labor, time and cost as compared with prior art peptides and methods.

As a result, the present inventors have completed this invention.

[1] SUMMARY OF THE INVENTION

The present invention includes the following inventions:

(1) A peptide composed of 50 or less amino acids and including a part or the whole of the amino acid sequence which is selected from the amino acid sequence of lipoprotein (a) and is represented by SEQ ID NO:1 or SEQ ID NO:2 in the List of Sequences.

(2) A peptide composed of 50 or less amino acids and including a part or the whole of the amino acid sequence which is selected from the amino acid sequence of apolipoprotein (a) and is represented by SEQ ID NO:3 in the List of Sequences.

(3) An immunogen for producing an antibody to lipoprotein (a) which comprises a peptide composed of 50 or less amino acids, including a part or the whole of the amino acid sequence represented by SEQ ID NO:i in the List of Sequences.

(4) An immunogen as described above in (3) wherein the peptide composed of 50 or less amino acids, including a part or the whole of the amino acid sequence represented by SEQ ID NO:1 in the List of Sequences is combined with a carrier.

(5) An immunogen for producing an antibody to lipoprotein (a) which comprises a peptide composed of 50 or less amino acids, including a part or the whole of the amino acid sequence represented by SEQ ID NO:2 in the List of Sequences.

(6) An immunogen as described above in (5) wherein the peptide composed of 50 or less amino acids, including a part or the whole of the amino acid sequence represented by SEQ ID NO:2 in the List of Sequences is combined with a carrier.

(7) An immunogen for producing an antibody to apolipoprotein (a) which comprises a peptide composed of 50 or less amino acids, including a part or the whole of the amino acid sequence represented by SEQ ID NO:3 in the List of Sequences.

(8) An immunogen as described above in (7) wherein the peptide composed of 50 or less amino acids, including a part or the whole of the amino acid sequence represented by SEQ ID NO:3 in the List of Sequences is combined with a carrier.

(9) A polyclonal antibody to lipoprotein (a) which specifically recognizes a part or the whole of the amino acid sequence represented by SEQ ID NO:1 in the List of Sequences.

(10) A polyclonal antibody as wherein the part (9) wherein the part of the amino acid sequence represented by SEQ ID NO:1 in the List of Sequences is the amino acid sequence represented by SEQ ID NO:4 in the List of Sequences.

(11) A polyclonal antibody as described above in (9) which is obtained from an immunogen as described above in (3).

(12) An antibody to lipoprotein (a) which specifically recognizes a part or the whole of the amino acid sequence represented by SEQ ID NO:2 in the List of Sequences.

(13) An antibody as described above in (12) wherein the part of the amino acid sequence represented by SEQ ID NO:2 in the List of Sequences is the amino acid sequence represented by SEQ ID NO:5 in the List of Sequences.

(14) An antibody as described above in (12) which is obtained from an immunogen as described above in (5).

(15) An antibody as described above in (12), (13) or (14) which is a monoclonal antibody.

(16) An antibody to apolipoprotein (a) which specifically recognizes a part or the whole of the amino acid sequence represented by SEQ ID N0:3 in the List of Sequences.

(17) An antibody as described above in (16) wherein the part of the amino acid sequence represented by SEQ ID NO:3 in the List of Sequences is the amino acid sequence represented by SEQ ID NO:6 in the List of Sequences.

(18) An antibody as described above in (16) which is obtained from an immunogen as described above in (7).

(19) An antibody as described above in (16), (17) or (18) which is a monoclonal antibody.

(20) A method for the determination of lipoprotein (a) which comprises using at least one antibody as described above in any of (9) to (15).

(21) A method for the determination of apolipoprotein (a) which comprises using at least one antibody as described above in any of (16) to (19).

[2] Selected amino acid sequences and peptides

In the present invention, the term "amino acid sequence selected from the amino acid sequence of lipoprotein (a)" refers to any amino acid sequence that is characterized by having specificity as lipoprotein (a) and low homology with LDL and plasminogen and that has been selected from the amino acid sequence of lipoprotein (a).

Amino acid sequences having such characteristic features and peptides including a part or the whole of such amino acid sequences exhibit the same antigenicity as that possessed by lipoprotein (a) and do not have the antigenicity of LDL or plasminogen. That is, they have immunogenicity capable of inducing the production of antibodies recognizing lipoprotein (a) specifically and can combine specifically with antibodies to lipoprotein (a). Thus, they serve to determine antibodies recognizing lipoprotein (a) specifically and are hence useful, for example, as immunogens for producing antibodies recognizing lipoprotein (a) specifically, as standard reference materials in the determination of lipoprotein (a) by an immunological assay technique, or as ligands in the purification of antibodies recognizing lipoprotein (a) specifically by affinity chromatography.

Also in the present invention, the term "amino acid sequence selected from the amino acid sequence of apolipoprotein (a)" refers to any amino acid sequence that is characterized by having specificity as apolipoprotein (a) and low homology with plasminogen and not having antigenicity as lipoprotein (a) and that has been selected from the amino acid sequence of apolipoprotein (a).

Amino acid sequences having such characteristic features and peptides including a part or the whole of such amino acid sequences exhibit the same antigenicity as that possessed by apolipoprotein (a) and do not have the antigenicity of lipoprotein (a) or plasminogen. That is, they have immunogenicity capable of inducing the production of antibodies recognizing apolipoprotein (a) specifically and can combine specifically with antibodies to apolipoprotein (a). Thus, they serve to determine antibodies recognizing apolipoprotein (a) specifically and are hence useful, for example, as immunogens for producing antibodies recognizing apolipoprotein (a) specifically, as standard reference materials in the determination of apolipoprotein (a) by an immunological assay technique, or as ligands in the purification of antibodies recognizing apolipoprotein (a) specifically by affinity chromatography.

When the amino acid sequences of the present invention satisfying the two requirements that (1) they should have specificity as lipoprotein (a) and (2) they should have low homology with LDL and plasminogen are selected from the amino acid sequence of lipoprotein (a), the amino acid sequence of apolipoprotein (a) must be used as a source in order to eliminate the participation of LDL.

Similarly, the amino acid sequence of the present invention satisfying the two requirements that (1) they should have specificity as apolipoprotein (a) and (2) they should not have antigenicity as lipoprotein (a) or plasminogen is also selected from the amino acid sequence of apolipoprotein (a).

It is desirable that such amino acid sequences are selected from an amino acid sequence repeated in apolipoprotein (a) as many times as possible. The reason for this is that an antibody obtained by using a peptide including such an amino acid sequence as an antibody-producing immunogen is expected to combine with lipoprotein (a) or apolipoprotein (a) in large numbers. This is advantageous in the determination of lipoprotein (a) or apolipoprotein (a) and, moreover, it is very likely that such an antibody can provide accommodation for various isotypes of lipoprotein (a) or apolipoprotein (a).

Such an amino acid sequence is selected from the amino acid sequence of apolipoprotein (a) that is composed of 4,529 amino acids.

The amino acid sequence so selected is divided into several segments and examined.

When viewed from the standpoint of the stereostructure of protein, the amino acid sequence of a portion which has a high degree of hydrophilicity, is very likely present on the surface of the protein molecule, is not contained in a special stereostructure and belongs to a flexible structure having a high degree of spatial wobble is considered to be suitable for use as an amino acid sequence specifically representing the antigenicity of the substance used as an antibody-producing immunogen or the like.

Accordingly, the nature of each segment is estimated from this viewpoint.

First of all, the degree of hydrophilicity of each amino acid residue is estimated according to the method of Hopp et al. [T. P. Hopp et al., Proc. Natl. Acad. Sci. U.S.A., 78, 3824–3828(1981)] and the method of Parker et al. [Parker et al., Biochemistry, 25, 5425–5432(1986)].

Moreover, according to the method of Garnier et al. [Garnier et al., J. Mol. Biol., 120, 97–120(1987)], an estimation is made to determine whether each amino acid residue belongs to a special stereostructure.

Furthermore, according to the method of Karplus et al. [Karplus et al., Naturwissenschaften, 72, 212–213(1985)], an estimation is made to determine whether each amino acid residue belongs to a flexible structure having a high degree of spatial wobble.

In addition, reference may be made to the results of an investigation by Scanu in which an estimation was made to determine the tendency for the amino acid residues of apolipoprotein (a) to assume an α-helix structure and a β-structure [A. M. Scanu, "Lipoprotein (a)", Academic Press, San Diego, 1990, p. 53–74].

On the basis of the results thus obtained, segments having an amino acid sequence satisfying the above-described requirements are selected.

In order to obtain the present amino acid sequences selected from the amino acid sequence of lipoprotein (a), the amino acid sequences of the segments selected as above are carefully compared with the amino acid sequence of plasminogen to find out amino acid sequences having low homology with the latter. Among these amino acid sequences, those having suitability for use as immunogens for producing an antibody to lipoprotein (a) are employed.

The amino acid sequences of the present invention which are represented by SEQ ID NO:1 and SEQ ID NO:2 in the List of Sequences have been selected in the above-described manner.

In order to obtain the present amino acid sequence selected from the amino acid sequence of apolipoprotein (a), the amino acid sequences of the segments selected as above are carefully compared with the amino acid sequence of plasminogen to find out amino acid sequences having low homology with the latter.

As the next step, in order to examine the antigenicity of these amino acid sequences as lipoprotein (a), antibodies are prepared using peptides including these amino acid sequences as antibody-producing immunogens, and the reactivity of the resulting antibodies with lipoprotein (a) is tested by the western blot technique or the like. At the same time, the reactivity of these antibodies with apolipoprotein (a) is tested by the western blot technique or the like.

On the basis of the finding thus obtained, an amino acid sequence included in the immunogens of the antibodies not reacting with lipoprotein (a) is selected as an amino acid sequence having no antigenicity as lipoprotein (a).

The amino acid sequence of the present invention which is represented by SEQ ID NO:3 in the List of Sequences has been selected in the above-described manner.

The present peptides composed of 50 or less amino acids and including a part or the whole of the amino acid sequence which is selected from the amino acid sequence of lipoprotein (a) and is represented by SEQ ID NO:1 or SEQ ID NO:2 in the List of Sequences satisfy the two requirements that (1) they should have specificity as lipoprotein (a) and (2) they should have low homology with LDL and plasminogen, and exhibit antigenicity specific for lipoprotein (a) without exhibiting the antigenicity of LDL and plasminogen. Thus, they serve to determine antibodies recognizing lipoprotein (a) specifically and are hence useful, for example, as immunogens for producing such antibodies, as standard reference materials in the determination of lipoprotein (a), and as ligands in the purification of antibodies recognizing lipoprotein (a) specifically.

The present peptides composed of 50 or less amino acids and including a part or the whole of the amino acid sequence which is selected from the amino acid sequence of apolipoprotein (a) and is represented by SEQ ID NO:3 in the List of Sequences satisfy the two requirements that (1) they should have specificity as apolipoprotein (a) and (2) they should not have antigenicity as lipoprotein (a) or plasminogen, and exhibit antigenicity specific for apolipoprotein (a) without exhibiting the antigenicity of lipoprotein (a) and plasminogen. Thus, they serve to determine antibodies recognizing apolipoprotein (a) specifically and are hence useful, for example, as immunogens for producing such antibodies, as standard reference materials in the determination of apolipoprotein (a), and as ligands in the purification of antibodies recognizing apolipoprotein (a) specifically.

In the present peptides composed of 50 or less amino acids and including a part or the whole of the amino acid sequence which is selected from the amino acid sequence of lipoprotein (a) and is represented by SEQ ID NO:1 or SEQ ID NO:2 in the List of Sequences, and the present peptides composed of 50 or less amino acids and including a part or the whole of the amino acid sequence which is selected from the amino acid sequence of apolipoprotein (a) and is represented by SEQ ID NO:3 in the List of Sequences, the part of the amino acid sequence may be any sequence of consecutive amino acids included in the amino acid sequence represented by SEQ ID NO:1, SEQ ID NO:2 or SEQ ID NO:3. Since there is a report that an antibody can recognize an amino acid sequence composed of 3 amino acids [F. Hudecz et al., J. Immunol. Methods, 147, 201–210(1992)], the part of the amino acid sequence may preferably be any sequence of 3 or more consecutive amino acids included in the amino acid sequence represented by SEQ ID NO:1, SEQ ID NO:2 or SEQ ID NO:3.

Moreover, the peptides composed of 50 or less amino acids and including a part or the whole of the amino acid sequence represented by SEQ ID NO:1 or SEQ ID NO:2 in the List of Sequences are intended to cover, in addition to peptides consisting of a part or the whole of the amino acid sequence represented by SEQ ID NO:1 or SEQ ID NO:2, such peptides having one or more additional amino acid(s) or peptide(s) linked to the N-terminus or C-terminus, or both the N- and C-termini. No particular limitation is placed on the amino acid(s) or peptide(s) so linked, provided that they do not include an amino acid sequence having high homology with LDL or plasminogen. However, if the number of amino acids is so increased as to form a large-sized peptide, homology with LDL or plasminogen may be produced and its stereostructure may be so complicated as to cause the peptide to assume a special stereostructure. Accordingly, the peptides of the present invention should preferably be composed of 50 or less amino acids, and more preferably 30 or less amino acids.

Furthermore, the peptides composed of 50 or less amino acids and including a part or the whole of the amino acid sequence represented by SEQ ID NO:3 in the List of Sequences are intended to cover, in addition to peptides consisting of a part or the whole of the amino acid sequence represented by SEQ ID NO:3, such peptides having one or more additional amino acid(s) or peptide(s) linked to the N-terminus or C-terminus, or both the N- and C-termini. No particular limitation is placed on the amino acid(s) or peptide(s) so linked, provided that they do not include an amino acid sequence having high homology with plasminogen or amino acid sequences having antigenicity as lipoprotein (a). However, if the number of amino acids is so increased as to form a large-sized peptide, homology with plasminogen or antigenicity as lipoprotein (a) may be produced and its stereostructure may be so complicated as to cause the peptide to assume a special stereostructure. Accordingly, the peptides of the present invention should preferably be composed of 50 or less amino acids, and more preferably 30 or less amino acids.

The present peptides composed of 50 or less amino acids and including a part or the whole of the amino acid sequence which is selected from the amino acid sequence of lipoprotein (a) and is represented by SEQ ID NO:1 or SEQ ID NO:2 in the List of Sequences, and the present peptides composed of 50 or less amino acids and including a part or the whole of the amino acid sequence which is selected from the amino acid sequence of apolipoprotein (a) and is represented by SEQ ID NO:3 in the List of Sequences, can be synthesized by any of various peptide synthesis processes including the liquid phase process and the solid phase process, or by use of an automatic peptide synthesizer. For example, they can be synthesized according to any of the processes described in the Japanese Biochemical Society (ed.) "Course of Lectures on Biochemical Experiments 1, Chemistry of Proteins IV", Tokyo Kagaku Dojin, 1975; Izumiya et al., "Foundation and Experimentation for Peptide Synthesis", Maruzen, 1985; and the Japanese Biochemical Society (ed.), "Course of Lectures on Biochemical ExpeChemiss (second series) 2, Chemistry of Proteins II", Tokyo Kagaku Dojin, 1987.

Alternatively, these peptides may be prepared from DNA having the corresponding sequences according to the recombinant DNA technique. For example, such preparation can be carried out by reference to the Japanese Biochemical Society (ed.), "Course of Lectures on Biochemical Experiments (second series) 1, Method for Gene Research I", Tokyo Kagaku Dojin, 1986; the Japanese Biochemical Society (ed.), "Course of Lectures on Biochemical Experiments (second series) 1, Method for Gene Research II", Tokyo Kagaku Dojin, 1986; and the Japanese Biochemical Society (ed.), "Course of Lectures on Biochemical Experiments (second series) 1, Method for Gene Research III", Tokyo Kagaku Dojin, 1987.

[3] Antibody-producing immunogens

In the present immunogens for producing an antibody to lipoprotein (a) which comprise peptides composed of 50 or less amino acids, including a part or the whole of the amino acid sequence represented by SEQ ID NO:1 or SEQ ID NO:2 in the List of Sequences, the peptides composed of 50 or less amino acids, including a part or the whole of the amino acid sequence represented by SEQ ID NO:1 or SEQ ID NO:2 in the List of Sequences comprise the above-described present peptides composed of 50 or less amino acids and including a part or the whole of the amino acid sequence which is selected from the amino acid sequence of lipoprotein (a) and is represented by SEQ ID NO:1 or SEQ ID NO:2 in the List of Sequences.

These present immunogens for producing an antibody to lipoprotein (a) which comprise peptides composed of 50 or less amino acids, including a part or the whole of the amino acid sequence represented by SEQ ID NO:1 or SEQ ID NO:2 in the List of Sequences make it possible to obtain antibodies satisfying the two requirements that (1) they should recognize lipoprotein (a) specifically and (2) they should not show a cross reaction with LDL or plasminogen.

In the present immunogens for producing an antibody to apolipoprotein (a) which comprise peptides composed of 50 or less amino acids, including a part or the whole of the amino acid sequence represented by SEQ ID NO:3 in the List of Sequences, the peptides composed of 50 or less amino acids, including a part or the whole of the amino acid sequence represented by SEQ ID NO:3 in the List of Sequences comprise the above-described present peptides composed of 50 or less amino acids and including a part or the whole of the amino acid sequence which is selected from the amino acid sequence of apolipoprotein (a) and is represented by SEQ ID NO:3 in the List of Sequences.

These present immunogens for producing an antibody to apolipoprotein (a) which comprise peptides composed of 50 or less amino acids, including a part or the whole of the amino acid sequence represented by SEQ ID NO:3 in the List of Sequences make it possible to obtain antibodies satisfying the two requirements that (1) they should recognize apolipoprotein (a) specifically and (2) they should not show a cross reaction with lipoprotein (a) or plasminogen.

In using the present immunogens for producing an antibody to lipoprotein (a) which comprise peptides composed of 50 or less amino acids, including a part or the whole of the amino acid sequence represented by SEQ ID NO:1 or SEQ ID NO:2 in the List of Sequences, and the present immunogens for producing an antibody to apolipoprotein (a) which comprise peptides composed of 50 or less amino acids, including a part or the whole of the amino acid sequence represented by SEQ ID NO:3 in the List of Sequences, these peptides alone may be administered to animals as antibody-producing immunogens, or these peptides may be combined with a carrier and then administered to animals as antibody-producing immunogens.

Where the immunogens are low-molecular-weight substances, it is common to use them in a form combined with a carrier. However, there is a report that a peptide composed of 5 amino acids could be used as an immunogen to produce an antibody specific therefor (Kiyama et al., Synopses of Lectures Given at the 112th Annual Meeting of the Pharmaceutical Society of Japan, Vol. 3, 1992, P. 122). Accordingly, it is not essential to use a carrier.

Where it is desired to use a carrier, there may be used any of well-known carriers such as keyhole limpet hemocyanin (KLH), bovine serum albumin (BSA), human serum albumin, chicken serum albumin, poly-L-lysine, polyalanyllysine, dipalmityllysine, tetanus toxoid and polysaccarides.

In order to combine the peptides of the present invention with carriers, there may be employed any of well-known methods such as the glutaraldehyde method, the 1-ethyl-3-(3-dimethylaminopropyl)carbodiimide method, the maleimidobenzoyl-N-hydroxysuccinimido ester method, the N-succinimidyl-3-(2-pyridyldithio)propionic acid method, the bisdiazotized benzidine method and the dipalmityllysine method.

Alternatively, the above-described peptides may be adsorbed onto a carrier such as nitrocellulose particles, polyvinyl pyrrolidone or liposomes and used as antibody-producing immunogens.

The present immunogens for producing an antibody to lipoprotein (a) which comprise peptides composed of 50 or less amino acids, including a part or the whole of the amino acid sequence represented by SEQ ID NO:1 or SEQ ID NO:2 in the List of Sequences, and the present immunogens for producing an antibody to apolipoprotein (a) which comprise peptides composed of 50 or less amino acids, including a part or the whole of the amino acid sequence represented by SEQ ID NO:3 in the List of Sequences, are stable because of their low molecular weights and can be stored for a long period of time.

[4] Antibodies

The present polyclonal antibodies to lipoprotein (a) which specifically recognize a part or the whole of the amino acid sequence represented by SEQ ID NO:1 in the List of Sequences, and the present antibodies to lipoprotein (a) which specifically recognize a part or the whole of the amino acid sequence represented by SEQ ID NO:2 in the List of Sequences, do not show a cross reaction with LDL or plasminogen, and can be used as antibodies recognizing lipoprotein (a) specifically.

The above-described polyclonal antibodies and antibodies to lipoprotein (a) have a specific affinity for a part or the whole of those amino acid sequences in lipoprotein (a). In other words, they have the property of combining specifically with a part or the whole of those amino acid sequences.

Thus, the above-described polyclonal antibodies and antibodies to lipoprotein (a) in accordance with the present invention can combine specifically with not only lipoprotein (a), but also peptides or proteins including a part or the whole of the amino acid sequence represented by SEQ ID NO:1 or SEQ ID NO:2 in the List of Sequences, respectively, In view of the fact that an antibody recognizes the antigenic determinants (or epitopes) of an antigen stereostructurally, it is to be understood that the term "a part of the amino acid sequence" as used herein is not limited to a sequence of adjoining amino acids in the primary structure of these amino acid sequences, but means any combination of 3 or more amino acids in these amino acid sequences.

In connection with the above-described polyclonal antibodies and antibodies to lipoprotein (a) in accordance with the present invention, these amino acid sequences can further be reduced in size from the viewpoint of low homology with plasminogen. The amino acid sequences thus obtained include the amino acid sequence represented by SEQ ID NO:4 for the amino acid sequence represented by SEQ ID NO:2 in the List of Sequences, and the amino acid sequence represented by SEQ ID NO:5 for the amino acid sequence represented by SEQ ID NO:2 in the List of Sequences.

Similarly, the present antibodies to apolipoprotein (a) which specifically recognize a part or the whole of the amino acid sequence represented by SEQ ID NO:3 in the List of Sequences do not show a cross reaction with lipoprotein (a) or plasminogen, and can be used as antibodies recognizing apolipoprotein (a) specifically.

The reason why the present antibodies to apolipoprotein (a) which specifically recognize a part or the whole of the amino acid sequence represented by SEQ ID NO:3 in the List of Sequences do not combine with lipoprotein (a) containing apolipoprotein (a) within its molecule, but specifically recognize and combine with apolipoprotein (a) formed by breakage of the disulfide bond in lipoprotein (a), is presumed to lie in the differences in stereostructure, though it cannot be said definitely at present.

The present antibodies to apolipoprotein (a) which specifically recognize a part or the whole of the amino acid sequence represented by SEQ ID NO:3 in the List of Sequences have a specific affinity for a part or the whole of this amino acid sequence in apolipoprotein (a). In other words, they have the property of combining specifically with a part or the whole of this amino acid sequence.

Thus, the present antibodies to apolipoprotein (a) which specifically recognize a part or the whole of the amino acid sequence represented by SEQ ID NO:3 in the List of Sequences can combine specifically with not only apolipoprotein (a), but also peptides or proteins including a part or the whole of the amino acid sequence represented by SEQ ID NO:3 in the List of Sequences.

In view of the fact that an antibody recognizes the antigenic determinants (or epitopes) of an antigen stereostructurally, it is to be understood that the term "a part of the amino acid sequence" as used herein is not limited to a sequence of adjoining amino acids in the primary structure of this amino acid sequence, but means any combination of 3 or more amino acids in this amino acid sequence.

In connection with the present antibodies to apolipoprotein (a) which specifically recognize a part or the whole of the amino acid sequence represented by SEQ ID NO:3 in the List of Sequences, this amino acid sequence can further be reduced in size from the viewpoint of low homology with plasminogen. The amino acid sequences thus obtained include the amino acid sequence represented by SEQ ID NO:6.

The present polyclonal antibodies to lipoprotein (a) which specifically recognize a part or the whole of the amino acid sequence represented by SEQ ID NO:1 in the List of Sequences, and the present antibodies to lipoprotein (a) which specifically recognize a part or the whole of the amino acid sequence represented by SEQ ID NO:2 in the List of Sequences, can be obtained by immunizing animals with an immunogen for producing an antibody to lipoprotein (a) which comprises a peptide composed of 50 or less amino acids, including a part or the whole of the amino acid sequence represented by SEQ ID NO:1 or SEQ ID NO:2 in the List of Sequences, respectively.

Similarly, the present antibodies to apolipoprotein (a) which specifically recognize a part or the whole of the amino acid sequence represented by SEQ ID NO:3 in the List of Sequences can be obtained by immunizing animals with an immunogen for producing an antibody to apolipoprotein (a) which comprises a peptide composed of 50 or less amino acids, including a part or the whole of the amino acid sequence represented by SEQ ID NO:3 in the List of Sequences.

The present polyclonal antibodies to lipoprotein (a) which specifically recognize a part or the whole of the amino acid sequence represented by SEQ ID NO:1 in the List of Sequences may be in the form of polyclonal antibodies themselves or antisera comprising polyclonal antibodies. In addition, fragments (such as Fab, F(ab')$_2$ and Fab') of these antibodies are also fall within the scope of the present invention.

The present antibodies to lipoprotein (a) which specifically recognize a part or the whole of the amino acid sequence represented by SEQ ID NO:2 in the List of Sequences, and the present antibodies to apolipoprotein (a) which specifically recognize a part or the whole of the amino acid sequence represented by SEQ ID NO:3 in the List of Sequences, may be in the form of polyclonal antibodies, antisera comprising polyclonal antibodies, or monoclonal antibodies. In addition, fragments (such as Fab, F(ab')$_2$ and Fab') of these antibodies are also fall within the scope of the present invention.

The polyclonal antibodies and antisera can be prepared according to the following procedure.

First of all, a mammal (such as mouse, rabbit, rat, sheep, goat or horse) or a bird (such as chicken) is immunized by administering thereto the antibody-producing immunogen which comprises a peptide composed of 50 or less amino acids, including a part or the whole of the amino acid sequence represented by SEQ ID NO:1, SEQ ID NO:2 or SEQ ID NO:3 in the List of Sequences (either alone or in combination with a carrier).

The amount of antibody-producing immunogen administered may be suitably determined according to the type of the animal being immunized, the site of injection, and the like. For example, in the case of mice, an antibody-producing immunogen containing the above-described peptide in a single dose of 0.1 µg to 5 mg and preferably 50 µg to 1 mg per mouse is injected into a mouse aged about 5 to 10 weeks. In the case of rabbits, it is preferable to inject an antibody-producing immunogen containing the above-described peptide in a single dose of 10 µg to several tens of milligrams per rabbit.

Preferably, the antibody-producing immunogen is injected in admixture with an adjuvant. As the adjuvant, there may be used any of well-known adjuvants such as Freund's complete adjuvant, Freund's incomplete adjuvant, aluminum hydroxide adjuvant and pertussis adjuvant.

The immunizing injection may be given, for example, subcutaneously, intravenously, intraperitoneally or dorsally.

After the initial immunization, the antibody-producing immunogen is additionally injected subcutaneously, intravenously, intraperitoneally or dorsally as boosters at intervals of 2 to 3 weeks. Also in this case, the antibody-producing immunogen is preferably injected in admixture with an adjuvant.

Following the initial immunization, the antibody titer in the blood serum of the animal being immunized is repeatedly measured by ELISA or the like. As soon as the antibody titer has reached a plateau, exsanguination is performed and blood serum is separated to obtain an antiserum.

This antiserum is purified by a purification technique such as salting-out with ammonium sulfate, sodium sulfate or the like, ion exchange chromatography, gel filtration or affinity chromatography, or a combination of such techniques. Thus, there can be obtained a polyclonal antibody in accordance with the present invention.

Where human serum albumin or BSA is used as a carrier for the antibody-producing immunogen, the resulting antibody or antiserum may contain an antibody showing a cross reaction with human serum albumin. Accordingly, it is preferable to subject the resulting antibody or antiserum to a treatment for removing such an antibody. This removal treatment may be accomplished, for example, by adding human serum albumin or BSA used as a carrier to a solution of the resulting antibody or antiserum and removing the aggregates so formed, or by subjecting the resulting antibody or antiserum to affinity chromatography in which human serum albumin or BSA used as a carrier is immobilized on an insoluble carrier.

Next, the method for the preparation of monoclonal antibodies is described hereinbelow.

Monoclonal antibodies can be obtained by using antibody-producing cells such as hybridomas produced according to the cell fusion technique of Koehler et al. [G. Koehler et al., Nature, 256, 495–497(1975)], or cells tumorigenically transformed by a virus such as Epstein-Barr virus.

The preparation of a monoclonal antibody according to the cell fusion technique can be carried out in the following manner.

First of all, a mammal [such as mouse (e.g., of inbred strain BALB/c), nude mouse or rat] or a bird (such as chicken) is immunized by administering thereto an antibody-producing immunogen which comprises a peptide composed of 50 or less amino acids, including a part or the whole of the amino acid sequence represented by SEQ ID NO:2 or SEQ ID NO:3 in the List of Sequences. The amount of antibody-producing immunogen administered may be suitably determined according to the type of the animal being immunized, the site of injection, and the like. For example, in the case of mice, it is preferable to inject an antibody-producing immunogen containing the above-described peptide in a single dose of 0.1 µg to 5 mg per mouse.

Preferably, the antibody-producing immunogen is injected in admixture with an adjuvant. As the adjuvant, there may be used any of well-known adjuvants such as Freund's complete adjuvant, Freund's incomplete adjuvant, aluminum hydroxide adjuvant and pertussis adjuvant.

The immunizing injection may be given, for example, subcutaneously, intravenously, intraperitoneally or dorsally.

After the initial immunization, the antibody-producing immunogen is additionally injected subcutaneously, intravenously, intraperitoneally or dorsally as boosters at intervals of 1 to 2 weeks. The number of these booster injections is commonly in the range of 2 to 6. Also in this case, the antibody-producing immunogen is preferably injected in admixture with an adjuvant.

Following the initial immunization, the antibody titer in the blood serum of the animal being immunized is repeatedly measured by ELISA or the like. As soon as the antibody titer has reached a plateau, a final immunization is performed by injecting a solution of the antibody-producing immunogen in physiological saline (a 0.9% aqueous solution of sodium chloride) intravenously or intraperitoneally. Three to five days after this final immunization, cells having antibody-forming ability, such as spleen cells, lymph node cells or peripheral lymphocytes are collected from the immunized animal.

These antibody-forming cells obtained from the immunized animal and myeloma cells of a mammal (such as mouse, nude mouse or rat) are subjected to cell fusion. The myeloma cells are preferably of a cell strain deficient in such an enzyme as hypoxanthine-guanine phosphoribosyltransferase (HGPRT) or thymidine kinase (TK). For example, there may be used the P3-X63-Ag8 (ATCC TIB9), P3-X63-Ag8-U1 [Japanese Cancer Research Resources Bank (JCRB) 9085], P3-NS1-1-Ag4-1 (JCRB 0009), P3-X63-Ag8.653 (JCRB 0028) or SP2/0-Ag-14 (JCRB 0029) strains which are HGPRT-deficient cell strains derived from BALB/c mice.

The cell fusion can be effected with the aid of a fusion promoter such as polyethylene glycols (PEG) having various molecular weights, liposomes or Sendai virus (HVJ), or by the electrical fusion method.

Where the myeloma cells are of a HGPRT- or TK-deficient strain, only fused cells (hybridomas) consisting of an antibody-forming cell and a myeloma cell can be selectively cultured and grown by using a screening medium containing hypoxanthine, aminopterin and thymidine (HAT medium).

By testing the supernatants obtained from the cultures of the resulting hydridomas according to an immunological assay technique such as ELISA or the western blot technique, a hybridoma productive of an antibody to lipoprotein (a) specifically recognizing a part or the whole of the amino acid sequence represented by SEQ ID NO:2 in the List of Sequences or an antibody to apolipoprotein (a) specifically recognizing a part or the whole of the amino acid sequence represented by SEQ ID NO:3 in the List of Sequences can be selected. Moreover, by using this procedure in combination with a well-known cloning technique such as limiting dilution, a cell strain productive of a monoclonal antibody in accordance with the present invention can be isolated.

By culturing this monoclonal antibody-producing cell strain in a suitable medium, the monoclonal antibody of the present invention can be obtained from the supernatant of the culture thereof. A serum-free medium or a low-serum medium may be used as the culture medium. Such media are preferred because they facilitate purification of the antibody. For example, DMEM medium, RPMI1640 medium and ASF medium may be used.

Alternatively, the monoclonal antibody-producing cell strain may be injected into the abdominal cavity of a mammal which has compatibility therewith and has previously been stimulated by pristane or the like. After the laspe of a certain period of time, the monoclonal antibody of the present invention can be obtained from the ascites accumulated in the abdominal cavity thereof.

The monoclonal antibody so produced can be purified by a purification technique such as salting-out with ammonium sulfate, sodium sulfate or the like, ion exchange chromatography, gel filtration or affinity chromatography, or a combination of such techniques. Thus, there can be obtained a purified monoclonal antibody in accordance with the present invention.

[5] Methods of determination

The present method for the determination of lipoprotein (a) which comprises using at least one antibody selected from (1) a polyclonal antibody to lipoprotein (a) which specifically recognizes a part or the whole of the amino acid sequence represented by SEQ ID NO:1 in the List of Sequences, (2) a polyclonal antibody as described above in (1) wherein the part of the amino acid sequence represented by SEQ ID NO:1 in the List of Sequences is the amino acid sequence represented by SEQ ID NO:4 in the List of Sequences, (3) a polyclonal antibody as described above in (1) that is obtained from an immunogen for producing antibody to lipoprotein (a) which comprises a peptide composed of 50 or less amino acids, including a part or the whole of the amino acid sequence represented by SEQ ID NO:1 in the List of Sequences, (4) an antibody to lipoprotein (a) which specifically recognizes a part or the whole of the amino acid sequence represented by SEQ ID NO:2 in the List of Sequences, (5) an antibody as described above in (4) wherein the part of the amino acid sequence represented by SEQ ID NO:2 in the List of Sequences is the amino acid sequence represented by SEQ ID NO:5 in the List of Sequences, (6) an antibody as described above in (4) that is obtained from an immunogen for producing antibody to lipoprotein (a) which comprises a peptide composed of 50 or less amino acids, including a part or the whole of the amino acid sequence represented by SEQ ID NO:2 in the List of Sequences, and (7) an antibody as described above in (4), (5) or (6) which is a monoclonal antibody, can determine the concentration of lipoprotein (a) accurately without measuring together any LDL or plasminogen present in the samples.

Similarly, the present method for the determination of apolipoprotein (a) which comprises using at least one antibody selected from (1) an antibody to apolipoprotein (a) which specifically recognizes a part or the whole of the amino acid sequence represented by SEQ ID NO:3 in the List of Sequences, (2) an antibody as described above in (1) wherein the part of the amino acid sequence represented by SEQ ID NO:3 in the List of Sequences is the amino acid sequence represented by SEQ ID NO:6 in the List of Sequences, (3) an antibody as described above in (1) that is obtained from an immunogen for producing antibody to apolipoprotein (a) which comprises a peptide composed of 50 or less amino acids, including a part or the whole of the amino acid sequence represented by SEQ ID NO:3 in the List of Sequences, and (4) an antibody as described above in (1), (2) or (3) which is a monoclonal antibody, can determine the concentration of apolipoprotein (a) accurately without measuring together any lipoprotein (a) or plasminogen present in the samples.

In these methods of determination in accordance with the present invention, not only one of the above-described antibodies may be used, but also two or more of them may be used in combination.

The present methods of determination may be carried out according to any assay technique using an antibody (i.e., any immunological assay technique), and can produce the desired effects by employing one of the above-described antibodies as the antibody used in the technique. For example, the present methods of determination may be carried out according to any of various techniques such as enzyme immunoassay (ELISA, EIA), fluoroimmunoassay, radioimmunoassay (RIA), luminescent immunoassay, enzyme-labeled antibody technique, fluorescent antibody technique, turbidimetric immunoassay, latex agglutination test, latex turbidimetric immunoassay, hemagglutination test, particle agglutination and western blot technique.

The samples used in the present methods of determination can be any biological samples that may contain lipoprotein (a) or apolipoprotein (a), or constituent parts thereof, such as blood, blood serum, blood plasma, urine, cerebrospinal fluid, saliva, sweat, ascites, amniotic fluid, and cell or organ extracts.

Where the present methods of determination are carried out according to immunoassays using a labeled antibody, such as enzyme immunoassay, fluoroimmunoassay, radioimmunoassay and luminescent immunoassay, either of the sandwich technique and the competitive assay technique may be employed. In the sandwich technique, an antibody as described above may be used as at least one of the antibodies combining directly with lipoprotein (a) or apolipoprotein (a), such as the capture antibody and the labeled antibody.

As the solid-phase carrier, there may be used any of various well-known solid-phase carriers, for example, in the form of beads, microplates, test tubes, sticks and test strips made of such materials as polystyrene, polycarbonate, polyvinyltoluene, polypropylene, polyethylene, polyvinyl chloride, nylon, polymethacrylate, latex, gelatin, agarose, cellulose, Sepharose, glass, metals, ceramics and magnetic materials.

The capture antibody may be prepared from a solid-phase carrier and an antibody according to a well-known technique such as physical adsorption, chemical bonding or a combination thereof.

The labeling material can be peroxidase (POD), alkaline phosphatase (ALP), $\beta$-galactosidase, urease, catalase, glucose oxidase, lactate dehydrogenase or amylase in the case of enzyme immunoassay; fluorescein isothiocyanate, tetramethylrhodamine isothiocyanate, substituted rhodamine isothiocyanate or dichlorotriazine isothiocyanate in the case of fluoroimmunoassay; and tritium, iodine-125 or iodine-131 in the case of radioimmunoassay. In luminescent immunoassay, there may be used any of various systems such as NADH-FMNH$_2$-luciferase, luminol-hydrogen peroxide-POD, acridinium ester and dioxetane compound systems.

In order to combine a labeling material with an antibody, there may be employed any of well-known methods such as the glutaraldehyde method, the maleimide method, the pyridyl disulfide method and the periodic acid method.

Measurements can be made according to any of various well-known processes [The Japanese Society of Clinical Pathology (ed.), "Clinical Pathology (extra edition), No. 53, immunoassay for Clinical Examination—Techniques and Applications—", Rinsho Byori Kankokai, 1983; Eiji Ishikawa et al. (ed.), "Enzyme Immunoassay", Third Edition, Igaku Shoin, 1987; Tsunehiro Kitagawa et al. (ed.), "Proteins, Nucleic Acids and Enzymes (extra issue), No. 31, Enzyme Immunoassay", Kyoritsu Shuppan, 1987].

For example, the capture antibody is reacted with a sample, and further reacted with the labeled antibody simultaneously or after washing. Thus, a capture antibody-lipoprotein (a)-labeled antibody or capture antibody-apolipoprotein (a)-labeled antibody complex is formed. By washing and separating the unbound labeled antibody, the amount of lipoprotein (a) or apolipoprotein (a) in the sample can be determined from the amount of the bound or unbound labeled antibody.

More specifically, in the case of enzyme immunoassay, a labeled enzyme is reacted with a substrate under the optimum conditions therefor, and the amount of the reaction product is measured by optical means or the like. The intensity of fluorescence produced by a fluorescent labeling material is measured in fluoroimmunoassay, and the amount of radiation produced by a radioactive labeling material is measured in radioimmunoassay. In the case of luminescent immunoassay, the amount of light emitted from a luminescent reaction system is measured.

Where the present methods of determination are carried out by forming aggregates of an immune complex in turbidimetric immunoassay, latex agglutination test, latex turbidimetric immunoassay, hemagglutination test or particle agglutination or the like, and measuring the transmitted or scattered light by optical means or visually, a phosphate buffer, a glycine buffer, a Tris buffer or Good's buffer can be used as the solvent and, moreover, a reaction promoter (e.g., polyethylene glycol) or a nonspecific reaction inhibitor may be contained therein.

Where a solid-phase carrier is sensitized with an antibody, the solid-phase carrier can be any of various particulate materials comprising polystyrene, styrene-butadiene copolymers, (meth)acrylate polymers, latex, gelatin, liposomes, microcapsules, erythrocytes, silica, alumina, carbon black, metallic compounds, metals, ceramics and magnetic materials.

Such sensitization can be carried out according to a well-known technique such as physical adsorption, chemical bonding or a combination thereof.

Measurements may be made according to any well-known method. For example, where measurements are made by optical means, a sample is reacted with an antibody or a solid-phase carrier sensitized with an antibody, and the light transmitted or scattered thereby is measured according to the end point or rate method.

Where measurements are made visually, a sample is reacted in a vessel such as a plate and a microplate with a solid-phase carrier sensitized with an antibody, and the degree of aggregation is evaluated visually.

Instead of visual evaluation, measurements may be made with the aid of an instrument such as microplate reader.

BEST MODE FOR CARRYING OUT THE INVENTION

Figure 1:
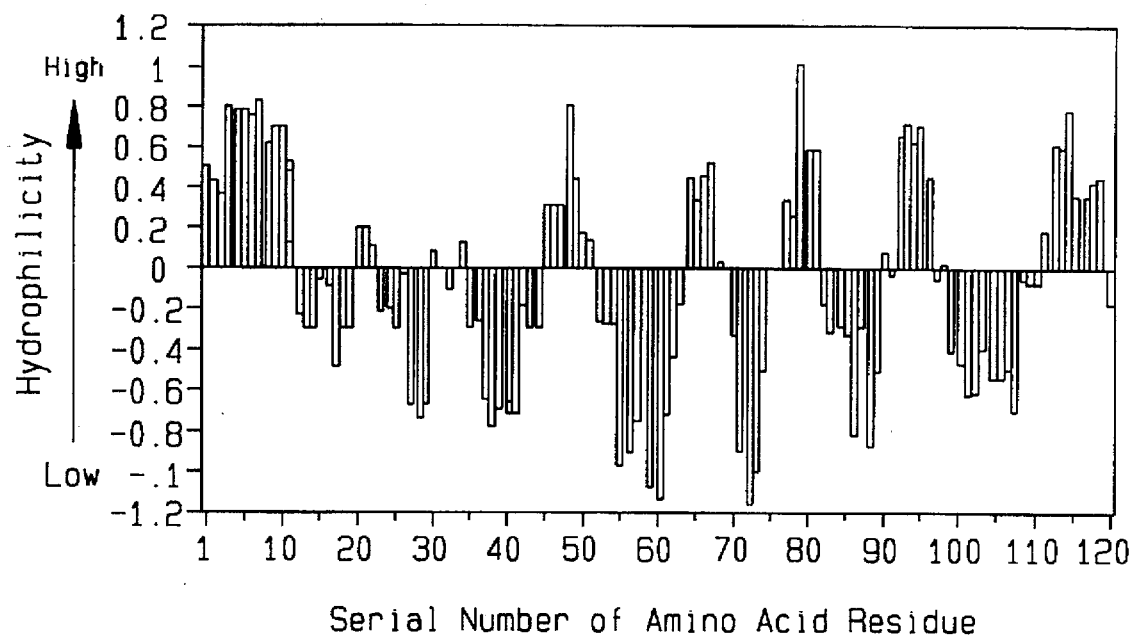
FIG. 1 is a graph showing the results of estimation of the degree of hydrophilicity of each amino acid residue according to the method of Hopp et al.

The present invention is more specifically described hereinbelow with reference to the following examples. However, the present invention is in no way to be limited by these examples.

EXAMPLE 1

Selection of amino acid sequences from lipoprotein (a)

Amino acid sequences specifically representing the antigenicity of lipoprotein (a), which are characterized by having specificity as lipoprotein (a) and low homology with LDL and plasminogen, were selected from the amino acid sequence of lipoprotein (a).

(1) In selecting amino acid sequences satisfying the two requirements (i.e., specificity as lipoprotein (a) and low homology with LDL and plasminogen) from the amino acid sequence of lipoprotein (a), the amino acid sequence of apolipoprotein (a) was used as a source in order to eliminate the participation of LDL.

Next, the 4,529-amino acid sequence of apolipoprotein (a) [J. W. McLean et al., Nature, 330, 132–137(1987)] was examined to find out a sequence repeated as many times as possible. Thus, there was selected an amino acid sequence composed of 120 amino acids and represented by SEQ ID NO:7 in the List of Sequences, which is a Kringle structure portion repeated 28 times in the sequence extending from the 110th serine to the 3,306th threonine as counted from the N-terminus of apolipoprotein (a).

(2) Employing cysteine residues as main criteria, this amino acid sequence represented by SEQ ID NO:7 was divided into 7 segments: segment 1 extending from the 3rd alanine to the 14th cysteine as counted from the N-terminus, segment 2 extending from the 15th tyrosine to the 35th cysteine, segment 3 extending from the 36th glutamine to the 63rd cysteine, segment 4 extending from the 64th arginine to the 74th cysteine, segment 5 extending from the 75th tyrosine to the 86th cysteine, segment 6 extending from the 87th asparagine to the 91st cysteine, and segment 7 extending from the 92nd serine to the 116th glutamine.

(3) In order to learn the nature of these seven segments, the 120-amino acid sequence represented by SEQ ID NO:7 was investigated in various ways.

The degree of hydrophilicity of each amino acid residue was estimated according to the method of Hoppet al. [T. P. Hopp et al., Proc. Natl. Acad. Sci. U.S.A., 78, 3824–3828 (1981)]. The results of this estimation are shown in FIG. 1.

In FIG. 1, the abscissa indicates the serial number of amino acid residue as counted from the N-terminus, while the ordinate indicates the degree of hydrophilicity in which greater values represent higher degrees of hydrophilicity and smaller values represent lower degrees of hydrophilicity.

(4) Next, the degree of hydrophilicity of each amino acid residue was estimated again according to the method of Parker et al. [Parker et al., Biochemistry, 25, 5425–5432 (1986)]. The results of this estimation are shown in FIG. 2.

Figure 2:
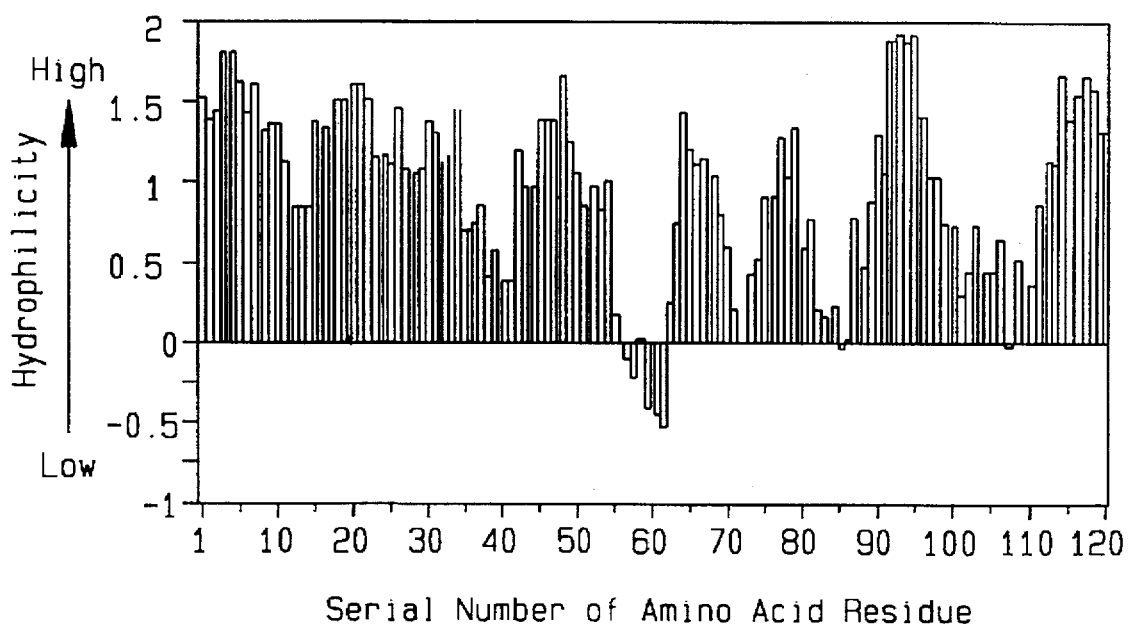
FIG. 2 is a graph showing the results of estimation of the degree of hydrophilicity of each amino acid residue according to the method of Parker et al.

In FIG. 2, the abscissa indicates the serial number of amino acid residue as counted from the N-terminus, while the ordinate indicates the degree of hydrophilicity in which greater values represent higher degrees of hydrophilicity.

(5) According to the method of Garnier et al. [Garnier et al., J. Mol. Biol., 120, 97–120(1987)], an estimation was made to determine whether each amino acid residue belongs to a special stereostructure. The results of this estimation are shown in FIG. 3.

Figure 3:
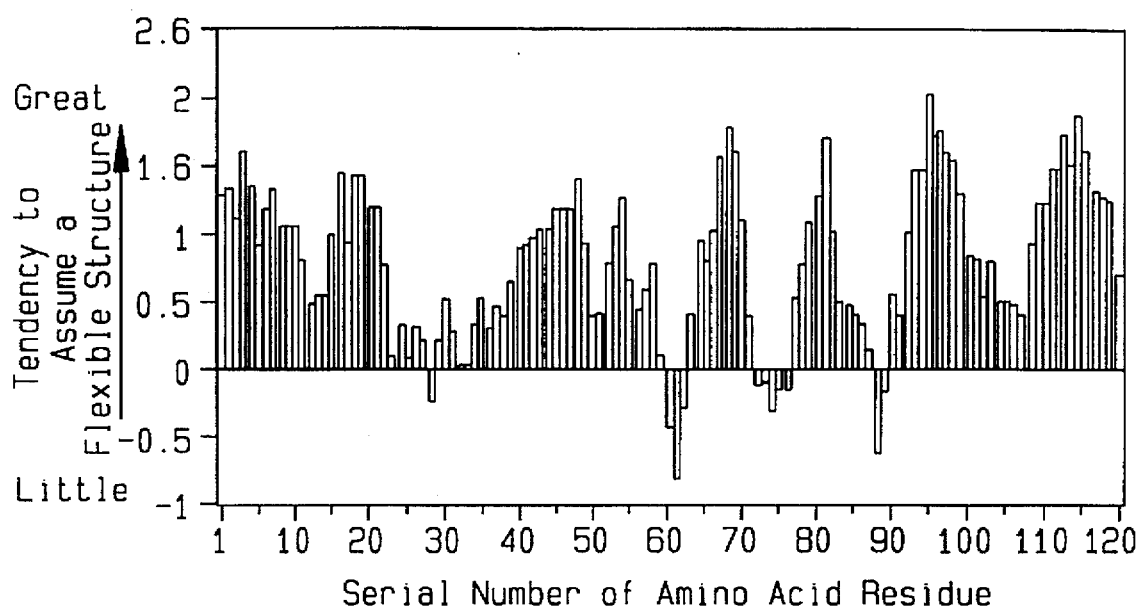
FIG. 3 is a graph showing the results of estimation as to whether or not each amino acid residue belongs to a special stereostructure, according to the method of Garnier et al.

In FIG. 3, the abscissa indicates the serial number of amino acid residue as counted from the N-terminus, while the ordinate indicates the tendency to assume a special stereostructure in which greater values represent greater tendencies to belong to a special stereostructure.

(6) According to the method of Karplus et al. [Karplus et al., Naturwissenschaften, 72, 212–213(1985)], an estimation was made to determine whether each amino acid residue belongs to a flexible structure having a high degree of spatial wobble. The results of this estimation are shown in FIG. 4.

Figure 4:
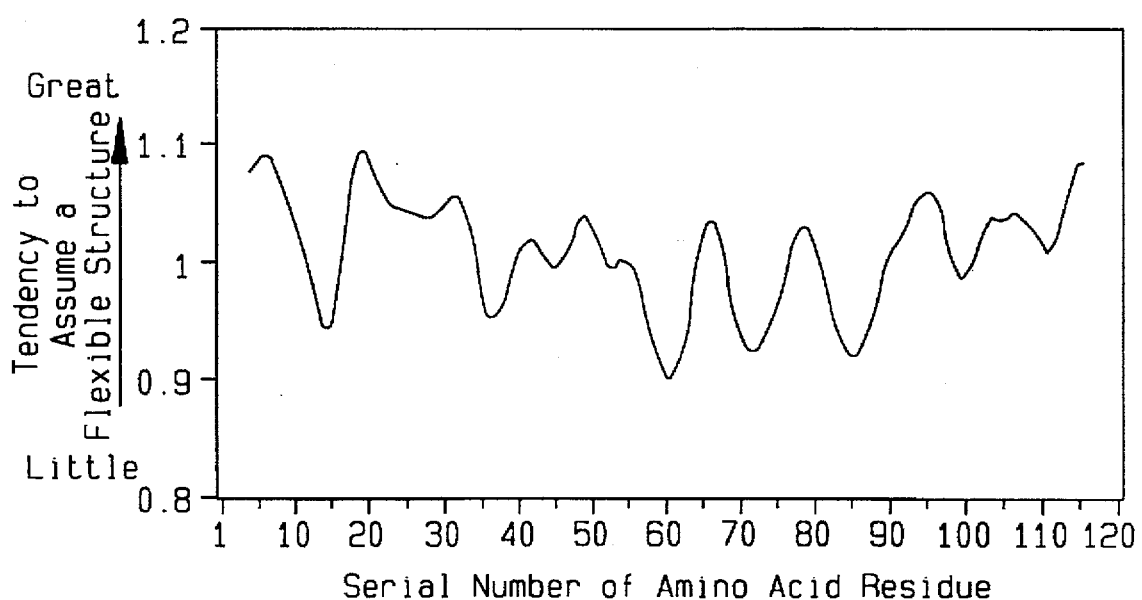
FIG. 4 is a graph showing the results of estimation as to whether or not each amino acid residue belongs to a flexible structure having a high degree of spatial wobble, according to the method of Karplus et al.

In FIG. 4, the abscissa indicates the serial number of amino acid residue as counted from the N-terminus, while the ordinate indicates the tendency to assume a flexible structure in which greater values represent greater tendencies to belong to a flexible structure having a high degree of spatial wobble.

(7) In addition, reference was made to the results of an investigation by Scanu in which an estimation was made to determine the tendency for each amino acid residue in the amino acid sequence represented by SEQ ID NO:7 to assume an α-helix structure and a β-structure [A. M. Scanu, "Lipoprotein (a)", Academic Press, San Diego, 1990, p. 53–74].

(8) As a result of examination of the foregoing data, it was thought that segment 2 is very likely to assume a β-structure which is a special stereostructure, and segment 5 is very likely to be buried in the interior of the protein molecule because of its high degree of hydrophobicity. Accordingly, the amino acid sequences of these two segments were considered to be unsuitable for use as amino acid sequences specifically representing the antigenicity as an antibody-producing immunogen or the like.

Moreover, segment 6 is not suitable for use as an amino acid sequence specifically representing antigenicity because a sugar is linked thereto, and segment 3 cannot be used because its amino acid sequence has high homology with the amino acid sequence of plasminogen.

(9) Accordingly, it was concluded that the present amino acid sequences specifically representing the antigenicity of lipoprotein (a), which are characterized by having specificity as lipoprotein (a) and low homology with LDL and plasminogen, should preferably selected from segment 1, segment 4 and segment 7. As a result of close investigation made so as to minimize homology with the amino acid sequence of plasminogen and so as to be suitable for use as immunogens for producing antibody to lipoprotein (a), the amino acid sequences represented by SEQ ID NO:1 and SEQ ID NO:2 in the List of Sequences were selected.

EXAMPLE 2

Selection of an amino acid sequence from apolipoprotein (a)

An amino acid sequence specifically representing the antigenicity of apolipoprotein (a), which is characterized by having specificity as apolipoprotein (a) and no antigenicity as lipoprotein (a) or plasminogen, was selected from the amino acid sequence of apolipoprotein (a).

(1) The 4,529-amino acid sequence of apolipoprotein (a) [J. W. McLean et al., Nature, 330, 132–137(1987)] was examined to find out a sequence repeated as many times as possible. Thus, there was selected an amino acid sequence composed of 120 amino acids and represented by SEQ ID NO:7 in the List of Sequences, which is a Kringle structure portion repeated 28 times in the sequence extending from the 110th serine to the 3,306th threonine as counted from the N-terminus of apolipoprotein (a).

(2) Employing cysteine residues as main criteria, this amino acid sequence represented by SEQ ID NO:7 was divided into 7 segments: segment 1 extending from the 3rd alanine to the 14th cysteine as counted from the N-terminus, segment 2 extending from the 15th tyrosine to the 35th cysteine, segment 3 extending from the 36th glutamine to the 63rd cysteine, segment 4 extending from the 64th arginine to the 74th cysteine, segment 5 5 extending from the 75th tyrosine to the 86th cysteine, segment 6 extending from the 87th asparagine to the 91st cysteine, and segment 7 extending from the 92nd serine to the 116th glutamine.

In order to learn the nature of these seven segments, the 120-amino acid sequence represented by SEQ ID NO:7 was investigated in various ways. This was accomplished in the same manner as described in steps (3) to (7) of Example 1.

(8) As a result of examination of the foregoing data, it was thought that segment 2 is very likely to assume a b-structure which is a special stereostructure, and segment 5 is very likely to be buried in the interior of the protein molecule because of its high degree of hydrophobicity. Accordingly, the amino acid sequences of these two segments were considered to be unsuitable for use as amino acid sequences specifically representing the antigenicity as an antibody-producing immunogen or the like.

Moreover, segment 6 is not suitable for use as an amino acid sequence specifically representing antigenicity because a sugar is linked thereto, and segment 3 cannot be used because its amino acid sequence has high homology with the amino acid sequence of plasminogen.

(9) Accordingly, it was concluded that the present amino acid sequence specifically representing the antigenicity of apolipoprotein (a) should preferably selected from segment 1, segment 4 and segment 7. As a result of close investigation made so as to minimize homology with the amino acid sequence of plasminogen, the amino acid sequences represented by SEQ ID NO:1, SEQ ID NO:2 and SEQ ID NO:3 in the List of Sequences were selected as candidates.

(10) Using a Model 430A peptide synthesizer (manufactured by Applied Biosystems) according to its instruction manual, peptides including each of these amino acid sequences represented by SEQ ID NO:1, SEQ ID NO:2 and SEQ ID NO:3 in the List of Sequences were synthesized by the t-butoxycarbonylamino acid solid-phase method.

(11) The peptides so synthesized were combined with a carrier comprising keyhole limpet hemocyanin (KLH) (manufactured by Calbiochem) to prepare antibody-producing immunogens. Then, female BALB/c mice (Charles River Japan Inc.) aged 8 weeks were immunized with these immunogens to prepare polyclonal antibodies.

(12) The reactivity of these polyclonal antibodies with lipoprotein (a) was tested by the western blot technique using a Titan Gel Lipoprotein Electrophoresis Kit (manufactured by Helena Laboratory) and a Nova Blot Electrophoretic Transfer Kit (manufactured by Pharmacia-LKB), with the result that the polyclonal antibody prepared from the peptide including the amino acid sequences represented by SEQ ID NO:3 in the List of Sequences did not react with lipoprotein (a).

(13) At the same time, the reactivity of these polyclonal antibodies with apolipoprotein (a) was tested by the western blot technique using 4% SDS-polyacrylamide gel (manufactured by Tefco) and a Nova Blot Electrophoretic Transfer Kit (manufactured by Pharmacia-LKB). Thus, it was found that all of these antibodies reacted with apolipoprotein (a).

(14) Accordingly, the amino acid sequence represented by SEQ ID NO:3 in the List of Sequences was selected as the resent amino acid sequence specifically representing the antigenicity of apolipoprotein (a), which is characterized by having specificity as apolipoprotein (a) and no antigenicity as lipoprotein (a) or plasminogen.

EXAMPLE 3

Synthesis of the peptide represented by SEQ ID NO:8 in the List of Sequences

The peptide represented by SEQ ID NO:8 in the List of Sequences, which is a peptide including the amino acid sequence represented by SEQ ID NO:1 in the List of Sequences, was synthesized.

First of all, using a Model 430A peptide synthesizer (manufactured by Applied Biosystems) according to its instruction manual, the peptide was synthesized by the t-butoxycarbonylamino acid solid-phase method. The synthesized peptide was desorbed from the resin by the hydrogen fluoride method in the presence of dimethyl sulfide, p-thiocresol, m-cresol and anisole used as scavengers for suppressing side reactions.

Thereafter, the scavengers were extracted with dimethyl ether, and the synthesized peptide was extracted with 2N acetic acid.

The extract was purified by anion exchange column chromatography using the anion exchange resin DOWEX 1-X2, and the pattern of a main peak was confirmed by high-performance liquid chromatography (HPLC) using an octadecyl (ODS) column.

After the resulting peptide solution was concentrated by freeze-drying in an evaporator, the peptide was purified and separated by HPLC. The apparatus and conditions employed for this purification by HPLC were as follows: Using the reverse phase ODS column YMC-D-ODS-5 (20 mm×300 mm; manufactured by Yamamura Chemical Laboratory), the peptide was eluted with a gradient of 0% to 70% acetonitrile in 0.1% trifluoroacetic acid (TFA) at a flow rate of 7.0 ml/min. by means of a TWINCLE pump (manufactured by Jasco Corp.) and a Model GP-A40 gradienter (manufactured by Jasco Corp.) and detected by means of a Model UVIDEC-100V detector (210 nm, 1.28 AUFS; manufactured by Jasco Corp.).

The synthetic peptide purified and separated in this manner was concentrated by freeze-drying in an evaporator.

The purity of the resulting synthetic peptide was analyzed by HPLC. The apparatus and conditions employed for this purpose were as follows: Using the reverse phase ODS column YMC-R-ODS-5 (4.9 mm×300 mm; manufactured by Yamamura Chemical Laboratory), the peptide was eluted with a gradient of 0% to 70% acetonitrile in 0.1% trifluoroacetic acid (TFA) at a flow rate of 1.0 ml/min. for 25 minutes by means of a 58-59TWINCLE pump (manufactured by Jasco Corp.) and a Model GP-A40 gradienter (manufactured by Jasco Corp.) and detected by means of a Model UVIDEC-100V detector (210 nm, 1.28 AUFS; manufactured by Jasco Corp.).

Figure 5:
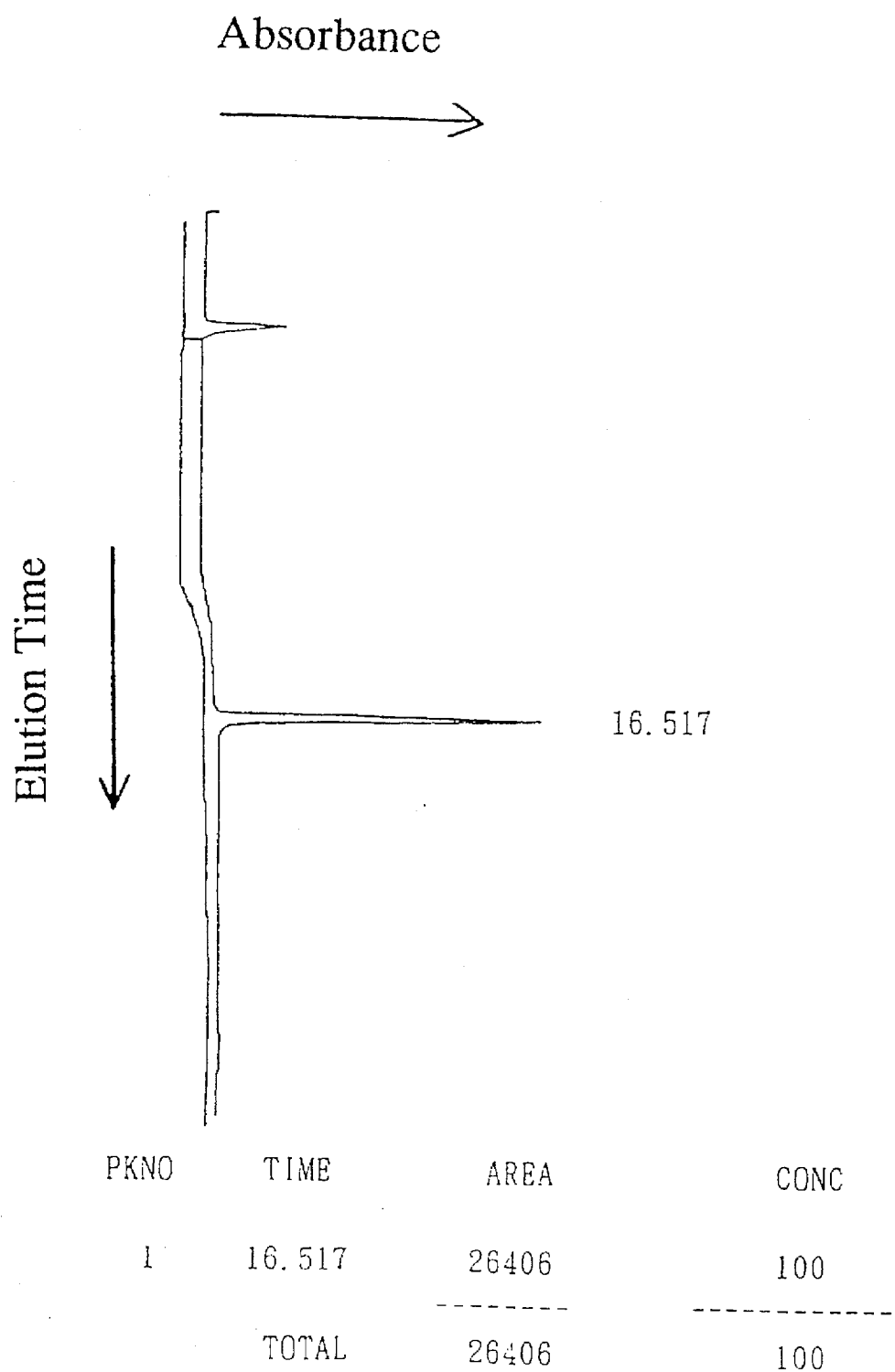
FIG. 5 shows the results of analysis of the synthetic peptide obtained in Example 3 by high-performance liquid chromatography (HPLC).

The results of this analysis are shown in FIG. 5. In FIG. 5, PKNO designates the number of each peak in the chart, TIME designates the elution time, AREA designates the peak area, and CONC designates the proportion of that peak area to the total peak area (i.e., the percent concentration).

It can be seen from these results that the purity of the resulting synthetic peptide is 100%.

Moreover, the amino acid composition analysis of the resulting synthetic peptide was made by using a Waters Pico-Tag amino acid analyzer (manufactured by Millipore) according to its instruction manual. The peptide sample was hydrolyzed by boiling in 6N hydrochloric acid containing 1% phenol at 150° C. for an hour.

The results of this amino acid composition analysis are shown in Table 1. (Since cysteine cannot be determined by hydrolysis with hydrochloric acid, its analytical value is omitted.)

TABLE 1

| Amino acid | Number of amino acid residues in synthesized peptide | |
|---|---|---|
| residue | Theoretical value | Found value |
| Asx | 1 | 1.0 |
| Glx | 1 | 1.0 |
| Ser | 1 | 0.9 |
| Gly | 1 | 1.0 |
| Thr | 1 | 1.0 |
| Ala | 2 | 2.0 |
| Val | 1 | 1.1 |

In Table 1, Asx designates asparagine or aspartic acid, and Glx designates glutamine or glutamic acid.

Figure 6:
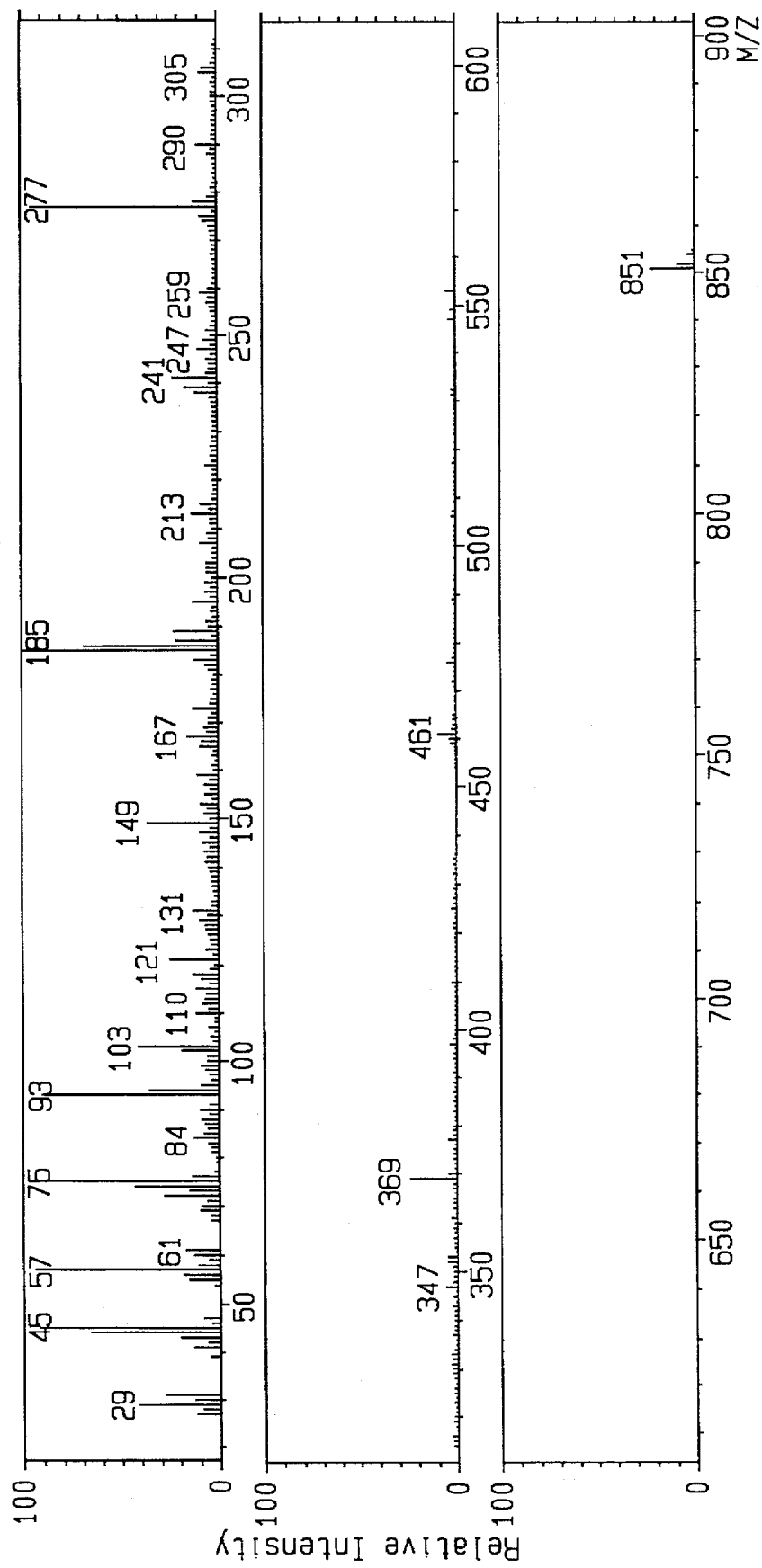
FIG. 6 shows the mass spectrum of the synthetic peptide obtained in Example 3.

From these results, it has been confirmed that the resulting synthetic peptide has the same composition as the amino acid sequence represented by SEQ ID NO:8 in the List of Sequences and, therefore, is the peptide represented by SEQ ID NO:8 in the List of Sequences. The resulting synthetic peptide had an isoelectric point of 2.9. Its mass spectrum is shown in FIG. 6.

EXAMPLE 4

Synthesis of the peptide represented by SEQ ID NO:9 in the List of Sequences

The peptide represented by SEQ ID NO:9 in the List of Sequences, which is a peptide including the amino acid sequence represented by SEQ ID NO:2 in the List of Sequences, was synthesized.

Synthesis, purification and analysis were carried out in the same manner as in Example 3.

Figure 7:
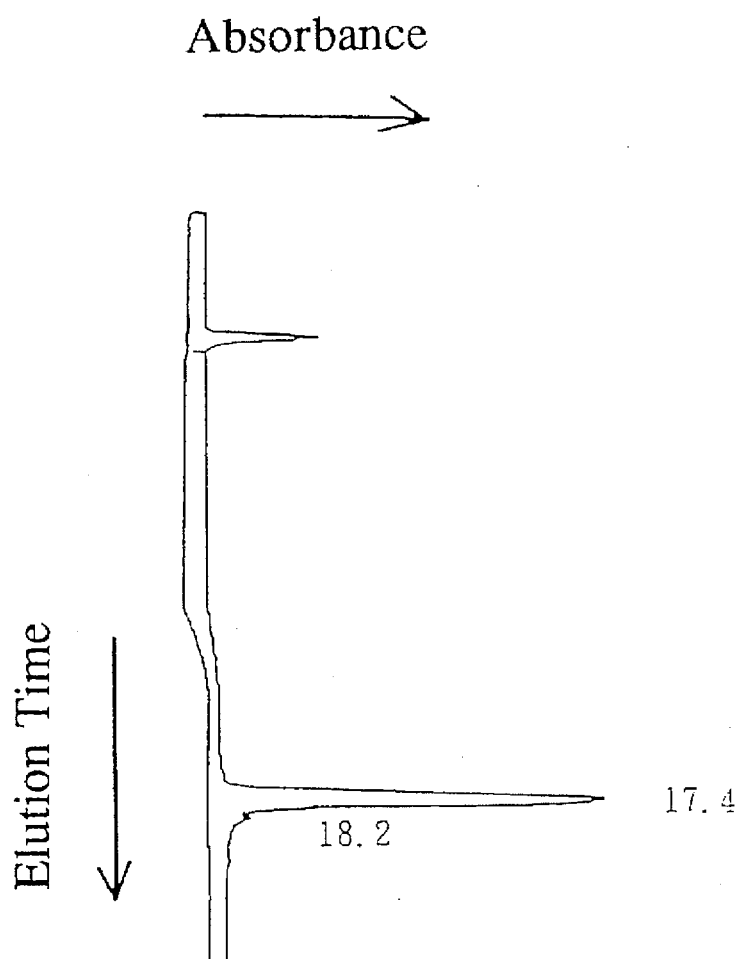
FIG. 7 shows the results of analysis of the synthetic peptide obtained in Example 4 by HPLC.

The purity of the resulting synthetic peptide was analyzed by HPLC and the results thus obtained are shown in FIG. 7.

In FIG. 7, PKNO designates the number of each peak in the chart, TIME designates the elution time, AREA designates the peak area, and CONC designates the proportion of that peak area to the total peak area (i.e., the percent concentration).

It can be seen from these results that the purity of the resulting synthetic peptide is approximately 100%.

Moreover, the results of amino acid composition analysis of the resulting synthetic peptide are shown in Table 2.

TABLE 2

| Amino acid | Number of amino acid residues in synthesized peptide | |
|---|---|---|
| residue | Theoretical value | Found value |
| Glx | 5 | 4.8 |
| Ser | 1 | 1.0 |
| Arg | 1 | 1.1 |
| Thr | 1 | 1.0 |
| Ala | 2 | 2.0 |
| Pro | 2 | 2.1 |

In Table 2, Glx designates glutamine or glutamic acid.

Figure 8:
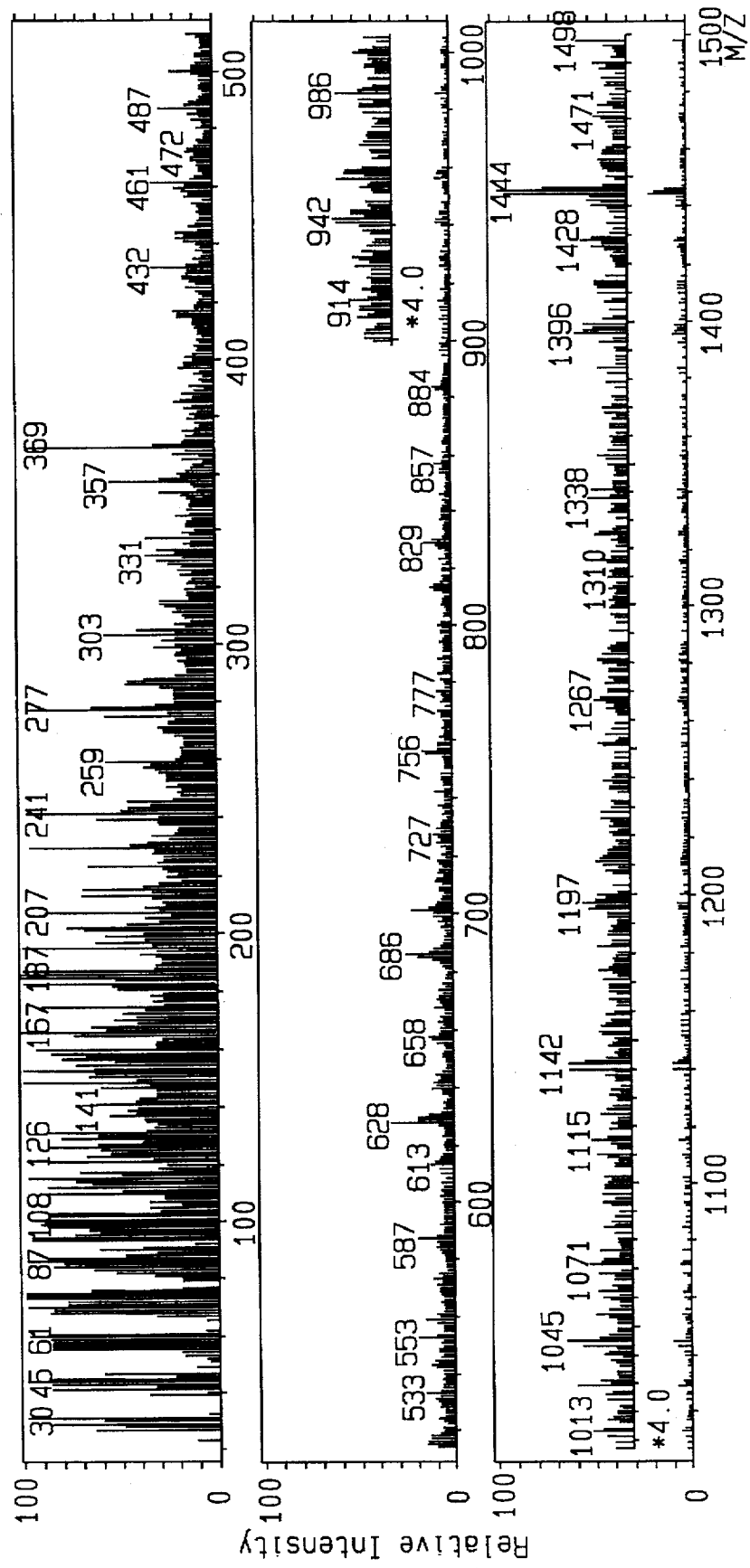
FIG. 8 shows the mass spectrum of the synthetic peptide obtained in Example 4.

From these results, it has been confirmed that the resulting synthetic peptide has the same composition as the amino acid sequence represented by SEQ ID NO:9 in the List of Sequences and, therefore, is the peptide represented by SEQ ID NO:9 in the List of Sequences. The resulting synthetic peptide had an isoelectric point of 4. its mass spectrum is shown in FIG. 8.

EXAMPLE 5

Synthesis of the peptide represented by SEQ ID NO:10 in the List of Sequences

The peptide represented by SEQ ID NO:10 in the List of Sequences, which is a peptide including the amino acid sequence represented by SEQ ID NO:3 in the List of Sequences, was synthesized.

Synthesis, purification and analysis were carried out in the same manner as in Example 3.

Figure 9:
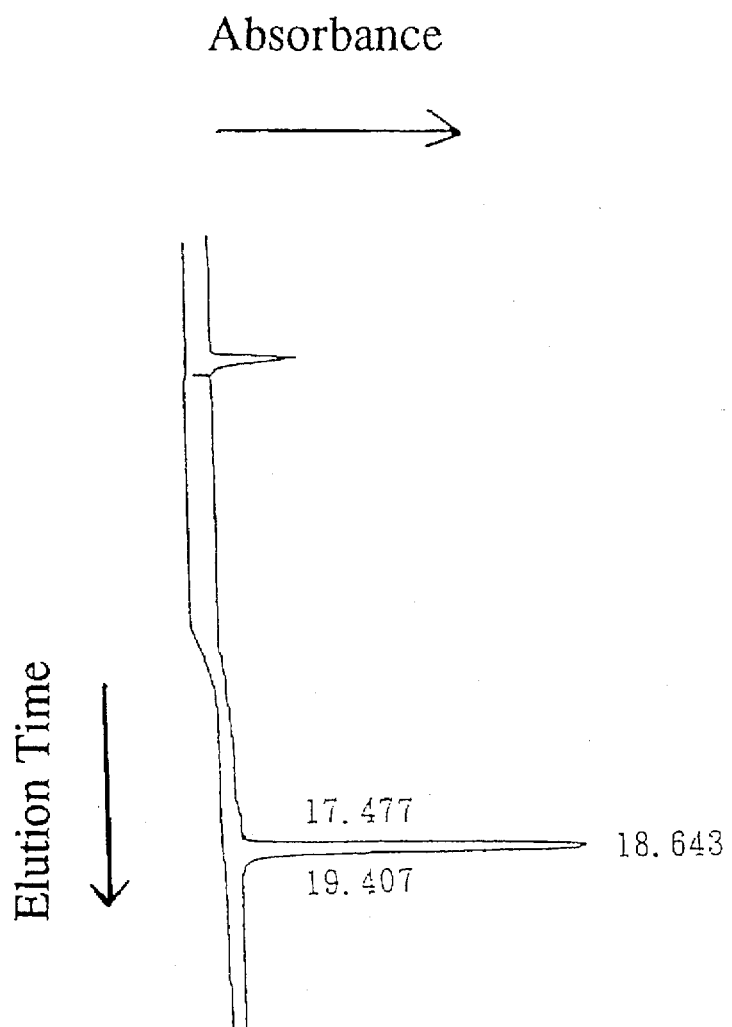
FIG. 9 shows the results of analysis of the synthetic peptide obtained in Example 5 by HPLC.

The purity of the resulting synthetic peptide was analyzed by HPLC and the results thus obtained are shown in FIG. 9.

In FIG. 9, PKNO designates the number of each peak in the chart, TIME designates the elution time, AREA designates the peak area, and CONC designates the proportion of that peak area to the total peak area (i.e., the percent concentration).

It can be seen from these results that the purity of the resulting synthetic peptide is approximately 100%.

Moreover, the results of amino acid composition analysis of the resulting synthetic peptide are shown in Table 3.

TABLE 3

| Amino acid residue | Number of amino acid residues in synthesized peptide | |
|---|---|---|
| | Theoretical value | Found value |
| Asx | 2 | 2.0 |
| Arg | 1 | 1.0 |
| Ala | 3 | 2.7 |
| Pro | 2 | 2.0 |
| Val | 1 | 1.0 |

In Table 3, Asx designates asparagine or aspartic acid.

Figure 10:
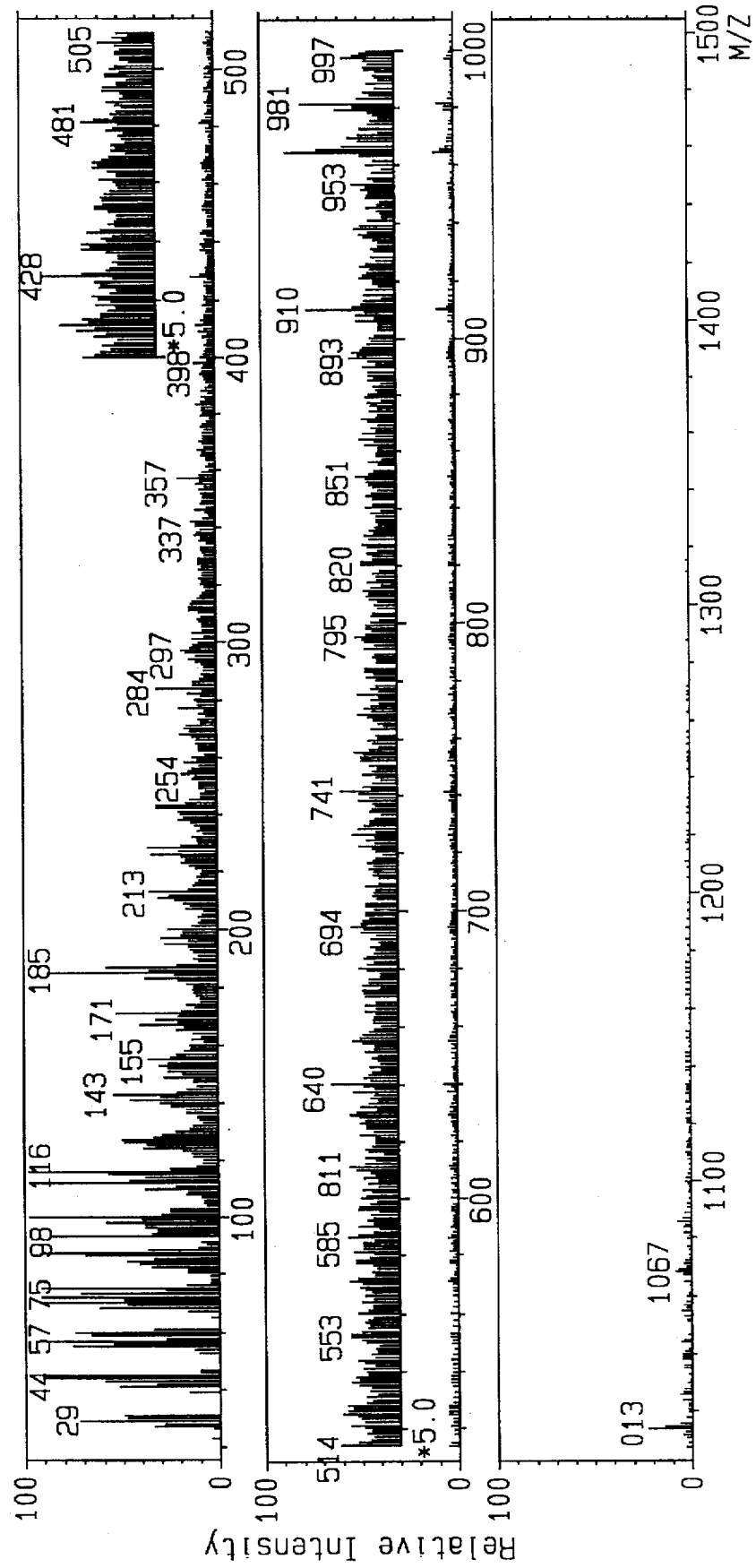
FIG. 10 shows the mass spectrum of the synthetic peptide obtained in Example 5.

From these results, it has been confirmed that the resulting synthetic peptide has the same composition as the amino acid sequence represented by SEQ ID NO:10 in the List of Sequences and, therefore, is the peptide represented by SEQ ID NO:10 in the List of Sequences. The resulting synthetic peptide had an isoelectric point of 5. Its mass spectrum is shown in FIG. 10.

EXAMPLE 6
Preparation of an antibody-producing immunogen comprising a carrier having combined therewith the peptide represented by SEQ ID NO:8 in the List of Sequences 10 mg of a carrier comprising keyhole limpet hemocyanin (KLH) (manufactured by Calbiochem) or bovine serum albumin (BSA) (manufactured by Seikagaku Corp.) was dissolved in 10 mM potassium dihydrogen phosphate-dipotassium hydrogen phosphate buffer (pH 7.0), to which was added 150 µl of a 2.5% solution of maleimidobenzoyl-N-hydroxysuccinimideester (MBS) (manufactured by Pierce) in N,N-dimethylformamide. This mixture was reacted at room temperature for 30 minutes with stirring.

This mixture was applied to a gel filtration column of Sephadex G-25 (manufactured by Pharmacia-LKB) which was placed at 4° C. and had been equilibrated with 10 mM potassium dihydrogen phosphate-dipotassium hydrogen phosphate buffer (pH 7.0), and a combined MBS-carrier component was collected by monitoring the absorbance at 280 nm.

This combined MBS-carrier component was adjusted to pH 7.0 with trisodium phosphate, and the peptide synthesized in Example 3 and represented by SEQ ID NO:8 in the List of Sequences was added thereto and mixed therewith. This mixture was reacted for 150 minutes.

After completion of the reaction, the mixture was dialyzed three times against water and then freeze-dried to obtain an antibody-producing immunogen comprising a carrier having combined therewith the peptide represented by SEQ ID NO:8 in the List of Sequences.

The yield was 89% when the carrier was KLH, and 67% when the carrier was BSA.

The proportion (weight ratio) of the peptide represented by SEQ ID NO:8 in the List of Sequences to the antibody-producing immunogen was 33% when the carrier was KLH, and 27% when the carrier was BSA.

EXAMPLE 7
Preparation of an antibody-producing immunogen comprising a carrier having combined therewith the peptide represented by SEQ ID NO:9 in the List of Sequences Using the peptide synthesized in Example 4, an antibody-producing immunogen comprising a carrier having combined therewith the peptide represented by SEQ ID NO:9 in the List of Sequences was prepared in the same manner as in Example 6.

The yield was 73% when the carrier was KLH, and 64% when the carrier was BSA.

The proportion (weight ratio) of the peptide represented by SEQ ID NO:9 in the List of Sequences to the antibody-producing immunogen was 23% when the carrier was KLH, and 25% when the carrier was BSA.

EXAMPLE 8
Preparation of an antibody-producing immunogen comprising a carrier having combined therewith the peptide represented by SEQ ID NO:10 in the List of Sequences Using the peptide synthesized in Example 5, an antibody-producing immunogen comprising a carrier having combined therewith the peptide represented by SEQ ID NO:10 in the List of Sequences was prepared in the same manner as in Example 6.

The yield was 75% when the carrier was KLH, and 52% when the carrier was BSA.

The proportion (weight ratio) of the peptide represented by SEQ ID NO:10 in the List of Sequences to the antibody-producing immunogen was 30% when the carrier was KLH, and 21% when the carrier was BSA.

EXAMPLE 9
Preparation of a mouse polyclonal antibody to lipoprotein (a) specifically recognizing the amino acid sequence represented by SEQ ID NO:i in the List of Sequences The antibody-producing immunogen (having KLH as the carrier) obtained in Example 6 was dissolved in physiological saline (a 0.9% aqueous solution of sodium chloride) so as to give a concentration of 360 µg/ml. This solution was mixed with an equal amount of Freund's complete adjuvant to form an emulsion, and 0.5 ml of this emulsion was subcutaneously injected into the abdomen of a female BALB/c mouse (Charles River Japan Inc.) aged 8 weeks for purposes of immunization.

Two weeks after the initial immunization, the above-described antibody-producing immunogen was dissolved in physiological saline so as to give a concentration of 180 µg/ml. This solution was mixed with an equal amount of Freund's incomplete adjuvant to form an emulsion, and 0.5 ml of this emulsion was injected as a booster. This booster injection was repeated at intervals of 2 weeks.

The antibody titer in the blood serum of this mouse, which was an immunized animal, was measured by an enzyme immunoassay (ELISA, EIA) at intervals of one week.

This ELISA was carried out as follows: The antibody-producing immunogen (having BSA as the carrier) obtained in Example 6 was converted into a solid phase on a microplate, and blood serum obtained from the immunized animal was added to the microplate to effect reaction. After washing, peroxidase (POD)-labeled anti-mouse IgG antibody was added to the microplate to effect reaction. After washing, a color-producing solution containing hydrogen peroxide and 2,2'-azino-bis(3-ethylbenzthiazoline-6-sulfonic acid) (ABTS) was added to the microplate to develop color. Then, the antibody titer was determined by measuring the absorbance at 415 nm on an EIA plate reader (manufactured by Bio-Rad).

After a total of five booster injections were given, it was noted that the antibody titer reached a plateau. Accordingly, exsanguination was performed and blood serum was separated to obtain 1.2 ml of antiserum.

This antiserum was centrifuged at 10,000 r.p.m. for 30 minutes to remove any insoluble matter, and then salted-out at 20° C. by adding 0.18 g of sodium sulfate per ml of antiserum.

The resulting precipitate fraction of immunoglobulin was dissolved in the least possible amount of 17.5 mM sodium dihydrogen phosphate-disodium hydrogen phosphate buffer (pH 6.3) and then dialyzed thoroughly against this 17.5 mM sodium dihydrogen phosphate-disodium hydrogen phosphate buffer (pH 6.3).

After completion of the dialysis, the dialyzed solution was passed through a DEAE-cellulose ion exchange column (manufactured by Serva) which had been equilibrated with 17.5 mM sodium dihydrogen phosphate-disodium hydrogen phosphate buffer (pH 6.3). By collecting the flow-through fractions, there was obtained a mouse polyclonal antibody to lipoprotein (a) specifically recognizing the amino acid sequence represented by SEQ ID NO:1 in the List of Sequences.

The amount of the antibody thus obtained was 1.0 mg as expressed in terms of protein.

Reference Example 1
Reactivity of the polyclonal antibody to lipoprotein (a) obtained in Example 9 with the peptide represented by SEQ ID NO:8 in the List of Sequences The reactivity of the polyclonal antibody to lipoprotein (a) obtained in Example 9 with the peptide represented by SEQ ID NO:8 in the List of Sequences, which is a peptide including the amino acid sequence represented by SEQ ID NO:i in the List of Sequences, was confirmed by ELISA.

(1) The antibody-producing immunogen (having BSA as the carrier) obtained in Example 6 was dissolved in physiological saline (a 0.9% aqueous solution of sodium chloride) so as to give a concentration of 5 µg/ml. This solution was added to wells of a 96-well microplate (manufactured by Nunc) in an amount of 100 µl per well and allowed to stand at 37° C. for 2 hours to convert the peptide into a solid phase.

(2) After this microplate was washed with a washing solution [phosphate-buffered physiological saline [5.59 mM disodium hydrogen phosphate, 1.47 mM potassium dihydrogen phosphate, 137 mM sodium chloride, 2.68 mM potassium chloride (pH 7.2)] containing 0.05% Tween 20], 10 mM potassium dihydrogen phosphate-dipotassium hydrogen phosphate buffer (pH 7.2) containing 1% BSA was added to the wells thereof in an amount of 300 µl per well and allowed to stand at 37° C. for 2 hours to effect blocking. Thereafter, the microplate was washed again with the washing solution.

(3) The polyclonal antibody to lipoprotein (a) obtained in Example 9 was dissolved in phosphate-buffered physiological saline containing 3% BSA so as to give a concentration of 60 µg/ml, and then serial-diluted 2- to 2,048-fold with phosphate-buffered physiological saline containing 3% BSA to prepare a series of dilutions. These dilutions were separately added to the wells of the microplate in an amount of 100 µl per well and allowed to stand at 37° C. for 2 hours to effect reaction. Thereafter, the microplate was washed with the washing solution.

(4) As a control, blood serum obtained from an unimmunized mouse was diluted 200-fold with phosphate-buffered physiological saline containing 3% BSA, and then serial-diluted 2- to 2,048-fold with phosphate-buffered physiological saline containing 3% BSA to prepare a series of dilutions. These dilutions were separately added to the wells of another microplate as obtained from step (2) in an amount of 100 µl per well and allowed to stand at 37° C. for 2 hours to effect reaction. Thereafter, the microplate was washed with the washing solution.

(5) Peroxidase (POD)-labeled anti-mouse IgG antibody (manufactured by Amersham) was diluted 2,000-fold with phosphate-buffered physiological saline containing 3% BSA, added to the wells of the microplates obtained from steps (3) and (4) in an amount of 100 µl per well, and allowed to stand at 37° C. for 2 hours to effect reaction.

(6) After these microplates were washed with the washing solution, a peroxidase reaction solution (prepared by adding 2 µl of 1.7% hydrogen peroxide to 1 ml of 50 mM disodium hydrogen phosphate-24 mM citric acid buffer containing 3 mM o-phenylenediamine, immediately before use) was added to the wells thereof in an amount of 100 µl per well and reacted at room temperature. After 15 minutes, 6N sulfuric acid was added in an amount of 50 µl per well to stop the reaction.

(7) The absorbances at 492 nm of the wells of these microplates were measured on an EIA plate reader (manufactured by Bio-Rad).

Figure 11:
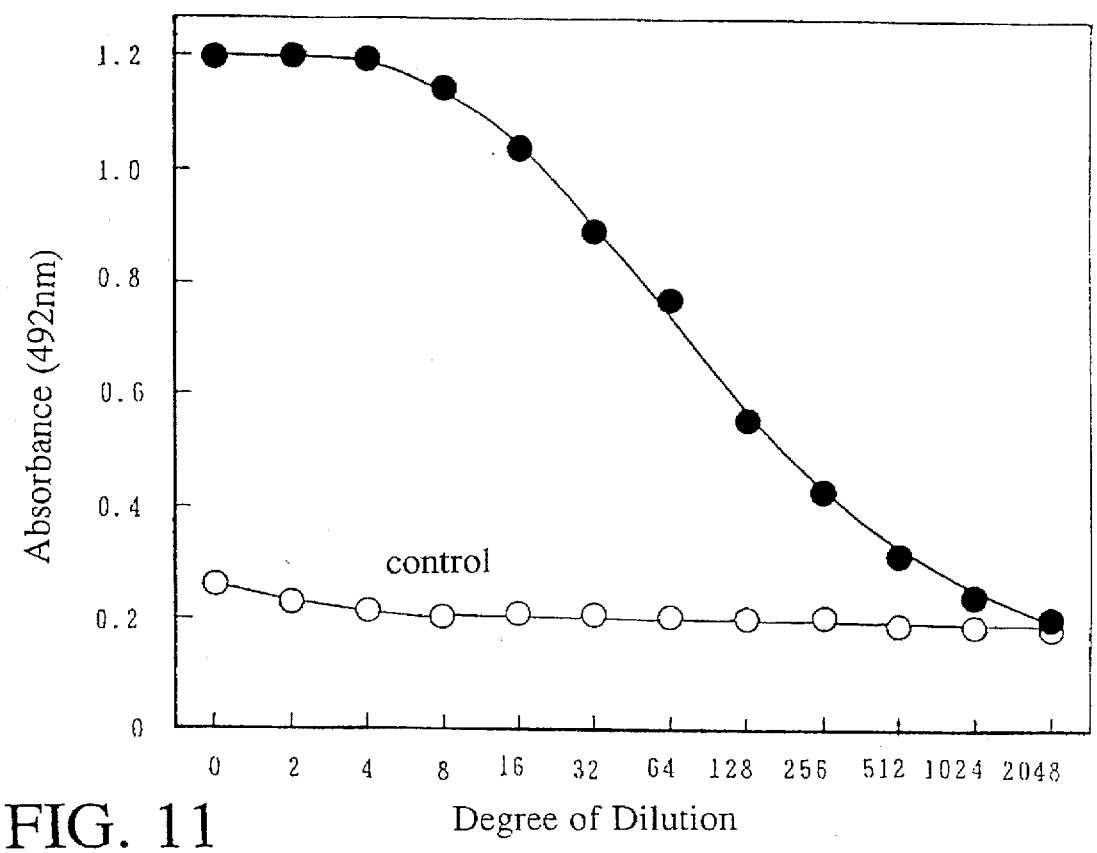
FIG. 11 shows the results of ELISA carried out to examine the reactivity of the polyclonal antibody to lipoprotein (a) obtained in Example 9 with the peptide represented by SEQ ID NO:8 in the List of Sequences.

The results of these measurements are shown in FIG. 11.

From these results, it has been confirmed that the polyclonal antibody to lipoprotein (a) obtained in Example 9 specifically recognizes and combines with the peptide represented by SEQ ID NO:8 in the List of Sequences which is a peptide including the amino acid sequence represented by SEQ ID NO:1 in the List of Sequences.

EXAMPLE 10
Preparation of a mouse polyclonal antibody to lipoprotein (a) specifically recognizing the amino acid sequence represented by SEQ ID NO:2 in the List of Sequences The preparation of an antibody was carried out in the same manner as in Example 9, except that the antibody-producing immunogen (having KLH as the carrier) obtained in Example 7 was dissolved in physiological saline so as to give a concentration of 500 µg/ml at the time of the initial immunization, the same immunogen was dissolved in physiological saline so as to give a concentration of 250 µg/ml at the time of each booster injection, and the antibody-producing immunogen (having BSA as the carrier) obtained in Example 7 was converted into a solid phase and used to determine the antibody titer. Thus, there was obtained a mouse polyclonal antibody to lipoprotein (a) specifically recognizing the amino acid sequence represented by SEQ ID NO:2 in the List of Sequences.

The amount of the antibody thus obtained was 1.1 mg as expressed in terms of protein.

Reference Example 2
Reactivity of the polyclonal antibody to lipoprotein (a) obtained in Example 10 with the peptide represented by SEQ ID NO:9 in the List of Sequences The reactivity of the polyclonal antibody to lipoprotein (a) obtained in Example 10 with the peptide represented by SEQ ID NO:9 in the List of Sequences, which is a peptide including the amino acid sequence represented by SEQ ID NO:2 in the List of Sequences, was confirmed by ELISA.

Measurements were made in the same manner as in Reference Example 1, except that the polyclonal antibody to lipoprotein (a) obtained in Example 10 was used at the same concentration in place of the polyclonal antibody to lipoprotein (a) obtained in Example 9, and the antibody-producing immunogen (having BSA as the carrier) obtained in Example 7 was used at the same concentration and converted into a solid phase on a microplate in place of the antibody-producing immunogen obtained in Example 6.

Figure 12:
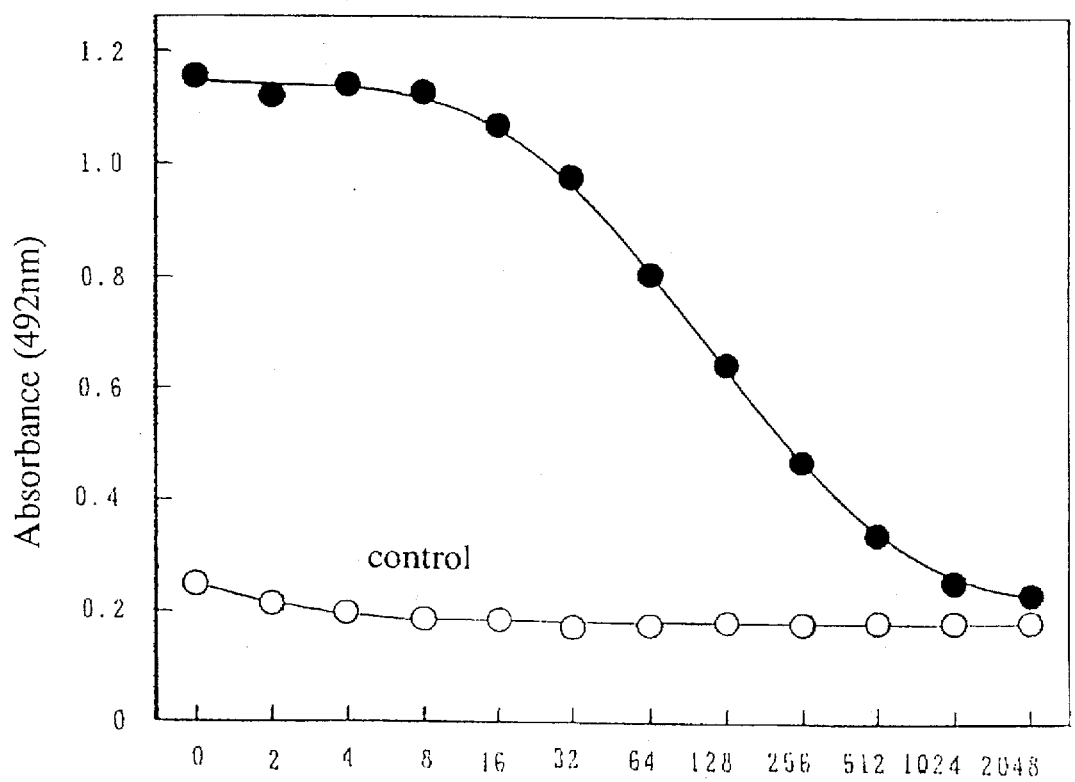
FIG. 12 shows the results of ELISA carried out to examine the reactivity of the polyclonal antibody to lipoprotein (a) obtained in Example 10 with the peptide represented by SEQ ID NO:9 in the List of Sequences.

The results of these measurements are shown in FIG. 12.

From these results, it has been confirmed that the polyclonal antibody to lipoprotein (a) obtained in Example 10 specifically recognizes and combines with the peptide represented by SEQ ID NO:9 in the List of Sequences which is a peptide including the amino acid sequence represented by SEQ ID NO:2 in the List of Sequences.

Reference Example 3
Reactivity with lipoprotein (a) and LDL of the polyclonal antibodies to lipoprotein (a) obtained in Examples 9 and 10

The reactivity with lipoprotein (a) and LDL of each of the polyclonal antibodies to lipoprotein (a) obtained in Examples 9 and 10 was confirmed by the western blot technique.

(1) Human blood serum having a high lipoprotein (a) concentration was ultracentrifuged to separate a fraction having a specific gravity range of 1.05 to 1.12. Then, this serum fraction was subjected to lysine-Sepharose 4B affinity chromatography (manufactured by Pharmacia-LKB). Thus, there was obtained purified lipoprotein (a).

(2) Human blood serum having a high LDL concentration was ultracentrifuged to separate a fraction having a specific gravity range of 1.006 to 1.063. Then, this serum fraction was subjected to affinity chromatography using anti-lipoprotein (a) antibody (manufactured by Immuno) as the ligand. The flow-through fractions were collected to obtain purified LDL.

(3) These lipoprotein (a) and LDL were each dissolved in physiological saline (a 0.9% aqueous solution of sodium chloride) so as to give a concentration of 0.5 mg/ml. 2 µl samples of these solutions were subjected to electrophoresis using a Titan Gel Lipoprotein Electrophoresis Kit (manufactured by Helena Laboratory). The supporting medium was agarose gel. Using a barbital buffer (pH 8.8) as the electrophoresis buffer, a voltage of 90 V was applied for 75 minutes.

(4) Using a Nova Blot Electrophoretic Transfer Kit (manufactured by Pharmacia-LKB), transfer was carried out on a dry basis according to its instruction manual.

(5) The agarose gel obtained from step (3) was placed on a transfer apparatus and a 9 cm×9 cm nitrocellulose membrane (manufactured by Bio-Rad) was laid thereon. Using a transfer buffer comprising 48 mM Tris, 39 mM glycine, 0.0375% (W/V) sodium dodecyl sulfate (SDS) and 20% (V/V) methanol, transfer was carried out by passing an electric current of 65 mA for 2 hours.

(6) The nitrocellulose membrane having undergone the transfer was soaked overnight in 20 ml of phosphate-buffered physiological saline [5.59 mM disodium hydrogen phosphate, 1.47 mM potassium dihydrogen phosphate, 137 mM sodium chloride, 2.68 mM potassium chloride (pH 7.2)] containing 1% BSA at 4° C. to effect blocking.

(7) Then, this nitrocellulose membrane was washed by shaking it in 20 ml of a washing solution (phosphate-buffered physiological saline containing 0.05% Tween 20) for 10 minutes. This procedure was repeated three times.

(8) 80 µg each of the polyclonal antibodies to lipoprotein (a) obtained in Examples 9 and 10 was dissolved in 20 ml of phosphate-buffered physiological saline. Two nitrocellulose membranes as obtained from step (7) were separately soaked in these two solutions at room temperature for 2 hours to effect reaction.

(9) As a control, the procedure described above in step (8) was repeated by using a mixture of sheep anti-lipoprotein (a) antibody (manufactured by Immuno) and goat anti-apolipoprotein B antibody to apolipoprotein B-100 being a component of LDL (manufactured by International Enzyme), both dissolved at the same concentration, in place of the polyclonal antibody to lipoprotein (a) obtained in Examples 9 and 10.

In addition, another nitrocellulose membrane as obtained from step (7), which was not acted on by any of the polyclonal antibodies obtained in Examples 9 and 10, sheep anti-lipoprotein (a) antibody and goat anti-apolipoprotein B antibody, was provided as a negative control.

(10) The nitrocellulose membranes subjected to the procedure described above in step (8) or (9) were washed by shaking them in 20 ml of the washing solution for 10 minutes. This procedure was repeated three times.

(11) Next, peroxidase-labeled anti-mouse IgG antibody (manufacture by Dako), peroxidase-labeled anti-sheep IgG antibody (manufactured by Dako) and peroxidase-labeled anti-goat IgG antibody (manufactured by Dako) were diluted 500-fold with phosphate-buffered physiological saline containing 3% BSA to prepare 20 ml of a solution, and the nitrocellulose membranes were soaked therein at room temperature for 2 hours to effect reaction.

(12) These nitrocellulose membranes were washed by shaking them in 20 ml of the washing solution for 10 minutes. This procedure was repeated three times.

(13) The nitrocellulose membranes obtained from step (12) were soaked in 20 ml of phosphate-buffered physiological saline containing 0.025% 3,3'-diaminobenzidine tetrahydrochloride and 0.01% hydrogen peroxide at room temperature for 15 minutes to develop color.

Figure 13:
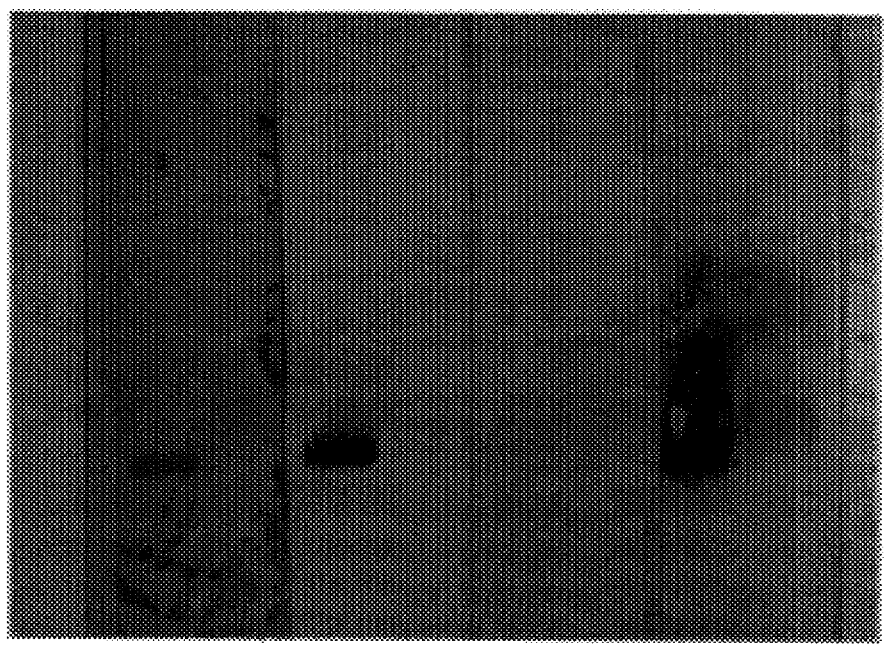
FIG. 13 is a photograph showing electrophoretic patterns observed in the western blot technique carried out to examine the reactivity of the polyclonal antibodies to lipoprotein (a) obtained in Examples 9 and 10 with lipoprotein (a) and LDL.

The results of this western blot technique are shown in FIG. 13.

In FIG. 13, P represents the control, N represents the negative control, and numerals 1 and 2 represent the nitrocellulose membranes acted on by the polyclonal antibodies to lipoprotein (a) obtained in Examples 9 and 10, respectively. In each nitrocellulose membrane, lipoprotein (a) is transferred to the left-hand part and LDL to the right-hand part.

As can be seen from these results, the polyclonal antibodies to lipoprotein (a) obtained in Examples 9 and 10 exhibit color development at the same position as the commercially available anti-lipoprotein (a) antibody does, but no color development at the position where the commercially available anti-apolipoprotein B antibody exhibits color development. Thus, it has been confirmed that these polyclonal antibodies combine specifically with lipoprotein (a) and do not combine with LDL.

Moreover, no color development is observed in the negative control which was not acted on by any of the polyclonal antibodies obtained in Examples 9 and 10, the commercially available anti-lipoprotein (a) antibody and the commercially available anti-apolipoprotein B antibody, indicating that nonspecific color development did not take place.

Reference Example 4

Reactivity with plasminogen of the polyclonal antibodies to lipoprotein (a) obtained in Examples 9 and 10

The reactivity with plasminogen of each of the polyclonal antibodies to lipoprotein (a) obtained in Examples 9 and 10 was confirmed by the western blot technique.

(1) Human blood plasma having a high plasminogen concentration was ultracentrifuged to separate a fraction having a specific gravity of 1.21 or greater. This plasma fraction was subjected to lysine-Sepharose 4B affinity chromatography (manufactured by Pharmacia-LKB) and then to affinity chromatography using anti-lipoprotein (a) antibody (manufactured by Immuno) as the ligand. The flow-through fractions were collected to obtain purified plasminogen.

(2) This plasminogen was dissolved in physiological saline (a 0.9% aqueous solution of sodium chloride) so as to give a concentration of 1.0 mg/ml, and a 10 µl sample of this solution was subjected to electrophoresis. The supporting medium was 3–12% SDS polyacrylamide gel. Using 25 mM Tris-0.19M glycine buffer containing 0.1% SDS as the electrophoresis buffer, an electric current of 20 mA was passed for 120 minutes.

(3) Using a Nova Blot Electrophoretic Transfer Kit (manufactured by Pharmacia-LKB), transfer was carried out on a dry basis according to its instruction manual.

(4) The 3–12% SDS polyacrylamide gel obtained from step (2) was placed on a transfer apparatus and a 9 cm×9 cm nitrocellulose membrane (manufactured by Bio-Rad) was laid thereon. Using a transfer buffer comprising 48 mM Tris, 39 mM glycine, 0.0375% (W/V) sodium dodecyl sulfate (SDS) and 20% (V/V) methanol, transfer was carried out by passing an electric current of 65 mA for 2 hours.

The succeeding procedures were substantially the same as those described in and after step (6) of Reference Example 3. However, it is to be understood that, although a mixture of sheep anti-lipoprotein (a) antibody and goat anti-apolipoprotein B antibody was used as a control in step (9) of Reference Example 3, goat anti-plasminogen antibody (manufactured by Medical Biological Laboratory) was used at the same concentration in this reference example.

Figure 14:
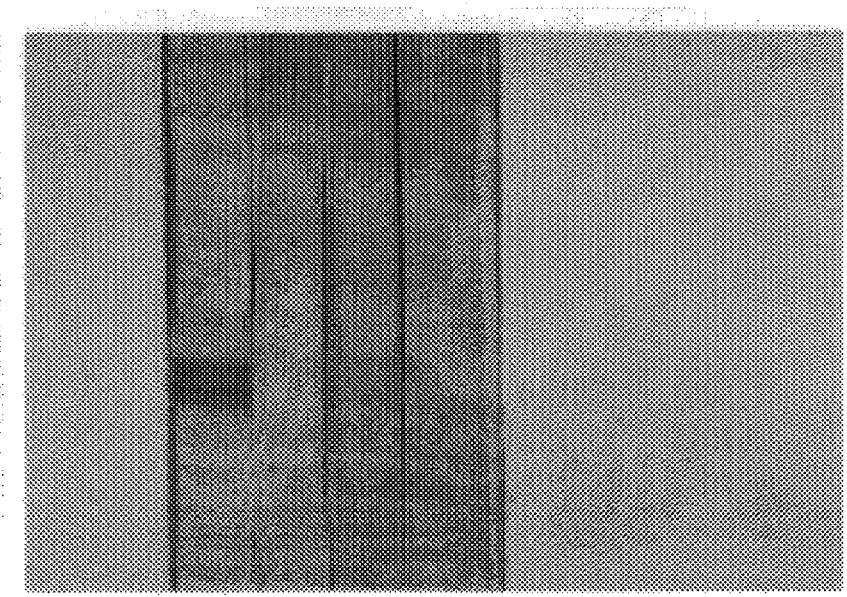
FIG. 14 is a photograph showing electrophoretic patterns observed in the western blot technique carried out to examine the reactivity of the polyclonal antibodies to lipoprotein (a) obtained in Examples 9 and 10 with plasminogen.

The results of this western blot technique are shown in FIG. 14.

In FIG. 14, P represents the control, N represents the negative control, and numerals 1 and 2 represent the nitrocellulose membranes acted on by the polyclonal antibodies to lipoprotein (a) obtained in Examples 9 and 10, respectively.

As can be seen from these results, the polyclonal antibodies to lipoprotein (a) obtained in Examples 9 and 10 exhibit no color development at the position where the commercially available anti-plasminogen B antibody exhibits color development. Thus, it has been confirmed that these polyclonal antibodies do not combine with plasminogen.

Moreover, no color development is observed in the negative control which was not acted on by the polyclonal antibodies obtained in Examples 9 and 10 or the like, indicating that nonspecific color development did not take place.

EXAMPLE 11

Preparation of a mouse polyclonal antibody to apolipoprotein (a) specifically recognizing the amino acid sequence represented by SEQ ID NO:3 in the List of Sequences The preparation of an antibody was carried out in the same manner as in Example 9, except that the antibody-producing immunogen (having KLH as the carrier) obtained in Example 8 was dissolved in physiological saline so as to give a concentration of 400 µg/ml at the time of the initial immunization, the same immunogen was dissolved in physiological saline so as to give a concentration of 200 µg/ml at the time of each booster injection, and the antibody-producing immunogen (having BSA as the carrier) obtained in Example 8 was converted into a solid phase and used to determine the antibody titer. Thus, there was obtained a mouse polyclonal antibody to apolipoprotein (a) specifically recognizing the amino acid sequence represented by SEQ ID NO:3 in the List of Sequences.

The amount of the antibody thus obtained was 1.0 mg as expressed in terms of protein.

Reference Example 5

Reactivity of the polyclonal antibody to apolipoprotein (a) obtained in Example 11 with the peptide represented by SEQ ID NO:10 in the List of Sequences The reactivity of the polyclonal antibody to apolipoprotein (a) obtained in Example 11 with the peptide represented by SEQ ID NO:10 in the List of Sequences, which is a peptide including the amino acid sequence represented by SEQ ID NO:3 in the List of Sequences, was confirmed by ELISA.

Measurements were made in the same manner as in Reference Example 1, except that the polyclonal antibody to apolipoprotein (a) obtained in Example 11 was used at the same concentration in place of the polyclonal antibody to lipoprotein (a) obtained in Example 9, and the antibody-producing immunogen (having BSA as the carrier) obtained in Example 8 was used at the same concentration and converted into a solid phase on a microplate in place of the antibody-producing immunogen obtained in Example 6.

Figure 15:
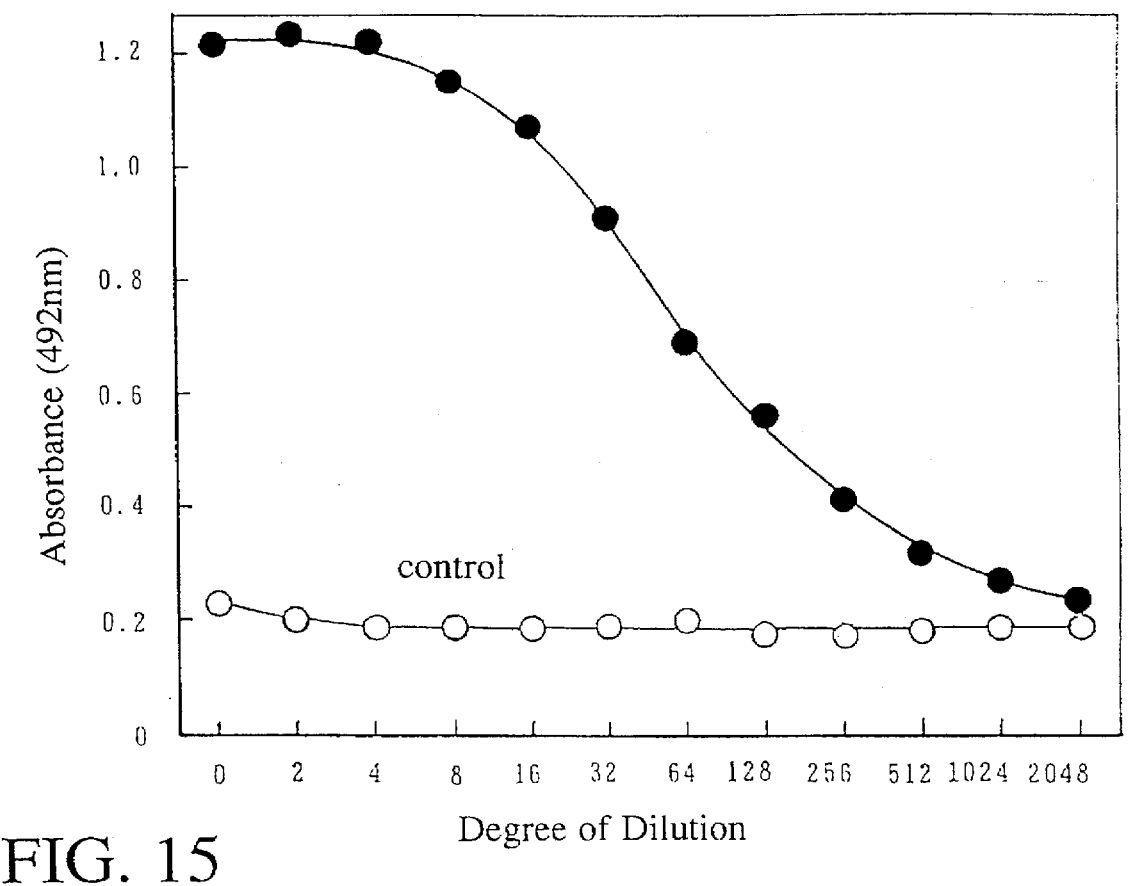
FIG. 15 shows the results of ELISA carried out to examine the reactivity of the polyclonal antibody to apolipoprotein (a) obtained in Example 11 with the peptide represented by SEQ ID NO:10 in the List of Sequences.

The results of these measurements are shown in FIG. 15.

From these results, it has been confirmed that the polyclonal antibody to apolipoprotein (a) obtained in Example 11 specifically recognizes and combines with the peptide represented by SEQ ID NO:10 in the List of Sequences which is a peptide including the amino acid sequence represented by SEQ ID NO:3 in the List of Sequences.

Reference Example 6

Reactivity with apolipoprotein (a) of the polyclonal antibody to apolipoprotein (a) obtained in Example 11

The reactivity with apolipoprotein (a) of the polyclonal antibody to apolipoprotein (a) obtained in Example 11 was confirmed by the western blot technique.

(1) Four types of human blood sera having a high lipoprotein (a) concentration were ultracentrifuged to separate a fraction having a specific gravity range of 1.05 to 1.12. Then, the resulting serum fractions were subjected to lysine-Sepharose 4B affinity chromatography (manufactured by Pharmacia-LKB). Thus, there were obtained four types of purified lipoprotein (a).

Then, these four types of purified lipoprotein (a) were treated by the addition of 1 mM dithiothreitol and ultracentrifuged again to separate a fraction having a specific gravity of 1.21 or greater. Thus, the low-density lipoprotein (LDL) moiety was removed to obtain four types of purified apolipoprotein (a).

(2) These four types of purified apolipoprotein (a) were each dissolved in a sample buffer [10 mM Tris, 1% sodium dodecyl sulfate (SDS) (pH 6.80)] so as to give a concentration of 0.5 mg/ml. 2 µl samples of these solutions were subjected to SDS polyacrylamide gel electrophoresis using 4% SDS polyacrylamide gel (manufactured by Tefco). Using a buffer (pH 8.64) comprising 40 mM Tris, 40 mM boric acid and 0.1% sodium dodecyl sulfate (SDS) as the cathode-side buffer and 0.43M Tris buffer (pH 9.18) as the anode-side buffer, an electric current of 20 mA was passed for 75 minutes.

(3) Using a Nova Blot Electrophoretic Transfer Kit (manufactured by Pharmacia-LKB), transfer was carried out on a dry basis according to its instruction manual.

(4) The 4% SDS polyacrylamide gel obtained from step (2) was placed on a transfer apparatus and a 9 cm×9 cm nitrocellulose membrane (manufactured by Bio-Rad) was laid thereon. Using a transfer buffer comprising 48 mM Tris, 39 mM glycine, 0.0375% (W/V) SDS and 20% (V/V) methanol, transfer was carried out by passing an electric current of 65 mA for 2 hours.

(5) The nitrocellulose membrane having undergone the transfer was soaked overnight in 20 ml of phosphate-buffered physiological saline [5.59 mM disodium hydrogen phosphate, 1.47 mM potassium dihydrogen phosphate, 137 mM sodium chloride, 2.68 mM potassium chloride (pH 7.2)] containing 1% BSA at 4° C. to effect blocking.

(6) Then, this nitrocellulose membrane was washed by shaking it in 20 ml of a washing solution (phosphate-buffered physiological saline containing 0.05% Tween 20) for 10 minutes. This procedure was repeated three times.

(7) 80 µg of the polyclonal antibody to apolipoprotein (a) obtained in Example 11 was dissolved in 20 ml of phosphate-buffered physiological saline. The nitrocellulose membrane subjected to the procedure described in step (6)

was soaked in this solution at room temperature for 2 hours to effect reaction.

(8) As a control, the procedure described above in step (7) was repeated by using sheep anti-lipoprotein (a) antibody (manufactured by Immuno) reacting with apolipoprotein (a), dissolved at the same concentration, in place of the polyclonal antibody to apolipoprotein (a) obtained in Examples 11. In addition, another nitrocellulose membrane as obtained from step (6), which was not acted on by either of the polyclonal antibody to apolipoprotein (a) obtained in Examples 11 and sheep anti-lipoprotein (a) antibody, was provided as a negative control.

(9) The nitrocellulose membranes subjected to the procedure described above in step (7) or (8) were washed by shaking them in 20 ml of the washing solution for 10 minutes. This procedure was repeated three times.

(10) Next, peroxidase-labeled anti-mouse IgG antibody (manufacture by Dako) and peroxidase-labeled anti-sheep IgG antibody (manufactured by Dako) were diluted 500-fold with phosphate-buffered physiological saline containing 3% BSA to prepare 20 ml of a solution, and the nitrocellulose membranes were soaked therein at room temperature for 2 hours to effect reaction.

(11) These nitrocellulose membranes were washed by shaking them in 20 ml of the washing solution for 10 minutes. This procedure was repeated three times.

(12) The nitrocellulose membranes obtained from step (11) were soaked in 20 ml of phosphate-buffered physiological saline containing 0.025% 3,3'-diaminobenzidine tetrahydrochloride and 0.01% hydrogen peroxide at room temperature for 15 minutes to develop color.

(13) In order to set up a reference standard for identifying the bands obtained in this western blot technique, the same procedures as described above were repeated using purified apolipoprotein B-100 (prepared domestically), goat anti-apolipoprotein B antibody (manufactured by International Enzyme) and peroxidase-labeled anti-goat IgG antibody (manufactured by Dako). Thus, there was obtained a band of apolipoprotein B-100.

Figure 16:
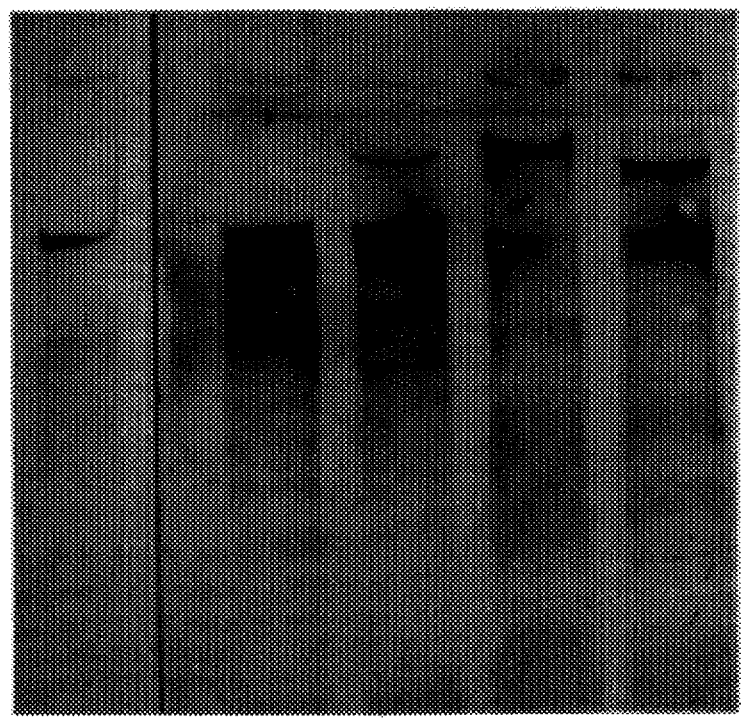
FIG. 16 is a photograph showing electrophoretic patterns observed in the western blot technique carried out to examine the reactivity of the polyclonal antibody to apolipoprotein (a) obtained in Example 11 with apolipoprotein (a).
Figure 17:
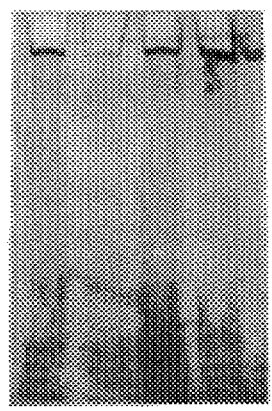
FIG. 17 is a photograph showing the electrophoretic patterns of a negative control observed in the western blot technique carried out to examine the reactivity of the polyclonal antibody to apolipoprotein (a) obtained in Example 11 with apolipoprotein (a).
Figure 18:
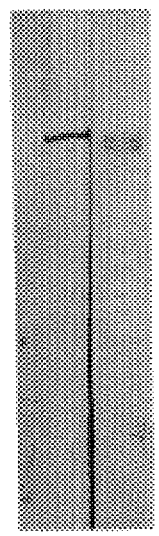
FIG. 18 is a photograph showing the electrophoretic pattern of a control observed in the western blot technique carried out to examine the reactivity of the polyclonal antibody to apolipoprotein (a) obtained in Example 11 with apolipoprotein (a).

The results of this western blot technique are shown in FIGS. 16, 17 and 18.

FIG. 16 shows the nitrocellulose membrane acted on by the polyclonal antibody to apolipoprotein (a) obtained in Example 11.

In FIG. 16, numerals 1 to 4 represent the respective electrophoretic patterns of the four types of purified apolipoprotein (a) derived from human blood serum, and B shows the position of the band of apolipoprotein B-100 useful as a reference standard for identifying the resulting electrophoretic bands.

On the basis of positional relationship with this band of apolipoprotein B-100 [G. Utermann et al., J. Clin. Invest., 80, 458–465(1987)], it can be seen that the bands observed in pattern 1 represent F and B isotypes of apolipoprotein (a), those observed in pattern 2 represent S4 and F isotypes, those observed in pattern 3 represent S4 and S3 isotypes, and those observed in pattern 4 represent S4 and S2 isotypes.

FIG. 17 shows the negative control in which numerals 1 to 4 represent the respective electrophoretic patterns of the four types of purified apolipoprotein (a) derived from human blood serum.

FIG. 18 shows the control in which the nitrocellulose membrane was acted on by anti-lipoprotein (a) antibody reacting with apolipoprotein (a). The sample used was the purified apolipoprotein (a) derived from blood serum which corresponds to the above-described pattern 1. B shows the position of the band of apolipoprotein B-100 as a reference standard.

As can be seen from FIGS. 16 and 18, the polyclonal antibody to apolipoprotein (a) obtained in Example 11 exhibits color development at the same position as anti-lipoprotein (a) antibody reacting with apolipoprotein (a) does. Thus, it has been confirmed that this polyclonal antibody combines specifically with apolipoprotein (a).

Moreover, in FIG. 16, it has been confirmed that the polyclonal antibody to apolipoprotein (a) obtained in Example 11 react with various isotypes of apolipoprotein (a).

Furthermore, in FIG. 17, no color development is observed in the negative control which was not acted on by the polyclonal antibody to apolipoprotein (a) obtained in Example 11 or anti-lipoprotein (a) antibody, indicating that nonspecific color development did not take place.

Reference Example 7

Reactivity with lipoprotein (a) of the polyclonal antibody to apolipoprotein (a) obtained in Example 11

The reactivity with lipoprotein (a) of the polyclonal antibody to apolipoprotein (a) obtained in Example 11 was confirmed by the western blot technique.

(1) Human blood serum having a high lipoprotein (a) concentration was ultracentrifuged to separate a fraction having a specific gravity range of 1.05 to 1.12. This serum fraction was subjected to lysine-Sepharose 4B affinity chromatography (manufactured by Pharmacia-LKB). Thus, there was obtained purified lipoprotein (a).

(2) This purified lipoprotein (a) was dissolved in physiological saline (a 0.9% aqueous solution of sodium chloride) so as to give a concentration of 0.5 mg/ml, and a 2 µl sample of this solution was subjected to electrophoresis using a Titan Gel Lipoprotein Electrophoresis Kit (manufactured by Helena Laboratory). The supporting medium was agarose gel. Using a barbital buffer (pH 8.8) as the electrophoresis buffer, a voltage of 90 V was applied for 75 minutes.

(3) Using a Nova Blot Electrophoretic Transfer Kit (manufactured by Pharmacia-LKB), transfer was carried out on a dry basis according to its instruction manual.

(4) The agarose gel obtained from step (2) was placed on a transfer apparatus and a 9 cm×9 cm nitrocellulose membrane (manufactured by Bio-Rad) was laid thereon. Using a transfer buffer comprising 48 mM Tris, 39 mM glycine, 0.0375% (W/V) SDS and 20% (V/V) methanol, transfer was carried out by passing an electric current of 65 mA for 2 hours.

The succeeding procedures were substantially the same as those described in steps (5) to (12) of Reference Example 6.

Figure 19:
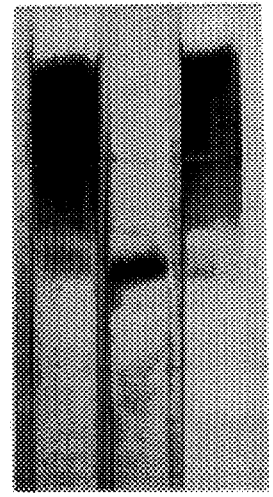
FIG. 19 is a photograph showing electrophoretic patterns observed in the western blot technique carried out to examine the reactivity of the polyclonal antibody to apolipoprotein (a) obtained in Example 11 with lipoprotein (a).

The results of this western blot technique are shown in FIG. 19.

In FIG. 19, P represents the control, N represents the negative control, and S represents the nitrocellulose membrane acted on by the polyclonal antibody to apolipoprotein (a) obtained in Example 11.

By comparison between S, and the control and the negative control in FIG. 19, it has been confirmed that the polyclonal antibody to apolipoprotein (a) obtained in Example 11 does not react with lipoprotein (a).

Reference Example 8

Reactivity with plasminogen of the polyclonal antibody to apolipoprotein (a) obtained in Example 11

The reactivity with plasminogen of the polyclonal antibody to apolipoprotein (a) obtained in Example 11 was confirmed by the western blot technique.

The western blot technique was carried out in the same manner as in Reference Example 4, except that the polyclonal antibody to apolipoprotein (a) obtained in Example 11 was used in place of the polyclonal antibodies to lipoprotein (a) obtained in Examples 9 and 10.

As a result, the polyclonal antibody to apolipoprotein (a) obtained in Example 11 exhibits no color development at the position where the commercially available anti-plasminogen antibody exhibits color development. Thus, it has been confirmed that this polyclonal antibody does not combine with plasminogen.

Moreover, no color development is observed in the negative control which was not acted on by the polyclonal antibody to apolipoprotein (a) obtained in Example 11 or the like, indicating that nonspecific color development did not take place.

EXAMPLE 12

Preparation of a rabbit polyclonal antibody to lipoprotein (a) specifically recognizing the amino acid sequence represented by SEQ ID NO:i in the List of Sequences The antibody-producing immunogen (having KLH as the carrier) obtained in Example 6 was dissolved in physiological saline (a 0.9% aqueous solution of sodium chloride) so as to give a concentration of 1.6 mg/ml. This solution was mixed with an equal amount of Freund's complete adjuvant to form an emulsion, and 1 ml of this emulsion was subcutaneously injected at 20 or more sites of the back of a rabbit (Japanese White) aged 3 months for purposes of immunization.

Two weeks after the initial immunization, the above-described antibody-producing immunogen was dissolved in physiological saline so as to give a concentration of 0.8 mg/ml. This solution was mixed with an equal amount of Freund's incomplete adjuvant to form an emulsion, and 1 ml of this emulsion was injected as a booster. This booster injection was repeated at intervals of 2 weeks.

The antibody titer in the blood serum of this rabbit, which was an immunized animal, was measured by an enzyme immunoassay (ELISA, EIA) at intervals of one week. This ELISA was carried out as follows: The antibody-producing immunogen (having BSA as the carrier) obtained in Example 6 was converted into a solid phase on a microplate, and blood serum obtained from the immunized animal was added thereto to effect reaction. After washing, peroxidase (POD)-labeled anti-mouse IgG antibody was added to the microplate to effect reaction. After washing, a color-producing solution containing hydrogen peroxide and 2,2'-azino-bis(3-ethylbenzthiazoline-6-sulfonic acid) (ABTS) was added to the microplate to develop color. Then, the antibody titer was determined by measuring the absorbance at 415 nm on an EIA plate reader (manufactured by Bio-Rad).

After a total of five booster injections were given, it was noted that the antibody titer reached a plateau. Accordingly, exsanguination was performed and blood serum was separated to obtain 82 ml of antiserum.

This antiserum was centrifuged at 10,000 r.p.m. for 30 minutes to remove any insoluble matter, and then salted-out at 20° C. by adding 0.18 g of sodium sulfate per ml of antiserum. The resulting precipitate fraction of immunoglobulin was dissolved in the least possible amount of 17.5 mM sodium dihydrogen phosphate-disodium hydrogen phosphate buffer (pH 6.3) and then dialyzed thoroughly against this 17.5 mM sodium dihydrogen phosphate-disodium hydrogen phosphate buffer (pH 6.3).

After completion of the dialysis, the dialyzed solution was passed through a DEAE-cellulose ion exchange column (manufactured by Serva) which had been equilibrated with 17.5 mM sodium dihydrogen phosphate-disodium hydrogen phosphate buffer (pH 6.3). By collecting the flow-through fractions, there was obtained a rabbit polyclonal antibody to lipoprotein (a) specifically recognizing the amino acid sequence represented by SEQ ID NO:i in the List of Sequences.

The amount of the antibody thus obtained was 0.74 g as expressed in terms of protein.

EXAMPLE 13

Preparation of a rabbit polyclonal antibody to lipoprotein (a) specifically recognizing the amino acid sequence represented by SEQ ID NO:2 in the List of Sequences The preparation of an antibody was carried out in the same manner as in Example 12, except that the antibody-producing immunogen (having KLH as the carrier) obtained in Example 7 was dissolved in physiological saline so as to give a concentration of 2.2 mg/ml at the time of the initial immunization, the same immunogen was dissolved in physiological saline so as to give a concentration of 1.1 mg/ml at the time of each booster injection, and the antibody-producing immunogen (having BSA as the carrier) obtained in Example 7 was converted into a solid phase and used to determine the antibody titer. Thus, there was obtained a rabbit polyclonal antibody to lipoprotein (a) specifically recognizing the amino acid sequence represented by SEQ ID NO:2 in the List of Sequences.

The amount of the antibody thus obtained was 0.78 g as expressed in terms of protein.

EXAMPLE 14

Preparation of a rabbit polyclonal antibody to apolipoprotein (a) specifically recognizing the amino acid sequence represented by SEQ ID NO:3 in the List of Sequences The preparation of an antibody was carried out in the same manner as in Example 12, except that the antibody-producing immunogen (having KLH as the carrier) obtained in Example 8 was dissolved in physiological saline so as to give a concentration of 1.7 mg/ml at the time of the initial immunization, the same immunogen was dissolved in physiological saline so as to give a concentration of 0.9 mg/ml at the time of each booster injection, and the antibody-producing immunogen (having BSA as the carrier) obtained in Example 8 was converted into a solid phase and used to determine the antibody titer. Thus, there was obtained a rabbit polyclonal antibody to apolipoprotein (a) specifically recognizing the amino acid sequence represented by SEQ ID NO:3 in the List of Sequences.

The amount of the antibody thus obtained was 0.71 g as expressed in terms of protein.

EXAMPLE 15

Method for the determination of lipoprotein (a) by turbidimetric immunoassay

A system for the determination of lipoprotein (a) by turbidimetric immunoassay was established using the polyclonal antibody to lipoprotein (a) obtained in Example 9.

(1) For use in determination, 40 mM Tris-hydrochloric acid buffer (pH 7.0) containing 300 mM sodium chloride and 5% (W/W) polyethylene glycol 6000, and phosphate-buffered physiological saline [5.59 mM disodium hydrogen phosphate, 1.47 mM potassium dihydrogen phosphate, 137 mM sodium chloride, 2.68 mM potassium chloride (pH 7.2)] containing 6 mg/ml of the polyclonal antibody to lipoprotein (a) obtained in Example 9 were prepared as reagents 1 and 2, respectively.

(2) Blood serum having a lipoprotein (a) concentration of 77.0 mg/dl was diluted with physiological saline (a 0.9% aqueous solution of sodium chloride) in three steps. Thus, three samples having lipoprotein (a) concentrations of 25.7 mg/dl, 51.3 mg/dl and 77.0 mg/dl were prepared.

(3) Measurements were made by using a COBAS MIRA automatic analyzer manufactured by F. Hoffmann La Roche. More specifically, 3 μl each sample was mixed with 300 μl of reagent 1 and this mixture was warmed at 37° C. for 5 minutes. After 20 μl of reagent 2 was added thereto and mixed therewith, the resulting mixture was reacted at 37° C. for 5 minutes. Then, its absorbance at 340 nm was measured.

Figure 20:
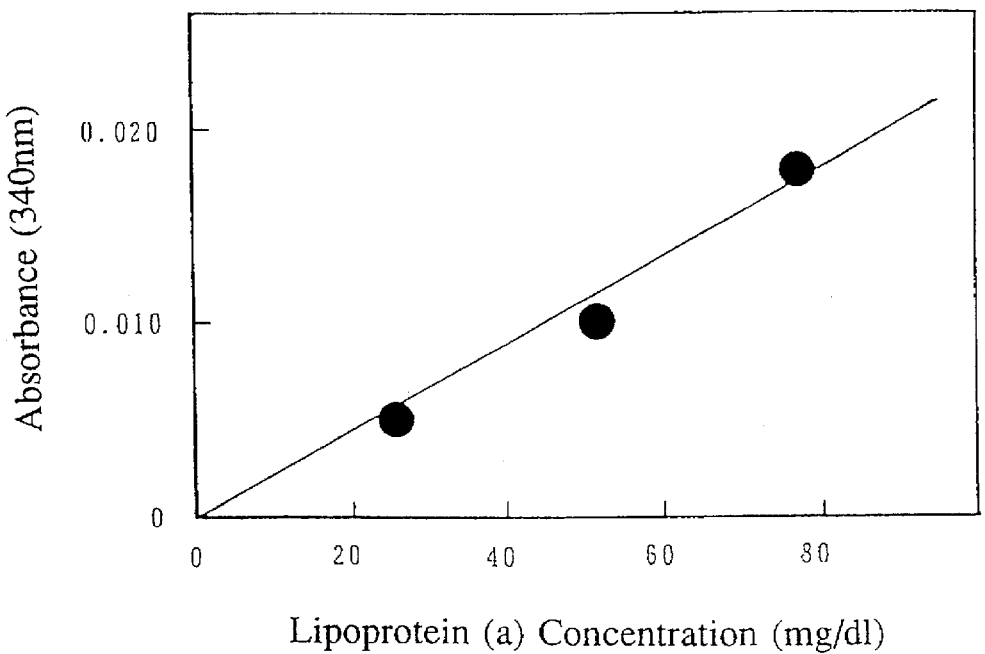
FIG. 20 is a graph showing a calibration curve for the determination of lipoprotein (a) by turbidimetric immunoassay using the polyclonal antibody to lipoprotein (a) obtained in Example 9.

The calibration curve obtained by measuring the three samples is shown in FIG. 20.

As can be seen from this figure, the calibration curve used in this method is a straight line passing through the origin. Thus, it has been confirmed that the method for the determination of lipoprotein (a) in accordance with the present invention enables quantitative determination of lipoprotein (a).

EXAMPLE 16
Method for the determination of lipoprotein (a) by turbidimetric immunoassay A system for the determination of lipoprotein (a) by turbidimetric immunoassay was established using the polyclonal antibody to lipoprotein (a) obtained in Example 10.

Measurements were made in the same manner as in Example 15, except that, as a component of reagent 2 prepared in step (1) of Example 15, the polyclonal antibody to lipoprotein (a) obtained in Example 10 was used at the same concentration in place of the polyclonal antibody to lipoprotein (a) obtained in Example 9.

Figure 21:
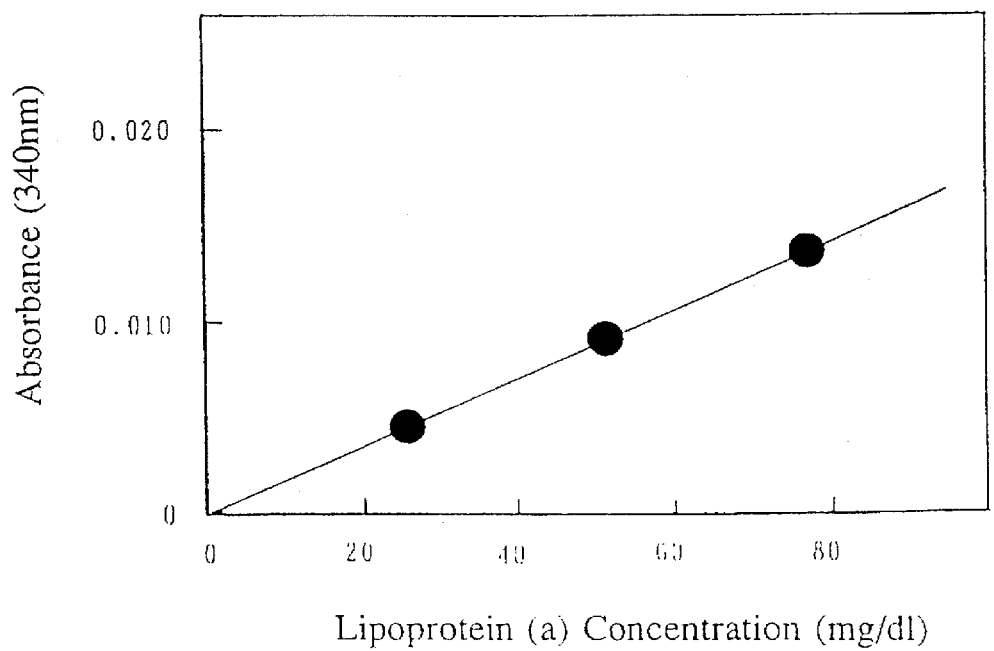
FIG. 21 is a graph showing a calibration curve for the determination of lipoprotein (a) by turbidimetric immunoassay using the polyclonal antibody to lipoprotein (a) obtained in Example 10.

The calibration curve obtained by measuring the three samples is shown in FIG. 21.

As can be seen from this figure, the calibration curve used in this method is a straight line passing through the origin. Thus, it has been confirmed that the method for the determination of lipoprotein (a) in accordance with the present invention enables quantitative determination of lipoprotein (a).

EXAMPLE 17
Method for the determination of lipoprotein (a) by ELISA

A system for the determination of lipoprotein (a) by ELISA was established using the polyclonal antibody to lipoprotein (a) obtained in Example 9.

(1) A 50 μg/ml solution of anti-lipoprotein (a) antibody (manufactured by International Enzyme) was added to wells of a 96-well microplate (manufactured by Nunc) in an amount of 100 μl per well and allowed to stand at 37° C. for 2 hours to convert the anti-lipoprotein (a) antibody into a solid phase (capture antibody).

(2) After this microplate was washed with a washing solution [phosphate-buffered physiological saline [5.59 mM disodium hydrogen phosphate, 1.47 mM potassium dihydrogen phosphate, 137 mM sodium chloride, 2.68 mM potassium chloride (pH 7.2)] containing 0.05% Tween 20], 10 mM potassium dihydrogen phosphate-dipotassium hydrogen phosphate buffer (pH 7.2) containing 1% BSA was added to the wells thereof in an amount of 300 μl per well and allowed to stand at 37° C. for 2 hours to effect blocking. Thereafter, the microplate was washed again with the washing solution.

(3) Blood serum having a lipoprotein (a) concentration of 100 mg/dl was diluted with physiological saline (a 0.9% aqueous solution of sodium chloride) in five steps. Thus, five samples having lipoprotein (a) concentrations of 20 mg/dl, 40 mg/dl, 60 mg/dl, 80 mg/dl and 100 mg/dl were prepared.

(4) The above-described five samples were diluted 500-fold with physiological saline. These dilutions were separately pipetted into the wells of the microplate obtained from step (2) in an amount of 100 μl per well and allowed to stand at 37° C. for 2 hours to effect an antigen-antibody reaction.

(5) After this microplate was washed with the washing solution, the polyclonal antibody to lipoprotein (a) obtained in Example 9 was dissolved in phosphate-buffered physiological saline containing 3% BSA so as to give a concentration of 50 μg/ml, and the resulting solution was added to the wells of the microplate in an amount of 100 μl per well and allowed to stand at 37° C. for 2 hours to effect reaction (primary antibody). Thereafter, the microplate was washed with the washing solution.

(6) Peroxidase (POD)-labeled anti-mouse IgG antibody (manufactured by Amersham) was diluted 2,000-fold with phosphate-buffered physiological saline containing 3% BSA, added to the wells of the microplate obtained from step (5) in an amount of 100 μl per well, and allowed to stand at 37° C. for 2 hours to effect reaction (secondary antibody).

(7) After this microplate was washed with the washing solution, a peroxidase reaction solution (prepared by adding 2 μl of 1.7% hydrogen peroxide to 1 ml of 50 mM disodium hydrogen phosphate-24 mM citric acid buffer containing 3 mM o-phenylenediamine, immediately before use) was added to the wells thereof in an amount of 100 μl per well and reacted at room temperature. After 15 minutes, 6N sulfuric acid was added to the wells thereof in an amount of 50 μl per well to stop the reaction.

(8) The absorbances at 492 nm of the wells of this microplate were measured on an EIA microplate reader (manufactured by Bio-Rad).

Figure 22:
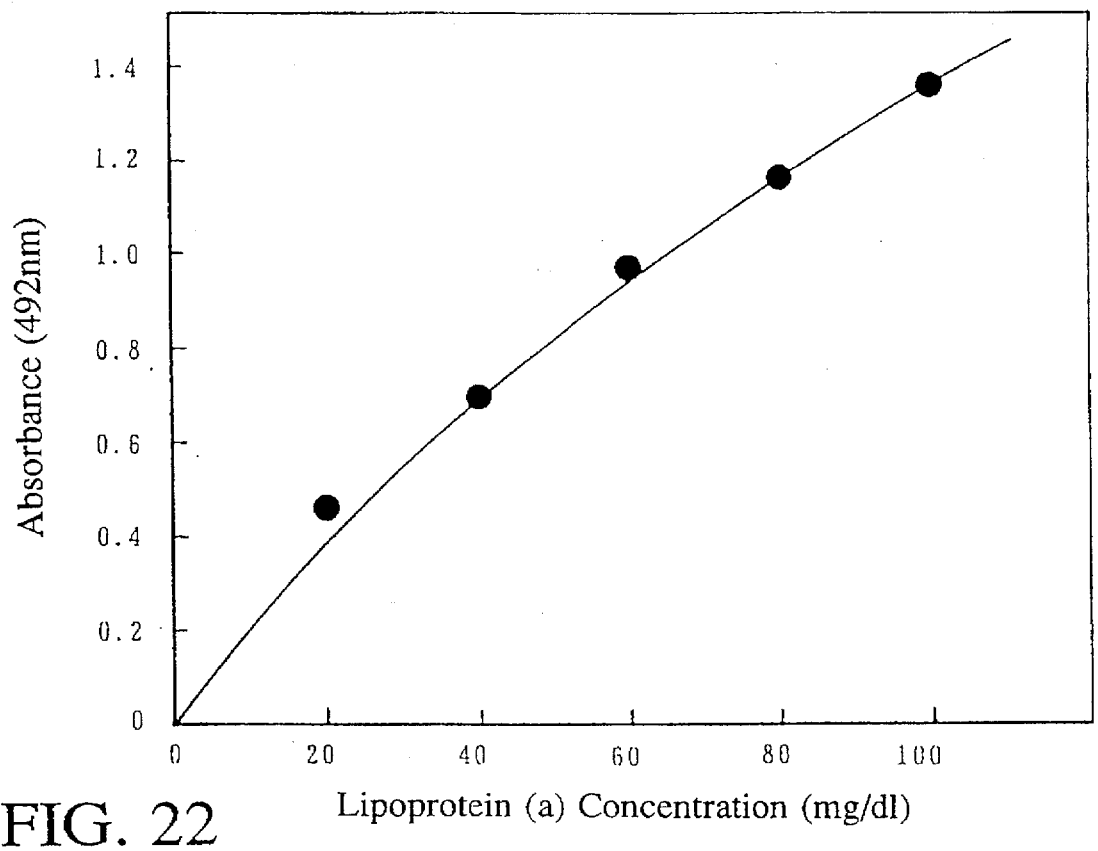
FIG. 22 is a graph showing a calibration curve for the determination of lipoprotein (a) by ELISA using the polyclonal antibody to lipoprotein (a) obtained in Example 9.

The calibration curve obtained by measuring the five samples is shown in FIG. 22.

From these results, it has been confirmed that the method for the determination of lipoprotein (a) in accordance with the present invention enables quantitative determination of lipoprotein (a).

EXAMPLE 18
Method for the determination of lipoprotein (a) by ELISA

A system for the determination of lipoprotein (a) by ELISA was established using the polyclonal antibody to lipoprotein (a) obtained in Example 10.

Measurements were made in the same manner as Example 17, except that the polyclonal antibody to lipoprotein (a) obtained in Example 10 was used at the same concentration in step (5) of Example 17, in place of the polyclonal antibody to lipoprotein (a) obtained in Example 9.

Figure 23:
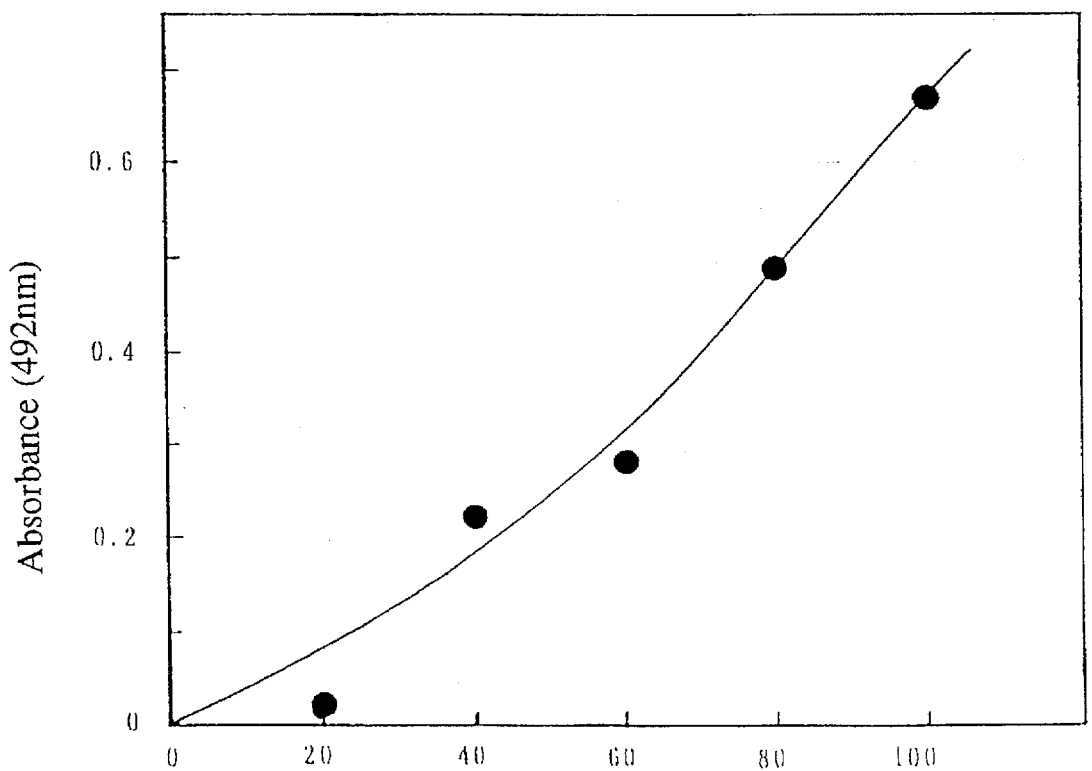
FIG. 23 is a graph showing a calibration curve for the determination of lipoprotein (a) by ELISA using the polyclonal antibody to lipoprotein (a) obtained in Example 10.

The calibration curve obtained by measuring the five samples is shown in FIG. 23.

From these results, it has been confirmed that the method for the determination of lipoprotein (a) in accordance with the present invention enables quantitative determination of lipoprotein (a).

EXAMPLE 19
Comparison of the measured values for lipoprotein (a)

The measured values obtained by the present method for the determination of lipoprotein (a) by ELISA using the polyclonal antibody to lipoprotein (a) obtained in Example 10 were compared with those obtained by ELISA using the lipoprotein (a)-determining reagent of company A and by turbidimetric immunoassay using the lipoprotein (a)-determining reagent of company B.

Samples 1, 2 and 3 comprising three types of blood sera were measured according to the present method for the determination of lipoprotein (a) by ELISA using the polyclonal antibody to lipoprotein (a) obtained in Example 10. The ELISA was carried out in the same manner as in Example 17.

The measurement of three samples by using the lipoprotein (a)-determining reagent of company A and the lipoprotein (a)-determining reagent of company B was made according to their instruction manuals.

The results of these measurements are summarized in Table 4.

TABLE 4

|          | Method of the invention | Reagent of company A | Reagent of company B |
|----------|-------------------------|----------------------|----------------------|
| Sample 1 | 58.0                    | 51.3                 | 54.0                 |
| Sample 2 | 0.0                     | 0.0                  | 5.0 or less          |
| Sample 3 | 42.0                    | 42.0                 | 44.9                 |

(The values are expressed in mg/dl.)

From these results, it has been confirmed that the measured values for lipoprotein (a) obtained by the present method for the determination of lipoprotein (a) are substantially the same as those obtained by the methods currently in use and, therefore, the method for the determination of lipoprotein (a) in accordance with the present invention can be practically used for purposes of clinical examination.

Reference Example 9
Influence of plasminogen on the present method for the determination of lipoprotein (a)

In order to investigate the influence of plasminogen on the present method for the determination of lipoprotein (a), the following experiments were carried out using four types of primary antibodies (A-1, A-2, B and C).

(1) Goat anti-plasminogen antibody (manufactured by Medical Biological Laboratory) was converted into a solid phase on a microplate and used as a capture antibody.

(2) Four types of antibodies (A-1, A-2, B and C) were provided as primary antibodies. A-1 comprised the polyclonal antibody to lipoprotein (a) obtained in Example 9, A-2 comprised the polyclonal antibody to lipoprotein (a) obtained in Example 10, B comprised a mouse monoclonal antibody combining with plasminogen but not combining with lipoprotein (a) (i.e., an antibody combining specifically with the Kringle 1, Kringle 2 and Kringle 3 portions of plasminogen) (prepared domestically), and C comprised a mouse polyclonal antibody obtained using lipoprotein (a) as the immunogen but not subjected to an absorption treatment with plasminogen (prepared domestically).

(3) Peroxidase-labeled anti-mouse IgG antibody (manufactured by Amersham) was provided as a secondary antibody.

(4) Using purified plasminogen (prepared domestically), five samples having plasminogen concentrations of 44 mg/dl, 88 mg/dl, 132 mg/dl, 176 mg/dl and 220 mg/dl were prepared. Prior to use, these samples were diluted 3,000-fold with physiological saline (a 0.9% aqueous solution of sodium chloride) and used for measurements.

(5) The above-described five samples were measured by ELISA using the capture antibody described above in step (1), the four primary antibodies described above in step (2), and the secondary antibody described above in step (3). The ELISA was carried out in the same manner as in Example 17.

Figure 24:
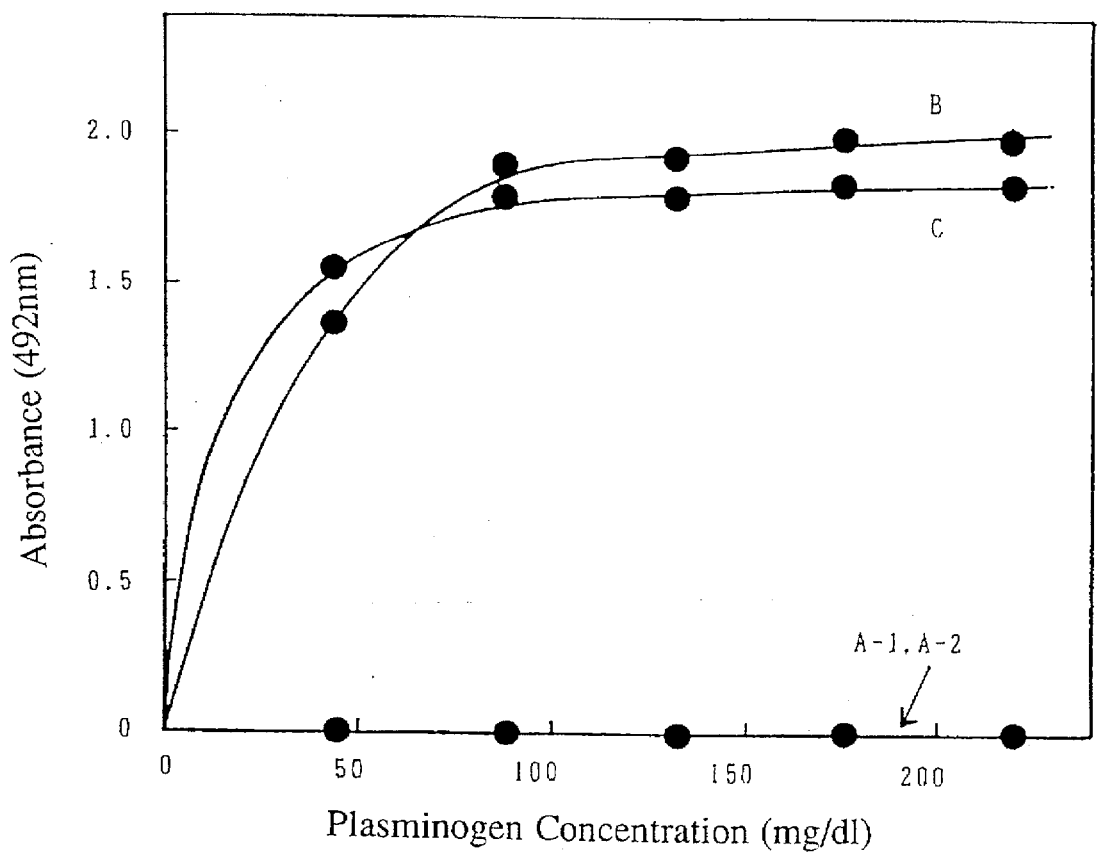
FIG. 24 is a graph showing the influence of plasminogen on the method for the determination of lipoprotein (a) in accordance with the present invention.

The results obtained by measuring the five plasminogen samples are shown in FIG. 24.

It can be seen from these results that plasminogen is measured together in the measuring system using, as the primary antibody, an antibody (B) combining solely with plasminogen and the measuring system using, as the primary antibody, an antibody (C) obtained from an immunogen comprising lipoprotein (a).

In contrast, plasminogen is by no means measured together in the present system for the determination of lipoprotein (a) using, as the primary antibody, the polyclonal antibody (A-1, A-2) to lipoprotein (a) obtained in Example 9 or 10.

Thus, it has been confirmed that the method for the determination of lipoprotein (a) in accordance with the present invention is a method capable of determining the concentration of lipoprotein (a) accurately without undergoing the influence of any plasminogen present in the samples.

EXAMPLE 20
Method for the determination of apolipoprotein (a) by ELISA

A system for the determination of apolipoprotein (a) by ELISA was established using the polyclonal antibody to apolipoprotein (a) obtained in Example 11.

(1) Anti-lipoprotein (a) antibody also combining with apolipoprotein (a) (manufactured by International Enzyme) was treated with pepsin to fragment it to F(ab')$_2$. A 15 μg/ml solution of this antibody fragment was added to wells of a 96-well microplate (manufactured by Nunc) in an amount of 100 μl per well and allowed to stand at 37° C. for 2 hours to convert the anti-lipoprotein (a) antibody fragment into a solid phase (capture antibody).

(2) After this microplate was washed with a washing solution [phosphate-buffered physiological saline [5.59 mM disodium hydrogen phosphate, 1.47 mM potassium dihydrogen phosphate, 137 mM sodium chloride, 2.68 mM potassium chloride (pH 7.2)] containing 0.05% Tween 20], 10 mM potassium dihydrogen phosphate-dipotassium hydrogen phosphate buffer (pH 7.2) containing 1% BSA was added to the wells thereof in an amount of 300 μl per well and allowed to stand at 37° C. for 2 hours to effect blocking. Thereafter, the microplate was washed again with the washing solution.

(3) Human blood serum having a high lipoprotein (a) concentration was ultracentrifuged to separate a fraction having a specific gravity range of 1.05 to 1.12. Then, the resulting serum fraction was subjected to lysine-Sepharose 4B affinity chromatography (manufactured by Pharmacia-LKB). Thus, there was obtained purified lipoprotein (a).

Then, this purified lipoprotein (a) was treated by the addition of 1 mM dithiothreitol and ultracentrifuged again to separate a fraction having a specific gravity of 1.21 or greater. Thus, the LDL moiety was removed to obtain purified apolipoprotein (a).

This purified apolipoprotein (a) was diluted with physiological saline (a 0.9% aqueous solution of sodium chloride) so as to give a concentration of 40 mg/dl and then diluted with physiological saline in four steps. Thus, four samples having apolipoprotein (a) concentrations of 10 mg/dl, 20 mg/dl, 30 mg/dl and 40 mg/dl were prepared.

(4) The above-described four samples were diluted 100-fold with a sample diluting solution [10 mM Tris, 0.9% sodium chloride, 1% BSA(pH 8.0)]. These dilutions were separately pipetted into the wells of the microplate obtained from step (2) in an amount of 100 μl per well and allowed to stand at 37° C. for 2 hours to effect an antigen-antibody reaction.

(5) After this microplate was washed with the washing solution, the polyclonal antibody to apolipoprotein (a) obtained in Example 11 was dissolved in phosphate-buffered physiological saline containing 3% BSA so as to give a concentration of 50 μg/ml, and the resulting solution was added to the wells of the microplate in an amount of 100 μl per well and allowed to stand at 37° C. for 2 hours to effect reaction (primary antibody). Thereafter, the microplate was washed with the washing solution.

The succeeding procedures were substantially the same as those described in steps (6) to (8) of Example 17.

Figure 25:
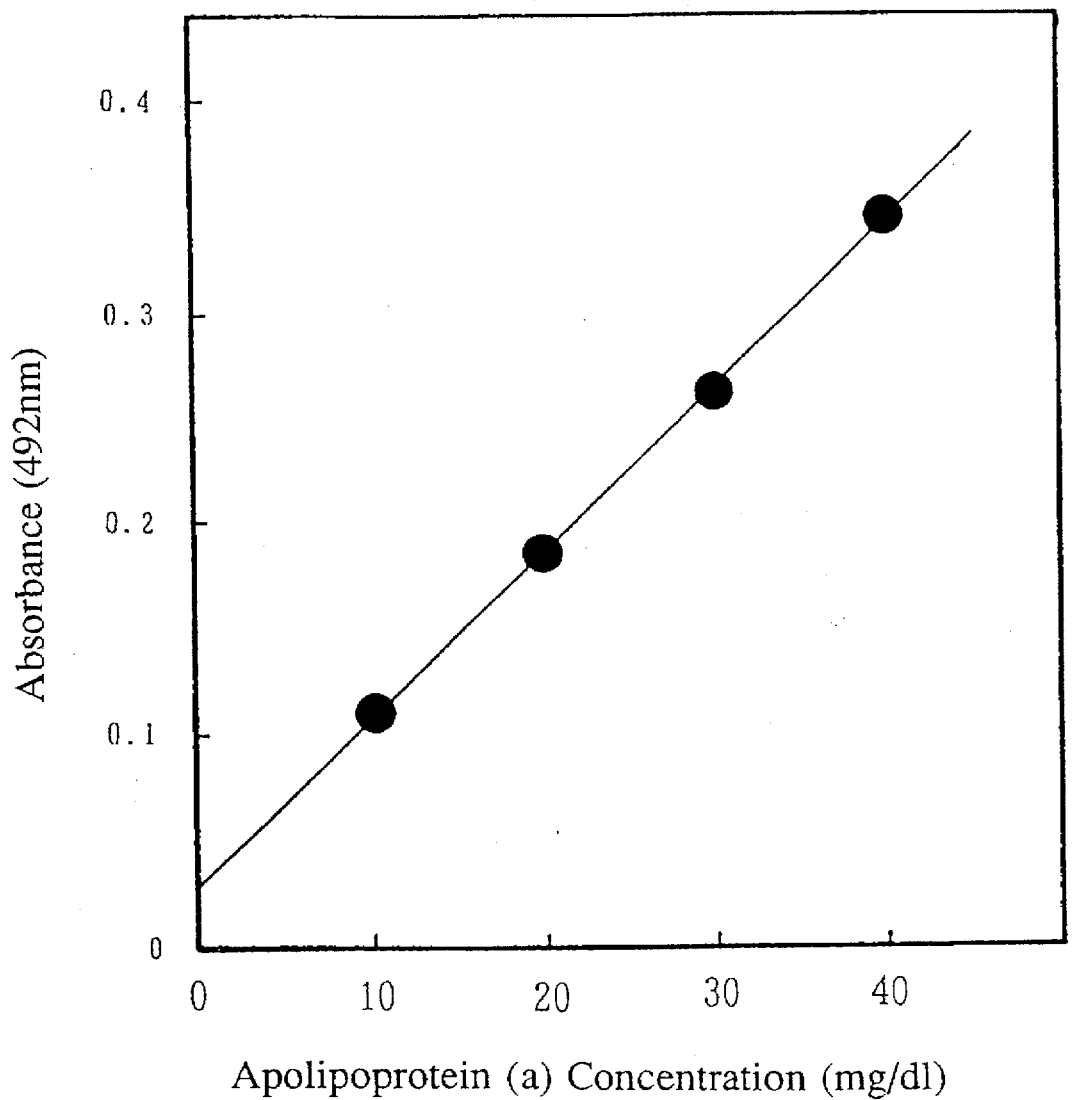
FIG. 25 is a graph showing a calibration curve for the determination of apolipoprotein (a) by ELISA using the polyclonal antibody to apolipoprotein (a) obtained in Example 11.

The calibration curve obtained by measuring the four samples is shown in FIG. 25.

From these results, it has been confirmed that the method for the determination of apolipoprotein (a) in accordance with the present invention enables quantitative determination of apolipoprotein (a).

EXAMPLE 21

Influence of serum samples on the method for the determination of apolipoprotein (a)

In the method for the determination of apolipoprotein (a) by ELISA using the polyclonal antibody to apolipoprotein (a) obtained in Example 11, it was confirmed by addition and recovery tests that the method was not influenced by serum samples.

(1) Three types of blood sera (A, B, C) were provided and the following samples were prepared using them as base materials.

(i) Three samples prepared by mixing 0.1 ml of physiological saline (a 0.9% aqueous solution of sodium chloride) with 0.9 ml of each of the three blood sera (A, B, C).

(ii) Three samples prepared by diluting the purified apolipoprotein (a) obtained in Example 20 with physiological saline so as to give a concentration of 100 mg/dl and mixing 0.1 ml of this solution with 0.9 ml of each of the three blood sera (A, B, C) to increase the apolipoprotein (a) concentrations of the three serum samples prepared in (i) by 10 mg/ml.

(iii) A sample prepared by diluting the purified apolipoprotein (a) obtained in Example 20 with physiological saline so as to give a concentration of 10 mg/dl.

(2) The absorbances of the above-described seven samples were measured according to the method for the determination of apolipoprotein (a) by ELISA as described in Example 20. The results thus obtained are shown in Table 5.

TABLE 5

|  | Serum A | Serum B | Serum C |
|---|---|---|---|
| (i) Absorbance of each sample comprising a blood serum mixed with physiological saline | 0.047 | 0.060 | 0.011 |
| (iii) Absorbance of 10 mg/dl of purified apolipoprotein (a) | 0.110 | 0.110 | 0.110 |
| (iv) Theoretical absorbance of each serum sample of (i) having an apolipoprotein (a) concentration increased by 10 mg/dl [(i) + (iii)] | 0.157 | 0.170 | 0.121 |
| (ii) Measured absorbance of each serum sample of (i) having an apolipoprotein (a) concentration increased by 10 mg/dl | 0.165 | 0.167 | 0.132 |
| (v) Percentage of the measured absorbance based on the theoretical value [(ii)/(iv)] | 105% | 98.2% | 109% |

It can be seen from these results that, when serum samples are measured according to the present method for the determination of apolipoprotein (a), measured values approximately equal to theoretical ones are obtained.

Thus, it has been confirmed that the method for the determination of apolipoprotein (a) in accordance with the present invention is a method capable of determining apolipoprotein (a) in serum samples accurately without undergoing the influence of nonspecific reactions or the like caused by the serum samples and, therefore, can be practically used for purposes of clinical examination.

EXAMPLE 22

Preparation of a mouse monoclonal antibody to lipoprotein (a) specifically recognizing the amino acid sequence represented by SEQ ID NO:2 in the List of Sequences

[1] Immunization of an animal (1) The antibody-producing immunogen (having KLH as the carrier) obtained in Example 7 was dissolved in physiological saline (a 0.9% aqueous solution of sodium chloride) so as to give a concentration of 500 µg/ml.

This solution was mixed with an equal amount of Freund's complete adjuvant to form an emulsion, and 0.5 ml of this emulsion was subcutaneously injected into the abdomen of a female BALB/c mouse (Charles River Japan Inc.) aged 8 weeks for purposes of immunization.

(2) Two weeks after the initial immunization, the above-described antibody-producing immunogen was dissolved in physiological saline so as to give a concentration of 250 µg/ml, this solution was mixed with an equal amount of Freund's incomplete adjuvant to form an emulsion, and 0.5 ml of this emulsion was injected as a booster. This booster injection was repeated at intervals of 2 weeks.

(3) The antibody titer in the blood serum of this mouse, which was an immunized animal, was measured by an enzyme immunoassay (ELISA, EIA) at intervals of one week starting from 6 weeks after the initial immunization. This ELISA was carried out as follows: The antibody-producing immunogen (having BSA as the carrier) obtained in Example 7 was converted into a solid phase on a microplate, and blood serum obtained from the immunized animal was added thereto to effect reaction. After washing, peroxidase (POD)-labeled anti-mouse IgG antibody was added to the microplate to effect reaction. After washing, a color-producing solution containing hydrogen peroxide and 2,2'-azino-bis(3-ethylbenzthiazoline-6-sulfonic acid) (ABTS) was added to the microplate to develop color. Then, the antibody titer was determined by measuring the absorbance at 415 nm on an EIA plate reader (manufactured by Bio-Rad).

(4) After the lapse of 16 weeks from the initial immunization, it was noted that the antibody titer reached a plateau. Accordingly, the antibody-producing immunogen (having KLH as the carrier) obtained in Example 7 was dissolved in physiological saline so as to give a concentration of 800 µg/ml, and 0.5 ml of this solution was subcutaneously injected into the abdomen of this immunized mouse.

After 3 days, the spleen was excised from this immunized mouse.

[2] Growth of myeloma cells

The P3-X63-Ag8-U1 strain (Japanese Cancer Research Resources Bank 9085), which is a hypoxanthine-guanine phosphoribosyltransferase-deficient myeloma cell strain derived from a BALB/c mouse, was grown in RPMI1640 tissue culture medium (manufactured by Biocell) containing 10% fetal calf serum and supplemented with glutamine, penicillin and streptomycin.

More specifically, such myeloma cells were grown in a medium-sized bottle for cell culture (manufactured by Nunc; 200 ml capacity) until about 80% of the bottom surface of the bottle was occupied by the cells. The number of cells was counted with a hemocytometer according to the dye-exclusion technique using trypan blue.

[3] Cell fusion (1) The spleen obtained from the above-described immunized mouse was fully macerated by use of stainless steel mesh #200 and filtered while being washed with serum-free RPMI1640 liquid medium.

Thereafter, the resulting cell suspension was centrifuged at 200×g to separate spleen cells.

These spleen cells were further washed three times with serum-free RPMI1640 liquid medium.

(2) These spleen cells and the above-described grown P3-X63-Ag8-U1 strain myeloma cells were mixed in a ratio of 5:1 and centrifuged.

The mixed cells were slowly suspended in RPMI1640 liquid medium containing 50% polyethylene glycol 1500 (PEG 1500; manufactured by Boehringer Mannheim).

Then, this suspension was gradually diluted with RPMI1640 liquid medium so as to give a final polyethylene glycol concentration of 5%.

(3) The cells were separated therefrom by centrifugation and dispersed slowly in a growth medium comprising S-clone medium (manufactured by Sanko Junyaku Co., Ltd.) containing 5% hybridoma cloning factor (manufactured by Origen).

Each well of a 96-well flat-bottom micro titer plate (manufactured by Nunc) was inoculated with 100 µl of the suspension containing $10^6$ cells, and incubated at 37° C. in an atmosphere containing 5% carbon dioxide.

(4) One day after the cell fusion, 100 µl of HAT medium [the above-described growth medium supplemented with 0.01 mM hypoxanthine, 1.6 µM thymidine and 0.04 µM aminopterin (all manufactured by Tokyo Kasei Kogyo Co., Ltd.)] was added to each well.

For the succeeding 3 days, about a half of the HAT medium was replaced every day by fresh HAT medium. Thereafter, the same replacement was performed at intervals of 2 or 3 days.

(5) Cells were observed under the microscope.

Clones of hybridomas (fused cells) began to appear after 10 days or more. After 14 days or more, the supernatants obtained from the wells were screened by ELISA in order to test them for the production of an antibody recognizing the amino acid sequence represented by SEQ ID NO:2 in the List of Sequences. This ELISA was carried out in the same manner as in Reference Example 2.

(6) With respect to the wells giving a positive test for antibody production, the cells were spread over a 24-well plate and cultured. As the cell density became higher, the cells were cultured on larger scales using small-sized and medium-sized bottles.

(7) Hybridomas were cultured and maintained in HT medium (HAT medium containing neither aminopterin nor hybridoma cloning factor).

(8) The production of an antibody recognizing the amino acid sequence represented by SEQ ID NO:2 in the List of Sequences was tested by ELISA in the same manner as in Reference Example 2. As a result, there were detected four hybridomas productive of an antibody combining with the antibody-producing immunogen (having BSA as the carrier) obtained in Example 7, which is a peptide including the amino acid sequence represented by SEQ ID NO:2 in the List of Sequence, but not combining with BSA.

[4] Hybridoma subcloning (1) The above-described 4 hybridomas were subcloned according to the limiting dilution technique.

The number of cells of each hybridoma was counted with a hemocytometer according to the dye-exclusion technique using trypan blue.

Then, the cells of each hybridoma were suspended in HT medium at two cell densities of 0.5 and 1 viable cell per 100 µl of HT medium. Each of these suspensions was pipetted into the wells of a 96-well flat-bottom microplate in an amount of 100 µl per well.

These hybridomas were grown with the medium being replaced at intervals of 2 or 3 days.

(2) After 2 weeks, the number of colonies present in each well was counted under the microscope, and the wells productive of an antibody combining with the antibody-producing immunogen (having BSA as the carrier) obtained in Example 7, which is a peptide including the amino acid sequence represented by SEQ ID NO:2 in the List of Sequence, but not combining with BSA were detected by ELISA in the same manner as described above.

Thus, there were obtained four wells which each contained only one colony and were productive of an antibody as described above.

(3) These hybridomas were transferred to a 24-well plate and cultured for 2 weeks until a good growth of cells was achieved.

(4) Then, the reactivity with lipoprotein (a) of the antibodies produced by these hybridomas was tested by the western blot technique.

This western blot technique was carried out in the same manner as in Reference Example S, except that their reactivity with LDL was not tested and the supernatants of the hybridoma cultures were used in place of the polyclonal antibodies to lipoprotein (a) obtained in Examples 9 and 10.

As a result, one hybridoma was found to be a cell strain productive of an antibody to lipoprotein (a) specifically recognizing the amino acid sequence represented by SEQ ID NO:2 in the List of Sequences.

(5) This hybridoma was cloned again in the same manner as described above in steps (1) and (2). By examining each well for antibody production, there were obtained a total of 40 hybridoma clones characterized in that only one hybridoma colony was present in a well and the hybridoma colony which produced an antibody combining with the antibody-producing immunogen (having BSA as the carrier) obtained in Example 7, which is a peptide including the amino acid sequence represented by SEQ ID NO:2 in the List of Sequences, but not combining with BSA.

(6) The reactivity with lipoprotein (a) of the antibodies produced by these hybridoma clones was tested again by the western blot technique in the same manner as described above in step (4).

As a result, it has been confirmed that all of these hybridoma clones are cells productive of an antibody to lipoprotein (a) which specifically recognizes the amino acid sequence represented by SEQ ID NO:2 in the List of Sequences.

(7) This cell strain was employed as a hybridoma cell strain (243G7E7F10 strain) for producing a monoclonal antibody to lipoprotein (a) which specifically recognizes a part or the whole of the amino acid sequence represented by SEQ ID NO:2 in the List of Sequences.

This hybridoma cell strain (243G7E7F10 strain) was deposited on Aug. 4, 1993 with the National Institute of Bioscience and Human-Technology, the Agency of Industrial Science and Technology, the Ministry of International Trade and Industry, Japan, and assigned FERM BP-4379.

[5] Production of a monoclonal antibody (1) Using a medium-sized bottle (manufactured by Nunc), the resulting cell strain for producing a monoclonal antibody to lipoprotein (a) was grown in HT medium until about 80% of its bottom surface was occupied by cells.

(2) Thereafter, these hybridoma cells were scraped out and collected by centrifugation at 200×g for 5 minutes.

Subsequently, they were washed three times with serum-free RPMI1640 liquid medium and then suspended in 2 ml of RPMI1640 liquid medium.

(3) 1 ml of the hybridoma cell suspension obtained in the above-described step (2) was injected into the abdominal cavity of a male BALB/c mouse (Charles River Japan Inc.) which had previously been treated with 2,6,10,14-tetramethylpentadecane.

If no expansion of the abdomen of this mouse was observed within 2 weeks after the injection, the same procedure was repeated.

(4) As soon as an expansion of the abdomen of this mouse was observed, ascites was collected therefrom.

This ascites was centrifuged at 200×g for 5 minutes to separate the supernatant containing a monoclonal antibody to lipoprotein (a) from the hybridoma cells.

[6] Purification of the monoclonal antibody (1) 1.8 g of sodium sulfate was added, with stirring, at 22° C. to 10 ml of the supernatant containing a monoclonal antibody to lipoprotein (a). After sodium sulfate was completely dissolved, the stirring was continued for an additional hour to effect salting-out.

(2) This mixture was centrifuged at 22° C. (7000×g, 15 minutes), and the precipitate separated from the supernatant was dissolved in 2 ml of 40 mM sodium phosphate buffer (pH 8.0) containing 30 mM sodium chloride.

(3) Next, this solution was thoroughly dialyzed against 40 mM sodium phosphate buffer (pH 8.0) containing 30 mM sodium chloride, and then centrifuged at 1000×g for 20 minutes to remove any insoluble matter.

(4) This solution was passed at a flow rate of 0.4 ml/min. through a DEAE-cellulose ion exchange column (1×10 cm; manufactured by Serva) which had been equilibrated with 40 mM sodium phosphate buffer (pH 8.0) containing 30 mM sodium chloride, and the eluate was collected in 2 ml fractions.

(5) Absorbance measurement at 280 nm revealed that immunoglobulin G (IgG) was contained in the flow-through fractions of the eluate. Accordingly, the flow-through fractions were collected and concentrated to 2 ml.

(6) The resulting concentrate was further purified by protein A-Sepharose CL-4B affinity chromatography (manufactured by Pharmacia-LKB) to obtain a mouse monoclonal antibody to lipoprotein (a) specifically recognizing the amino acid sequence represented by SEQ ID NO:2 in the List of Sequences.

The amount of the monoclonal antibody thus obtained was 15 mg as expressed in terms of protein.

According to the Ouchterlony immunodiffusion method using a commercially available specific anti-mouse immunoglobulin antiserum (manufactured by Dako), the class and subtype of the resulting monoclonal antibody to lipoprotein (a) was determined to be $IgG_1$ and λ chain respectively.

Reference Example 10

Reactivity of the monoclonal antibody to lipoprotein (a) obtained in Example 22 with the peptides represented by SEQ ID NO:8, SEQ ID NO:9 and SEQ ID NO:10 in the List of Sequences The reactivity of the monoclonal antibody to lipoprotein (a) obtained in Example 22 with the peptides represented by SEQ ID NO:8, SEQ ID NO:9 and SEQ ID NO:10 in the List of Sequences, which are peptides including the amino acid sequences represented by SEQ ID NO:1, SEQ ID NO:2 and SEQ ID NO:3 in the List of Sequences, respectively, was confirmed by ELISA.

(1) The antibody-producing immunogen (having BSA as the carrier) obtained in Example 6, the antibody-producing immunogen (having BSA as the carrier) obtained in Example 7, and the antibody-producing immunogen (having BSA as the carrier) obtained in Example 8 were each dissolved in physiological saline (a 0.9% aqueous solution of sodium chloride) so as to give a concentration of 5 µg/ml. These solutions were added to wells of a 96-well microplate (manufactured by Nunc) in an amount of 100 µl per well and allowed to stand at 37° C. for 2 hours to convert the peptides into a solid phase.

(2) After this microplate was washed with a washing solution [phosphate-buffered physiological saline (5.59 mM disodium hydrogen phosphate, 1.47 mM potassium dihydrogen phosphate, 137 mM sodium chloride, 2.68 mM potassium chloride (pH 7.2)) containing 0.05% Tween 20], 10 mM potassium dihydrogen phosphate-dipotassium hydrogen phosphate buffer (pH 7.2) containing 1% BSA was added to the wells thereof in an amount of 300 µl per well and allowed to stand at 37° C. for 2 hours to effect blocking. Thereafter, the microplate was washed again with the washing solution.

(3) The monoclonal antibody to lipoprotein (a) obtained in Example 22 was diluted with phosphate-buffered physiological saline containing 3% BSA to prepare four samples having antibody concentrations of 0.1 µg/ml, 0.5 µg/ml, 1.0 µg/ml and 5.0 µg/ml, respectively. These dilutions was added to the respective wells in an amount of 100 µl per well and allowed to stand at 37° C. for 2 hours to effect reaction. Thereafter, the microplate was washed with the washing solution.

(4) As a control, phosphate-buffered physiological saline containing 3% BSA was added to the wells of another microplate as obtained from step (2) in an amount of 100 µl per well and allowed to stand at 37° C. for 2 hours to effect reaction. Thereafter, the microplate was washed with the washing solution.

(5) Peroxidase (POD)-labeled anti-mouse IgG antibody (manufactured by Amersham) was diluted 2,000-fold with phosphate-buffered physiological saline containing 3% BSA, added to the wells of the microplates obtained from steps (3) and (4) in an amount of 100 µl per well and allowed to stand at 37° C. for 2 hours to effect reaction.

(6) After these microplates were washed with the washing solution, a peroxidase reaction solution (prepared by adding 2 µl of 1.7% hydrogen peroxide to 1 ml of 50 mM disodium hydrogen phosphate-24 mM citric acid buffer containing 3 mM o-phenylenediamine, immediately before use) was added to the wells thereof in an amount of 100 µl per well and they were reacted at room temperature. After 15 minutes, 6N sulfuric acid was added to the wells thereof in an amount of 50 µl per well to stop the reaction.

(7) The absorbances at 492 nm of the wells of these microplates were measured on an EIA plate reader (manufactured by Bio-Rad).

Figure 26:
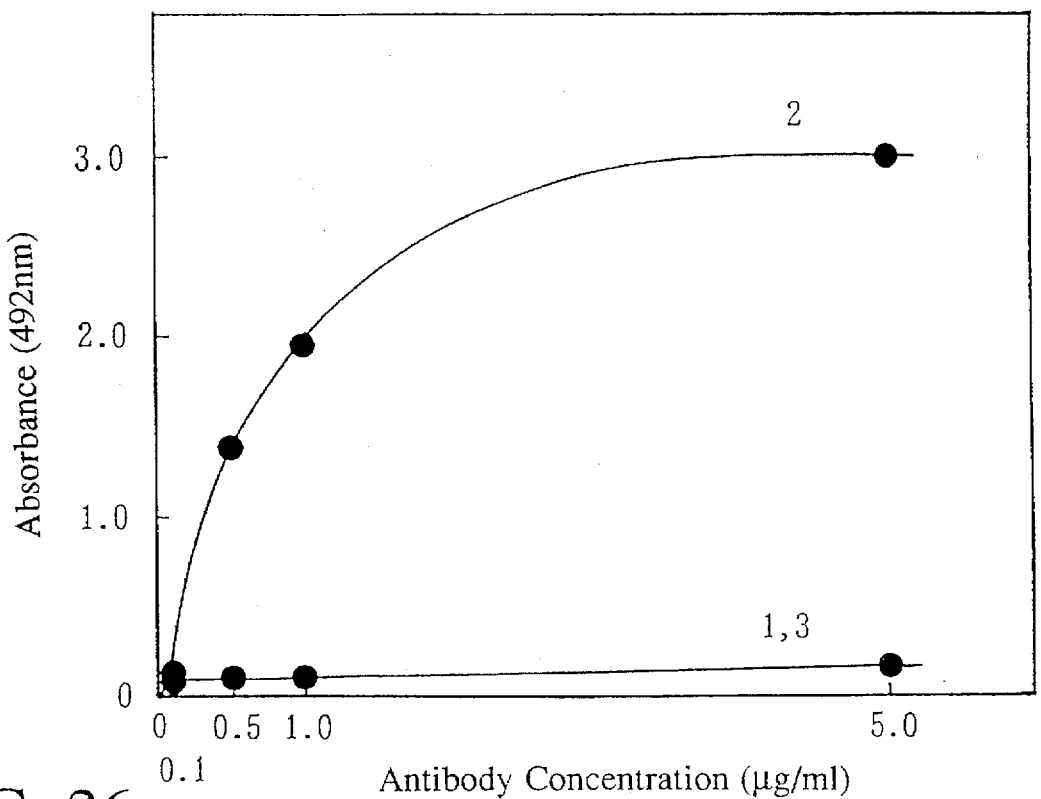
FIG. 26 shows the results of ELISA carried out to examine the reactivity of the monoclonal antibody to lipoprotein (a) obtained in Example 22 with the peptides represented by SEQ ID NO:8, SEQ ID NO:9 and SEQ ID NO:10 in the List of Sequences.

The results of these measurements are shown in FIG. 26. The data shown therein are those obtained by subtracting the absorbance of the control from the absorbance of each sample.

In FIG. 26, numerals 1, 2 and 3 represent the measured values (absorbances) for the antibody-producing immunogen obtained in Example 6, the antibody-producing immunogen obtained in Example 7, and the antibody-producing immunogen obtained in Example 8, respectively.

From these results, it has been confirmed that the monoclonal antibody to lipoprotein (a) obtained in Example 22 does not combine with the peptides represented by SEQ ID NO:8 and SEQ ID NO:10 in the List of Sequences which are peptides including the amino acid sequences represented by SEQ ID NO:1 and SEQ ID NO:3 in the List of Sequences, respectively, but specifically recognizes and combines with the peptide represented by SEQ ID NO:9 in the List of Sequences which is a peptide including the amino acid sequence represented by SEQ ID NO:2 in the List of Sequences.

EXAMPLE 23

Preparation of a mouse monoclonal antibody to apolipoprotein (a) specifically recognizing the amino acid sequence represented by SEQ ID NO:3 in the List of Sequences

[1] Immunization of an animal (1) The antibody-producing immunogen (having KLH as the carrier) obtained in Example 8 was dissolved in physiological saline (a 0.9% aqueous solution of sodium chloride) so as to give a concentration of 400 µg/ml. This solution was mixed with an equal amount of Freund's complete adjuvant to form an emulsion, and 0.5 ml of this emulsion was subcutaneously injected into the abdomen of a female BALB/c mouse (Charles River Japan Inc.) aged 8 weeks for purposes of immunization.

(2) Two weeks after the initial immunization, the above-described antibody-producing immunogen was dissolved in physiological saline so as to give a concentration of 200 µg/ml, this solution was mixed with an equal amount of Freund's incomplete adjuvant to form an emulsion, and 0.5 ml of this emulsion was injected as a booster.

This booster injection was repeated at intervals of 2 weeks.

(3) The antibody titer in the blood serum of this mouse, which was an immunized animal, was measured by an enzyme immunoassay (ELISA, EIA) at intervals of one week starting from 6 weeks after the initial immunization. This ELISA was carried out as follows: The antibody-producing immunogen (having BSA as the carrier) obtained in Example 8 was converted into a solid phase on a microplate, and blood serum obtained from the immunized animal was added thereto to effect reaction. After washing, peroxidase (POD)-labeled anti-mouse IgG antibody was added to the microplate to effect reaction. After washing, a color-producing solution containing hydrogen peroxide and 2,2'-azino-bis(3-ethylbenzthiazoline-6-sulfonic acid) (ABTS) was added to the microplate to develop color. Then, the antibody titer was determined by measuring the absorbance at 415 nm on an EIA plate reader (manufactured by Bio-Rad).

(4) After the lapse of 18 weeks from the initial immunization, it was noted that the antibody titer reached a plateau. Accordingly, the antibody-producing immunogen (having KLH as the carrier) obtained in Example 8 was dissolved in physiological saline so as to give a concentration of 800 µg/ml, and 0.5 ml of this solution was subcutaneously injected into the abdomen of this immunized mouse.

After 3 days, the spleen was excised from this immunized mouse.

[2] Growth of myeloma cells

The P3-X63-Ag8-U1 strain (Japanese Cancer Research Resources Bank 9085), which is a hypoxanthine-guanine phosphoribosyltransferase-deficient myeloma cell strain derived from a BALB/c mouse, was grown in RPMI1640 tissue culture medium (manufactured by Biocell) containing 10% fetal calf serum and supplemented with glutamine, penicillin and streptomycin.

More specifically, such myeloma cells were grown in a medium-sized bottle for cell culture (manufactured by Nunc; 200 ml capacity) until about 80% of the bottom surface of the bottle was occupied by the cells. The number of cells was counted with a hemocytometer according to the dye-exclusion technique using trypan blue.

[3] Cell fusion (1) The spleen obtained from the above-described immunized mouse was fully macerated by use of stainless steel mesh #200 and filtered while being washed with serum-free RPMI1640 liquid medium.

Thereafter, the resulting cell suspension was centrifuged at 200×g to separate spleen cells.

These spleen cells were further washed three times with serum-free RPMI1640 liquid medium.

(2) These spleen cells and the above-described grown P3-X63-Ag8-U1 strain myeloma cells were mixed in a ratio of 5:1 and centrifuged.

The mixed cells were slowly suspended in RPMI1640 liquid medium containing 50% polyethylene glycol 1500 (PEG 1500; manufactured by Boehringer Mannheim).

Then, this suspension was gradually diluted with RPMI1640 liquid medium so as to give a final polyethylene glycol concentration of 5%.

(3) The cells were separated therefrom by centrifugation and dispersed slowly in a growth medium comprising S-clone medium (manufactured by Sanko Junyaku Co., Ltd.) containing 5% hybridoma cloning factor (manufactured by Origen).

Each well of a 96-well flat-bottom micro titer plate (manufactured by Nunc) was inoculated with 100 1l of the suspension containing $10^6$ cells, and incubated at 37° C. in an atmosphere containing 5% carbon dioxide.

(4) One day after the cell fusion, 100 µl of HAT medium [the above-described growth medium supplemented with 0.01 mM hypoxanthine, 1.6 µM thymidine and 0.04 µM aminopterin (all manufactured by Tokyo Kasei Kogyo Co., Ltd.)] was added to each well.

For the succeeding 3 days, about a half of the HAT medium was replaced every day by fresh HAT medium. Thereafter, the same replacement was performed at intervals of 2 or 3 days.

(5) Cells were observed under the microscope.

Clones of hybridomas (fused cells) began to appear after 10 days or more. After 14 days or more, the supernatants obtained from the wells were screened by ELISA in order to test them for the production of an antibody recognizing the amino acid sequence represented by SEQ ID NO:3 in the List of Sequences. This ELISA was carried out in the same manner as in Reference Example 5.

(6) With respect to the wells giving a positive test for antibody production, the cells were spread over a 24-well plate and cultured. As the cell density became higher, the cells were cultured on larger scales using small-sized and medium-sized bottles.

(7) Hybridomas were cultured and maintained in HT medium (HAT medium containing neither aminopterin nor hybridoma cloning factor).

(8) The production of an antibody recognizing the amino acid sequence represented by SEQ ID NO:3 in the List of Sequences was tested by ELISA in the same manner as in Reference Example 5. As a result, there were detected four hybridomas productive of an antibody combining with the antibody-producing immunogen (having BSA as the carrier) obtained in Example 8, which is a peptide including the amino acid sequence represented by SEQ ID NO:3 in the List of Sequence, but not combining with BSA.

[4] Hybridoma subcloning (1) The above-described 4 hybridomas were subcloned according to the limiting dilution technique.

The number of cells of each hybridoma was counted with a hemocytometer according to the dye-exclusion technique using trypan blue.

Then, the cells of each hybridoma were suspended in HT medium at two cell densities of 0.5 and 1 viable cell per 100 µl of HT medium. Each of these suspensions was pipetted into the wells of a 96-well flat-bottom microplate in an amount of 100 µl per well.

These hybridomas were grown with the medium being replaced at intervals of 2 or 3 days.

(2) After 2 weeks, the number of colonies present in each well was counted under the microscope, and the wells productive of an antibody combining with the antibody-producing immunogen (having BSA as the carrier) obtained in Example 8, which is a peptide including the amino acid sequence represented by SEQ ID NO:3 in the List of Sequence, but not combining with BSA were detected by ELISA in the same manner as described above.

Thus, there were obtained four wells which each contained only one colony and were productive of an antibody as described above.

(3) These hybridomas were transferred to a 24-well plate and cultured for 2 weeks until a good growth of cells was achieved.

(4) Then, the reactivity with apolipoprotein (a) of the antibodies produced by these hybridomas was tested by the western blot technique.

This western blot technique was carried out in the same manner as in Reference Example 6, except that only one type of purified apolipoprotein (a) was subjected to electrophoresis in step (2) of Reference Example 6, and the supernatants of the hybridoma cultures were used in place of the polyclonal antibody to apolipoprotein (a) obtained in Examples 11.

As a result, one hybridoma was found to be a cell strain productive of an antibody to apolipoprotein (a) specifically recognizing the amino acid sequence represented by SEQ ID NO:3 in the List of Sequences.

(5) This hybridoma was cloned again in the same manner as described above in steps (1) and (2). By examining each well for antibody production, there were obtained a total of 15 hybridoma clones characterized in that only one hybridoma colony was present in a well and the hybridoma colony which produced an antibody combining with the antibody-producing immunogen (having BSA as the carrier) obtained in Example 8, which is a peptide including the amino acid sequence represented by SEQ ID NO:3 in the List of Sequences, but not combining with BSA.

(6) The reactivity with apolipoprotein (a) of the antibodies produced by these hybridoma clones was tested again by the western blot technique in the same manner as described above in step (4).

As a result, it has been confirmed that all of these hybridoma clones are cells productive of an antibody to apolipoprotein (a) which specifically recognizes the amino acid sequence represented by SEQ ID NO:3 in the List of Sequences.

(7) This cell strain was employed as a hydrodoma cell strain (161E2H6 strain) for producing a monoclonal antibody to apolipoprotein (a) which specifically recognizes a part or the whole of the amino acid sequence represented by SEQ ID NO:3 in the List of Sequences.

This hydrodoma cell strain (161E2H6 strain) was deposited on Aug. 4, 1993 with the National Institute of Bioscience and Human-Technology, the Agency of Industrial Science and Technology, the Ministry of International Trade and Industry, Japan, and assigned FERM BP-4378.

[5] Production of a monoclonal antibody (1) Using a medium-sized bottle (manufactured by Nunc), the resulting cell strain for producing a monoclonal antibody to apolipoprotein (a) was grown in HT medium until about 80% of its bottom surface was occupied by cells.

(2) Thereafter, these hybridoma cells were scraped out and collected by centrifugation at 200×g for 5 minutes.

Subsequently, they were washed three times with serum-free RPMI1640 liquid medium and then suspended in 2 ml of RPMI1640 liquid medium.

(3) 1 ml of the hybridoma cell suspension obtained in the above-described step (2) was injected into the abdominal cavity of a male BALB/c mouse (Charles River Japan Inc.) which had previously been treated with 2, 6, 10, 14-tetramethyl-pentadecane.

If no expansion of the abdomen of this mouse was observed within 2 weeks after the injection, the same procedure was repeated.

(4) As soon as an expansion of the abdomen of this mouse was observed, ascites was collected therefrom.

This ascites was centrifuged at 200×g for 5 minutes to separate the supernatant containing a monoclonal antibody to apolipoprotein (a) from the hybridoma cells.

[6] Purification of the monoclonal antibody (1) 1.8 g of sodium sulfate was added, with stirring, at 22° C. to 10 ml of the supernatant containing a monoclonal antibody to apolipoprotein (a). After sodium sulfate was completely dissolved, the stirring was continued for an additional hour to effect salting-out.

(2) This mixture was centrifuged at 22° C. (7000×g, 15 minutes), and the precipitate separated from the supernatant was dissolved in 2 ml of 40 mM sodium phosphate buffer (pH 8.0) containing 30 mM sodium chloride.

(3) Next, this solution was thoroughly dialyzed against 40 mM sodium phosphate buffer (pH 8.0) containing 30 mM sodium chloride, and then centrifuged at 1000×g for 20 minutes to remove any insoluble matter.

(4) This solution was passed at a flow rate of 0.4 ml/min. through a DEAE-cellulose ion exchange column (1×10 cm; manufactured by Serva) which had been equilibrated with 40 mM sodium phosphate buffer (pH 8.0) containing 30 mM sodium chloride, and the eluate was collected in 2 ml fractions.

(5) Absorbance measurement at 280 nm revealed that immunoglobulin G (IgG) was contained in the flow-through fractions of the eluate. Accordingly, the flow-through fractions were collected and concentrated to 2 ml.

(6) The resulting concentrate was further purified by protein A-Sepharose CL-4B affinity chromatography (manufactured by Pharmacia-LKB) to obtain a mouse monoclonal antibody to apolipoprotein (a) specifically recognizing the amino acid sequence represented by SEQ ID NO:3 in the List of Sequences.

The amount of the monoclonal antibody thus obtained was 10 mg as expressed in terms of protein.

According to the Ouchterlony immunodiffusion method using a commercially available specific anti-mouse immunoglobulin antiserum (manufactured by Dako), the class and subtype of the resulting monoclonal antibody to apolipoprotein (a) was determined to be $IgG_1$ and λ chain, respectively.

Reference Example 11

Reactivity of the monoclonal antibody to apolipoprotein (a) obtained in Example 23 with the peptides represented by SEQ ID NO:8, SEQ ID NO:9 and SEQ ID NO:10 in the List of Sequences The reactivity of the monoclonal antibody to apolipoprotein (a) obtained in Example 23 with the peptides represented by SEQ ID NO:8, SEQ ID NO:9 and SEQ ID NO:10 in the List of Sequences, which are peptides including the amino acid sequences represented by SEQ ID NO:1, SEQ ID NO:2 and SEQ ID NO:3 in the List of Sequences, respectively, was confirmed by ELISA.

Measurements were made in the same manner as in Reference Example 10, except that the monoclonal antibody to apolipoprotein (a) obtained in Example 23 was used in place of the monoclonal antibody to lipoprotein (a) obtained in Example 22, and four samples of this antibody had concentrations of 5.0 μg/ml, 10 μg/ml, 50 μg/ml and 100 μ/ml, respectively.

Figure 27:
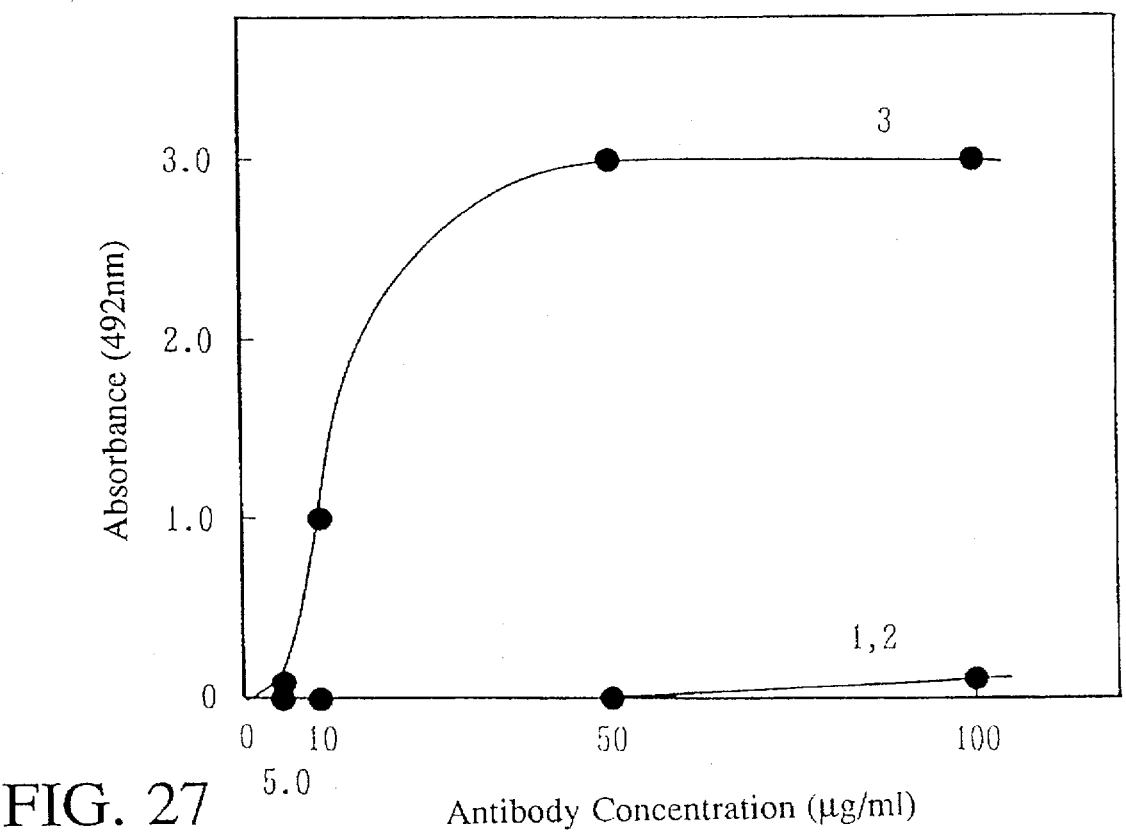
FIG. 27 shows the results of ELISA carried out to examine the reactivity of the monoclonal antibody to apolipoprotein (a) obtained in Example 23 with the peptides represented by SEQ ID NO:8, SEQ ID NO:9 and SEQ ID NO:10 in the List of Sequences.

The results of these measurements are shown in FIG. 27. The data shown therein are those obtained by subtracting the absorbance of the control from the absorbance of each sample.

In FIG. 27, numerals 1, 2 and 3 represent the measured values (absorbances) for the antibody-producing immunogen obtained in Example 6, the antibody-producing immunogen obtained in Example 7, and the antibody-producing immunogen obtained in Example 8, respectively.

From these results, it has been confirmed that the monoclonal antibody to lipoprotein (a) obtained in Example 23 does not combine with the peptides represented by SEQ ID NO:8 and SEQ ID NO:9 in the List of Sequences which are peptides including the amino acid sequences represented by SEQ ID NO:1 and SEQ ID NO:2 in the List of Sequences, respectively, but specifically recognizes and combines with the peptide represented by SEQ ID NO:10 in the List of Sequences which is a peptide including the amino acid sequence represented by SEQ ID NO:3 in the List of Sequences.

Reference Example 12
Reactivity with apolipoprotein (a) of the monoclonal antibody to apolipoprotein (a) obtained in Example 23

The reactivity with apolipoprotein (a) of the monoclonal antibody to apolipoprotein (a) obtained in Example 23 was confirmed by the western blot technique.

The western blot technique was carried out in the same manner as in Reference Example 6, except that five types of purified apolipoprotein (a) derived from human blood serum were subjected to electrophoresis, and the monoclonal antibody to apolipoprotein (a) obtained in Example 23 was used in place of the polyclonal antibody to apolipoprotein (a) obtained in Example 11.

Figure 28:
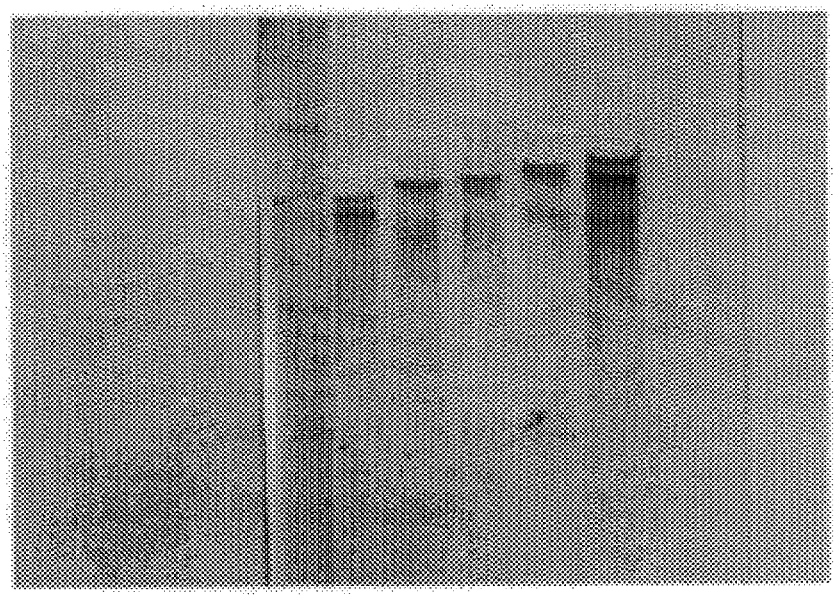
FIG. 28 is a photograph showing electrophoretic patterns observed in the western blot technique carried out to examine the reactivity of the monoclonal antibody to apolipoprotein (a) obtained in Example 23 with apolipoprotein (a).
Figure 29:
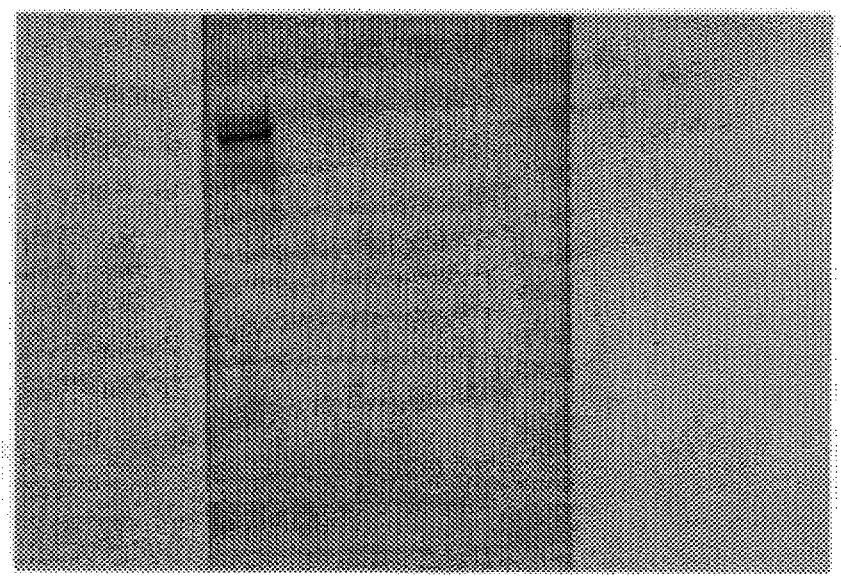
FIG. 29 is a photograph showing the electrophoretic patterns of negative controls observed in the western blot technique carried out to examine the reactivity of the monoclonal antibody to apolipoprotein (a) obtained in Example 23 with apolipoprotein (a).
Figure 30:
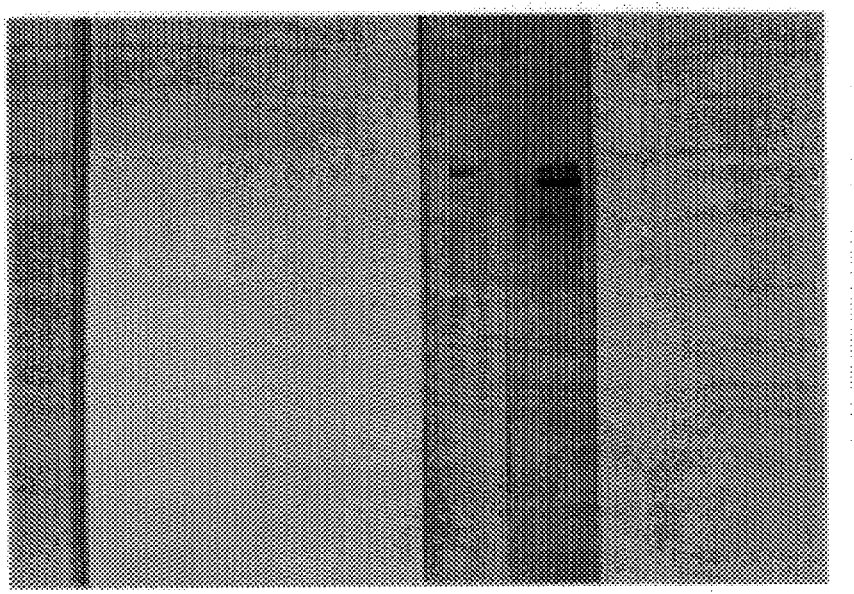
FIG. 30 is a photograph showing the electrophoretic pattern of a control observed in the western blot technique carried out to examine the reactivity of the monoclonal antibody to apolipoprotein (a) obtained in Example 23 with apolipoprotein (a).

The results of this western blot technique are shown in FIGS. 28, 29 and 30.

FIG. 28 shows the nitrocellulose membrane acted on by the monoclonal antibody to apolipoprotein (a) obtained in Example 23.

In FIG. 28, numerals 1 to 5 represent the respective electrophoretic patterns of the five types of purified apolipoprotein (a) derived from human blood serum, and B shows the position of the band of apolipoprotein B-100 useful as a reference standard for identifying the resulting electrophoretic bands.

On the basis of positional relationship with this band of apolipoprotein B-100 [G. Utermann et al., J. Clin. Invest., 80, 458–465(1987)], it can be seen that the bands observed in patterns 1 to 5 represent F, B, S1, S2, S3 and S4 isotypes of apolipoprotein (a).

FIG. 29 shows the negative control in which numerals 1 to 5 represent the respective electrophoretic patterns of the five types of purified apolipoprotein (a) derived from human blood serum. R represents, as a reference standard, the electrophoretic pattern of the purified apolipoprotein (a) derived blood serum as represented above by numeral 1.

FIG. 30 shows the control in which the nitrocellulose membrane was acted on by anti-lipoprotein (a) antibody reacting with apolipoprotein (a). The sample used was the purified apolipoprotein (a) derived from blood serum which corresponds to the above-described pattern 1. B shows the position of the band of apolipoprotein B-100 as a reference standard.

As can be seen from FIGS. 28 and 30, the monoclonal antibody to apolipoprotein (a) obtained in Example 23 exhibits color development at the same position as anti-lipoprotein (a) antibody reacting with apolipoprotein (a) does. Thus, it has been confirmed that this monoclonal antibody combines specifically with apolipoprotein (a).

Moreover, in FIG. 28, it has been confirmed that the monoclonal antibody to apolipoprotein (a) obtained in Example 23 react with various isotypes of apolipoprotein (a).

Furthermore, in FIG. 29, no color development is observed in the negative control which was not acted on by the monoclonal antibody to apolipoprotein (a) obtained in Example 23 or anti-lipoprotein (a) antibody reacting with apolipoprotein (a), indicating that nonspecific color development did not take place.

Reference Example 13
Reactivity with lipoprotein (a) of the monoclonal antibody to lipoprotein (a) obtained in Example 22 and the monoclonal antibody to apolipoprotein (a) obtained in

EXAMPLE 23

The reactivity with lipoprotein (a) of each of the monoclonal antibody to lipoprotein (a) obtained in Example 22 and the monoclonal antibody to apolipoprotein (a) obtained in Example 23 was confirmed by the western blot technique.

The western blot technique was carried out in the same manner as in Reference Example 7, except that each of the monoclonal antibody to lipoprotein (a) obtained in Example 22 and the monoclonal antibody to apolipoprotein (a) obtained in Example 23 was used in place of the polyclonal antibody to apolipoprotein (a) obtained in Example 11.

Figure 31:
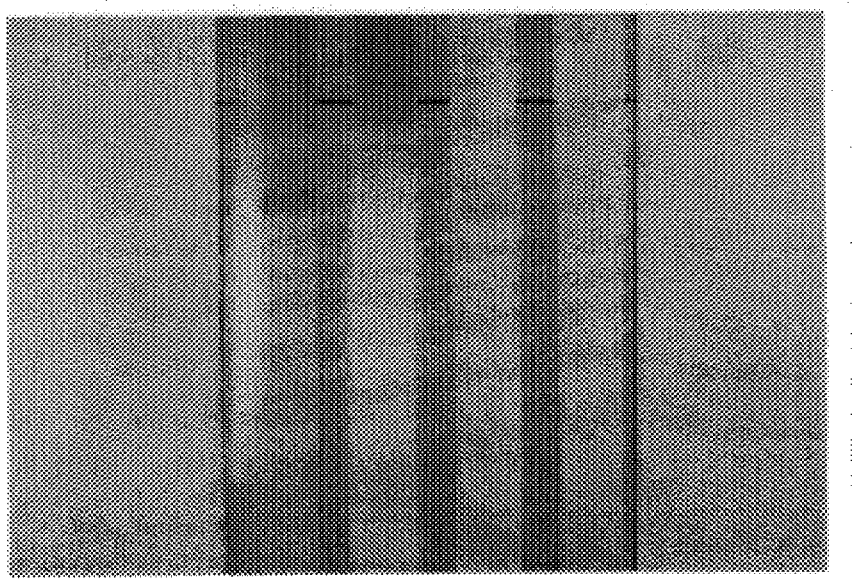
FIG. 31 is a photograph showing electrophoretic patterns observed in the western blot technique carried out to examine the reactivity with lipoprotein (a) of the monoclonal antibody to lipoprotein (a) obtained in Example 22 and the monoclonal antibody to apolipoprotein (a) obtained in Example 23.

The results of this western blot technique are shown in FIG. 31.

In FIG. 31, P represents the control, N represents the negative control, numeral 2 represents the nitrocellulose membrane acted on by the monoclonal antibody to lipoprotein (a) obtained in Example 22, and numeral 3 represents the nitrocellulose membrane acted on by the monoclonal antibody to apolipoprotein (a) obtained in Example 23.

As can seen by comparison with the control in FIG. 31, the monoclonal antibody to lipoprotein (a) obtained in Example 22 exhibits color development at the same position as the commercially available anti-lipoprotein (a) antibody does. Thus, it has been confirmed that this monoclonal antibody combines specifically with lipoprotein (a).

Moreover, the monoclonal antibody to apolipoprotein (a) obtained in Example 23 exhibits no color development at the position where the commercially available anti-lipoprotein (a) antibody exhibits color development. Thus, it has been confirmed that this monoclonal antibody does not combine with lipoprotein (a).

Furthermore, no color development is observed in the negative control which was not acted on by any of the antibody obtained in Example 22, the antibody obtained in Example 23, and the commercially available anti-lipoprotein (a) antibody, indicating that nonspecific color development did not take place.

Reference Example 14
Reactivity with LDL of the monoclonal antibody to lipoprotein (a) obtained in Example 22 and the monoclonal antibody to apolipoprotein (a) obtained in Example 23

The reactivity with LDL of each of the monoclonal antibody to lipoprotein (a) obtained in Example 22 and the monoclonal antibody to apolipoprotein (a) obtained in Example 23 was confirmed by the western blot technique.

(1) Human blood serum having a high LDL concentration was ultracentrifuged to separate a fraction having a specific gravity range of 1.006 to 1.063. Then, this serum fraction was subjected to affinity chromatography using anti-lipoprotein (a) antibody (manufactured by Immuno) as the ligand. The flow-through fractions were collected to obtain purified LDL.

(2) This LDL was dissolved in physiological saline (a 0.9% aqueous solution of sodium chloride) so as to give a concentration of 0.5 mg/ml. A 2 µl sample of this solution was subjected to electrophoresis using a Titan Gel Lipoprotein Electrophoresis Kit (manufactured by Helena Laboratory). The supporting medium was agarose gel. Using a barbital buffer (pH 8.8) as the electrophoresis buffer, a voltage of 90 V was applied for 75 minutes.

(3) Using a Nova Blot Electrophoretic Transfer Kit (manufactured by Pharmacia-LKB), transfer was carried out on a dry basis according to its instruction manual.

(4) The agarose gel obtained from step (2) was placed on a transfer apparatus and a 9 cm×9 cm nitrocellulose membrane (manufactured by Bio-Rad) was laid thereon. Using a transfer buffer comprising 48 mM Tris, 39 mM glycine, 0.0375% (W/V) sodium dodecyl sulfate (SDS) and 20% (V/V) methanol, transfer was carried out by passing an electric current of 65 mA for 2 hours.

(5) The nitrocellulose membrane having undergone the transfer was soaked overnight in 20 ml of phosphate-buffered physiological saline [5.59 mM disodium hydrogen phosphate, 1.47 mM potassium dihydrogen phosphate, 137 mM sodium chloride, 2.68 mM potassium chloride (pH 7.2)] containing 1% BSA at 4° C. to effect blocking.

(6) Then, this nitrocellulose membrane was washed by shaking it in 20 ml of a washing solution (phosphate-buffered physiological saline containing 0.05% Tween 20) for 10 minutes. This procedure was repeated three times.

(7) 80 µg each of the monoclonal antibody to lipoprotein (a) obtained in Example 22 and the monoclonal antibody to apolipoprotein (a) obtained in Example 23 was dissolved in 20 ml of phosphate-buffered physiological saline. Two nitrocellulose membranes as obtained from step (6) were separately soaked in these two solutions at room temperature for 2 hours to effect reaction.

(8) As a control, the procedure described above in step (7) was repeated by using goat anti-apolipoprotein B antibody to apolipoprotein B-100 being a component of LDL (manufactured by international Enzyme), dissolved at the same concentration, in place of the monoclonal antibody to lipoprotein (a) obtained in Example 22 and the monoclonal antibody to apolipoprotein (a) obtained in Example 23.

In addition, another nitrocellulose membrane as obtained from step (6), which was not acted on by any of the monoclonal antibody to lipoprotein (a) obtained in Example 22, the monoclonalantibody to apolipoprotein (a) obtained in Example 23, and goatantiapolipoprotein B antibody, was provided as a negative control.

(9) The nitrocellulose membranes subjected to the procedure described above in step (7) or (8) were washed by shaking them in 20 ml of the washing solution for 10 minutes. This procedure was repeated three times.

(10) Next, peroxidase-labeled anti-mouse IgG antibody (manufacture by Dako) and peroxidase-labeled anti-goat IgG antibody (manufactured by Dako) were diluted 500-fold with phosphate-buffered physiological saline containing 3% BSA to prepare 20 ml of a solution, and the nitrocellulose membranes were soaked therein at room temperature for 2 hours to effect reaction.

(11) These nitrocellulose membranes were washed by shaking them in 20 ml of the washing solution for 10 minutes. This procedure was repeated three times.

(12) The nitrocellulose membranes obtained from step (11) were soaked in 20 ml of phosphate-buffered physiological saline containing 0.025% 3,3'-diaminobenzidine tetrahydrochloride and 0.01% hydrogen peroxide at room temperature for 15 minutes to develop color.

Figure 32:
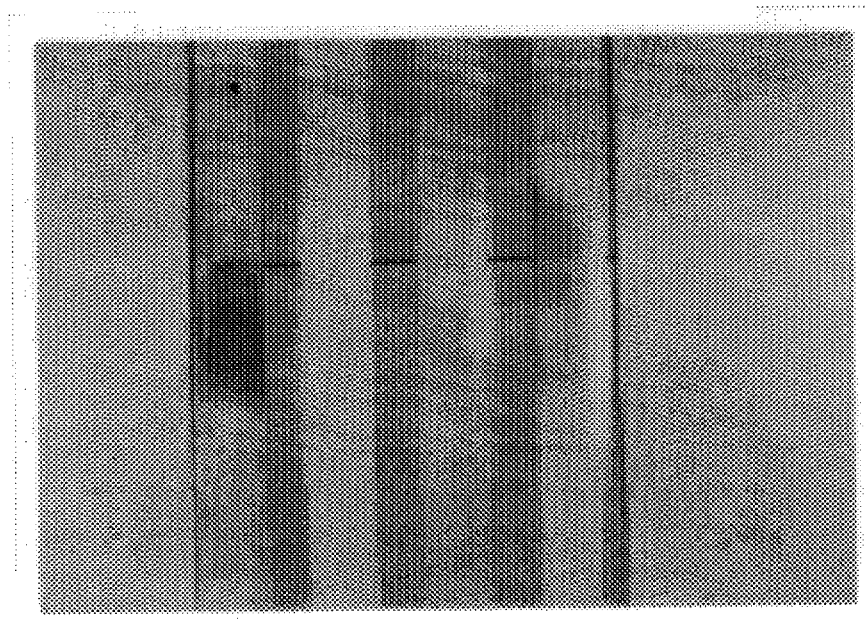
FIG. 32 is a photograph showing electrophoretic patterns observed in the western blot technique carried out to examine the reactivity with LDL of the monoclonal antibody to lipoprotein (a) obtained in Example 22 and the monoclonal antibody to apolipoprotein (a) obtained in Example 23.

The results of this western blot technique are shown in FIG. 32.

In FIG. 32, P represents the control, N represents the negative control, numeral 2 represents the nitrocellulose membrane acted on by the monoclonal antibody to lipoprotein (a) obtained in Example 22, and numeral 3 represents the nitrocellulose membrane acted on by the monoclonal antibody to apolipoprotein (a) obtained in Example 23.

As can seen by comparison with the control in FIG. 32, the monoclonal antibody to lipoprotein (a) obtained in Example 22 and the monoclonal antibody to apolipoprotein (a) obtained in Example 23 exhibit no color development at the position where the commercially available anti-apolipoprotein B antibody exhibits color development. Thus, it has been confirmed that these monoclonal antibodies do not combine with LDL.

Furthermore, no color development is observed in the negative control which was not acted on by any of the monoclonal antibody obtained in Example 22, the monoclonal antibody obtained in Example 23, and the commercially available anti-apolipoprotein B antibody, indicating that nonspecific color development did not take place.

Reference Example 15

Reactivity with plasminogen of the monoclonal antibody to lipoprotein (a) obtained in Example 22 and the monoclonal antibody to apolipoprotein (a) obtained in Example 23

The reactivity with plasminogen of each of the monoclonal antibody to lipoprotein (a) obtained in Example 22 and the monoclonal antibody to apolipoprotein (a) obtained in Example 23 was confirmed by the western blot technique.

The western blot technique was carried out in the same manner as in Reference Example 4, except that the monoclonal antibody to lipoprotein (a) obtained in Example 22 and the monoclonal antibody to apolipoprotein (a) obtained in Example 23 were used in place of the polyclonal antibodies to lipoprotein (a) obtained in Examples 9 and 10, respectively.

Figure 33:
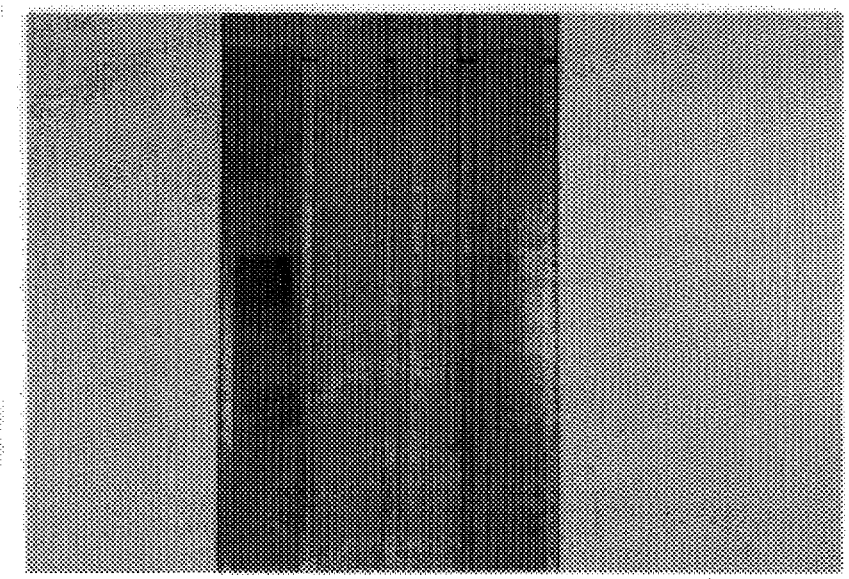
FIG. 33 is a photograph showing electrophoretic patterns observed in the western blot technique carried out to examine the reactivity with plasminogen of the monoclonal antibody to lipoprotein (a) obtained in Example 22 and the monoclonal antibody to apolipoprotein (a) obtained in Example 23.

The results of this western blot technique are shown in FIG. 33.

In FIG. 33, P represents the control, N represents the negative control, numeral 2 represents the nitrocellulose membrane acted on by the monoclonal antibody to lipoprotein (a) obtained in Example 22, and numeral 3 represents the nitrocellulose membrane acted on by the monoclonal antibody to apolipoprotein (a) obtained in Example 23.

As can seen from these results, the monoclonal antibody to lipoprotein (a) obtained in Example 22 and the monoclonal antibody to apolipoprotein (a) obtained in Example 23 exhibit no color development at the position where the commercially available anti-plasminogen antibody exhibits color development. Thus, it has been confirmed that these monoclonal antibodies do not combine with plasminogen.

Furthermore, no color development is observed in the negative control which was not acted on by the monoclonal antibody obtained in Example 22, the monoclonal antibody obtained in Example 23, or the like, indicating that nonspecific color development did not take place.

EXAMPLE 24
Method for the determination of lipoprotein (a) by ELISA

A system for the determination of lipoprotein (a) by ELISA was established using the monoclonal antibody to lipoprotein (a) obtained in Example 22.

Measurements were made in the same manner as in Example 17, except that the monoclonal antibody to lipoprotein (a) obtained in Example 22 was used at the same concentration in step (5) of Example 17, in place of the polyclonal antibody to lipoprotein (a) obtained in Example 9.

Figure 34:
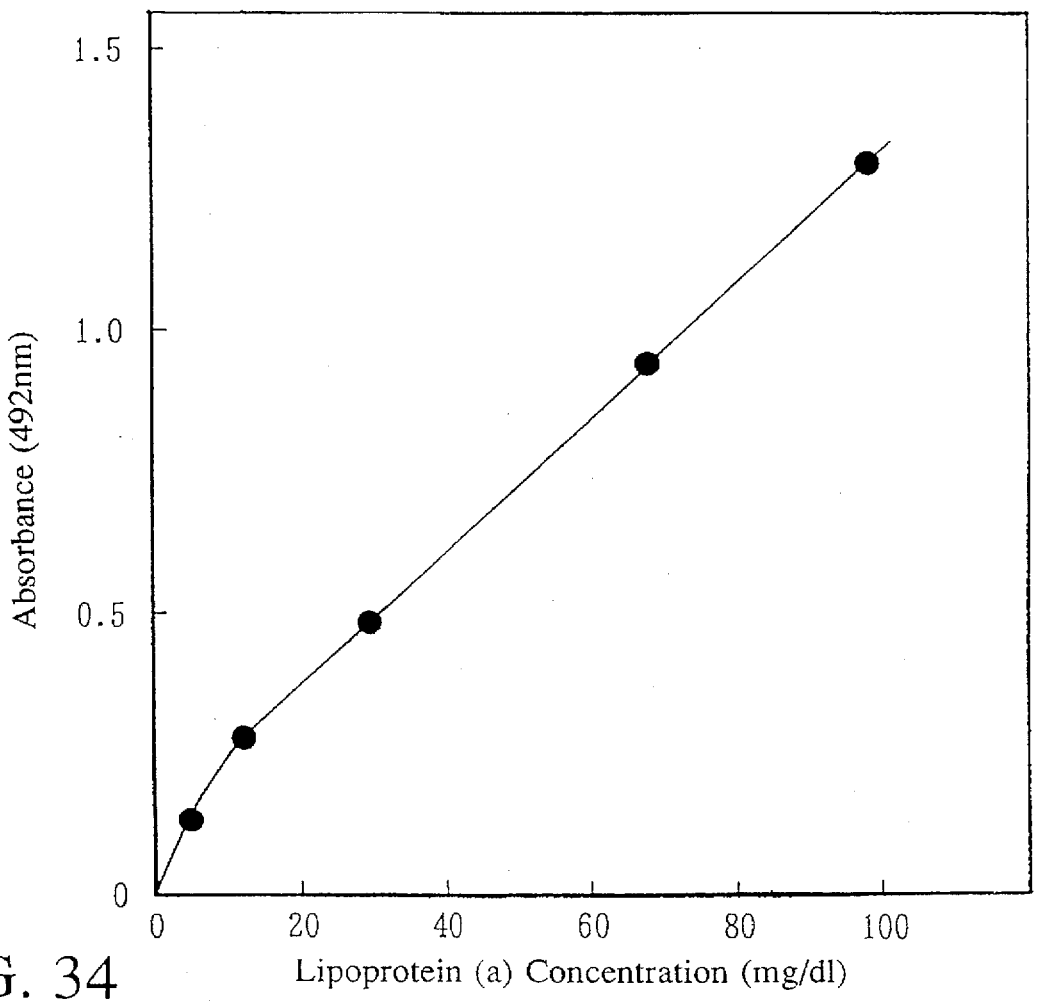
FIG. 34 is a graph showing a calibration curve for the determination of lipoprotein (a) by ELISA using the monoclonal antibody to lipoprotein (a) obtained in Example 22.

The calibration curve obtained by measuring five samples is shown in FIG. 34.

From these results, it has been confirmed that the method for the determination of lipoprotein (a) in accordance with the present invention enables quantitative determination of lipoprotein (a).

EXAMPLE 25
Comparison of the measured values for lipoprotein (a)

The measured values obtained by the present method for the determination of lipoprotein (a) by ELISA using the monoclonal antibody to lipoprotein (a) obtained in Example 22 were compared with those obtained by ELISA using the lipoprotein (a)-determining reagent of company A.

Samples 1 to 10 comprising ten types of blood sere were measured according to the present method for the determination of lipoprotein (a) by ELISA using the monoclonal antibody to lipoprotein (a) obtained in Example 22. The ELISA was carried out in the same manner as in Example 17.

The measurement of ten samples by using the lipoprotein (a)-determining reagent of company A was made according to its instruction manual.

The results of these measurements are summarized in Table 6.

TABLE 6

|  | Method of the invention | Reagent of company A |
|---|---|---|
| Sample 1 | 6.5 | 8.0 |
| Sample 2 | 2.2 | 3.7 |
| Sample 3 | 33.5 | 31.0 |
| Sample 4 | 12.5 | 10.9 |
| Sample 5 | 14.0 | 12.5 |
| Sample 6 | 18.0 | 17.5 |
| Sample 7 | 6.0 | 4.5 |
| Sample 8 | 57.5 | 54.5 |
| Sample 9 | 9.3 | 6.4 |
| Sample 10 | 75.0 | 72.9 |

(The values are expressed in mg/dl.)

From these results, it has been confirmed that the measured values for lipoprotein (a) obtained by the present method for the determination of lipoprotein (a) are substantially the same as those obtained by the method currently in use and, therefore, the method for the determination of lipoprotein (a) in accordance with the present invention can be practically used for purposes of clinical examination.

EXAMPLE 26
Method for the determination of apolipoprotein (a) by ELISA

A system for the determination of apolipoprotein (a) by ELISA was established using the monoclonal antibody to apolipoprotein (a) obtained in Example 23.

Measurements were made in the same manner as in Example 20, except that the monoclonal antibody to apolipoprotein (a) obtained in Example 23 was used in place of the polyclonal antibody to apolipoprotein (a) obtained in Example 11, and five samples having apolipoprotein (a) concentrations of 10 mg/dl, 20 mg/dl, 30 mg/dl, 40 mg/dl and 50 mg/dl was used.

Figure 35:
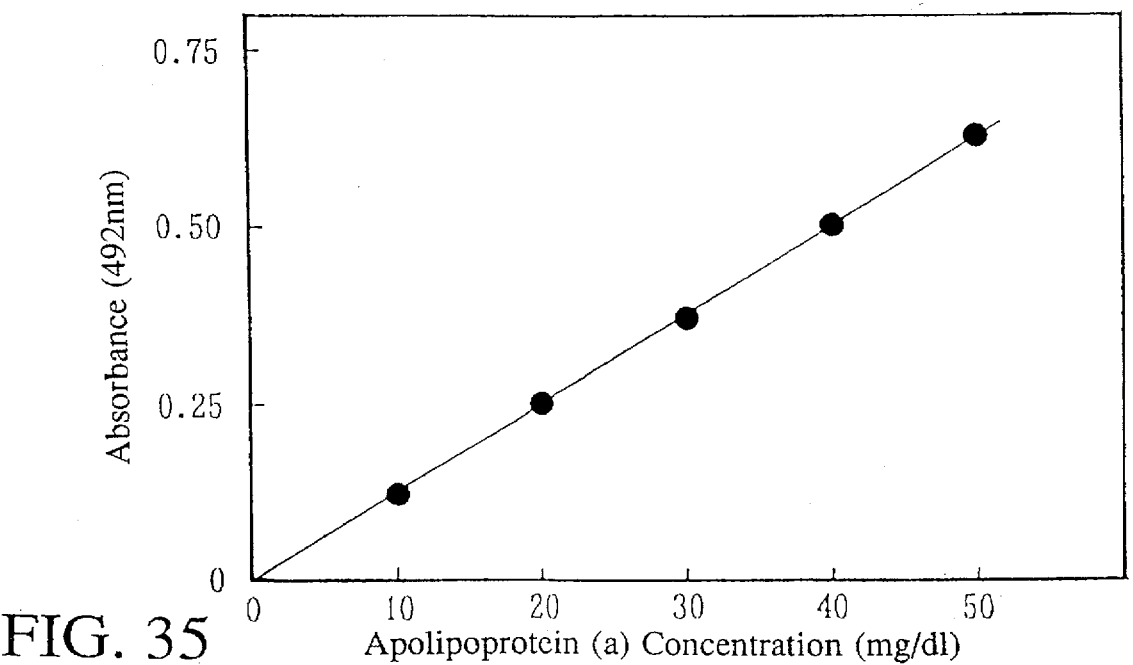
FIG. 35 is a graph showing a calibration curve for the determination of apolipoprotein (a) by ELISA using the monoclonal antibody to apolipoprotein (a) obtained in Example 23.
Figure 36:
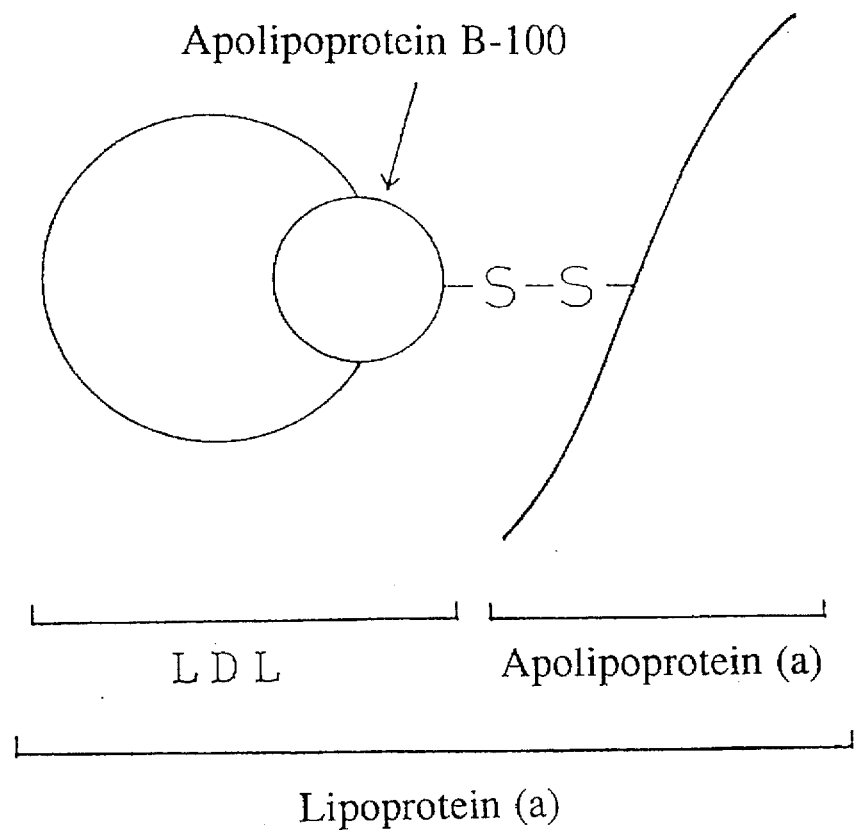
FIG. 36 is a schematic illustration of the structure of lipoprotein (a).

The calibration curve obtained by measuring the five samples is shown in FIG. 35.

From these results, it has been confirmed that the method for the determination of apolipoprotein (a) in accordance with the present invention enables quantitative determination of apolipoprotein (a).

EXAMPLE 27
Influence of serum samples on the method for the determination of apolipoprotein (a)

In the method for the determination of apolipoprotein (a) by ELISA using the monoclonal antibody to apolipoprotein (a) obtained in Example 23, it was confirmed by addition and recovery tests that the method was not influenced by serum samples.

(1) Three types of blood sera (A, B, C) were provided and the following samples were prepared using them as base materials.

(i) Three samples prepared by mixing 0.1 ml of physiological saline (a 0.9% aqueous solution of sodium chloride) with 0.9 ml of each of the three blood sera (A, B, C).

(ii) Three samples prepared by diluting the purified apolipoprotein (a) obtained in Example 20 with physiological saline so as to give a concentration of 100 mg/dl and mixing 0.1 ml of this solution with 0.9 ml of each of the three blood sera (A, B, C) to increase the apolipoprotein (a) concentrations of the three serum samples prepared in (i) by 10 mg/ml.

(iii) A sample prepared by diluting the purified apolipoprotein (a) obtained in Example 20 with physiological saline so as to give a concentration of 10 mg/dl.

(2) The absorbances of the above-described seven samples were measured according to the method for the determination of apolipoprotein (a) by ELISA as described in Example 26. The results thus obtained are shown in Table 7.

TABLE 7

|  | Serum A | Serum B | Serum C |
|---|---|---|---|
| (i) Absorbance of each sample comprising a blood serum mixed with physiological saline | 0.087 | 0.109 | 0.065 |
| (iii) Absorbance of 10 mg/dl of purified apolipoprotein (a) | 0.168 | 0.168 | 0.168 |
| (iv) Theoretical absorbance of each serum sample of (i) having an apolipoprotein (a) concentration increased by 10 mg/dl [(i) + (iii)] | 0.255 | 0.277 | 0.233 |
| (ii) Measured absorbance of each serum sample of (i) having an apolipoprotein (a) concentration increased by 10 mg/dl | 0.244 | 0.275 | 0.242 |
| (v) Percentage of the measured absorbance based on the theoretical value [(ii)/(iv)] | 95.7% | 99.3% | 104% |

It can be seen from these results that, when serum samples are measured according to the present method for the determination of apolipoprotein (a), measured values approximately equal to theoretical ones are obtained.

Thus, it has been confirmed that the method for the determination of apolipoprotein (a) in accordance with the present invention is a method capable of determining apolipoprotein (a) in serum samples accurately without undergoing the influence of nonspecific reactions or the like caused by the serum samples and, therefore, can be practically used for purposes of clinical examination.

Exploitability in Industry

The antibodies to lipoprotein (a) in accordance with the present invention are antibodies specifically recognizing lipoprotein (a) without showing a cross reaction with LDL or plasminogen. Accordingly, they do not require troublesome procedures such as ones for absorption treatment with LDL or plasminogen and for the selection of a cell strain productive of an antibody showing no cross reaction with LDL or plasminogen, and hence have the advantage that they can be obtained with less labor, time and cost than prior art antibodies to lipoprotein (a).

Moreover, the peptides selected from the amino acid sequence of lipoprotein (a) in accordance with the present invention and the immunogens for producing an antibody to lipoprotein (a) in accordance with the present invention are advantageous in that they do not require a troublesome and delicate procedure for purification from a biological sample and can be stored for a long period of time.

Furthermore, the method for the determination of lipoprotein (a) in accordance with the present invention is a method capable of determining the concentration of lipoprotein (a) accurately without measuring together LDL or plasminogen present in the samples.

Similarly, the antibodies to apolipoprotein (a) in accordance with the present invention are antibodies specifically recognizing apolipoprotein (a) without showing a cross reaction with lipoprotein (a) or plasminogen. Accordingly, they do not require troublesome procedures such as ones for absorption treatment with lipoprotein (a) or plasminogen and for the selection of a cell strain productive of an antibody showing no cross reaction with lipoprotein (a) or plasminogen, and hence have the advantage that they can be obtained with less labor, time and cost than prior art antibodies to apolipoprotein (a).

Moreover, the peptides selected from the amino acid sequence of apolipoprotein (a) in accordance with the present invention and the immunogens for producing an antibody to apolipoprotein (a) in accordance with the present invention are advantageous in that they do not require a troublesome and delicate procedure for purification from a biological sample and can be stored for a long period of time.

Furthermore, the method for the determination of apolipoprotein (a) in accordance with the present invention is a method capable of determining the concentration of apolipoprotein (a) accurately without measuring together lipoprotein (a) or plasminogen present in the samples.

We claim:

1. A peptide composed of 3 to about 50 amino acids and including 3 or more consecutive amino acids of an amino acid sequence selected from SEQ ID NO. 1 and SEQ ID NO. 2, which peptide has antigenicity as lipoprotein (a) and no antigenicity as low-density lipoprotein (LDL) or plasminogen.

2. The peptide according to claim 1, composed of 3 to about 50 amino acids and including 3 or more consecutive amino acids of the amino acid sequence represented by SEQ ID NO. 1.

3. The peptide according to claim 1, composed of 3 to about 50 amino acids and including 3 or more consecutive amino acids of the amino acid sequence represented by SEQ ID NO. 2.

4. A peptide having an amino acid sequence selected from the group consisting of SEQ ID NOS. 1, 2, 4, 5, 8 and 9, which peptide has antigenicity as lipoprotein (a) and no antigenicity as LDL or plasminogen.

5. An immunogen for producing an antibody, which comprises a peptide composed of 3 to about 50 amino acids and including 3 or more consecutive amino acids of an amino acid sequence selected from SEQ ID NO. 1 and SEQ ID NO. 2, which immunogen is useful to produce an antibody to lipoprotein (a) and has no antigenicity as LDL or plasminogen.

6. The immunogen for producing an antibody to lipoprotein (a) according to claim 5, which comprises a peptide composed of 3 to about 50 amino acids and including 3 or more consecutive amino acids of the amino acid sequence represented by SEQ ID NO. 1.

7. The immunogen according to claim 6, wherein the peptide is combined with a carrier.

8. The immunogen for producing an antibody to lipoprotein (a) according to claim 5, which comprises a peptide composed of 3 to about 50 amino acids and including 3 or more consecutive amino acids of the amino acid sequence represented by SEQ ID NO. 2.

9. The immunogen according to claim 8, wherein the peptide is combined with a carrier.

* * * * *

UNITED STATES PATENT AND TRADEMARK OFFICE
CERTIFICATE OF CORRECTION

PATENT NO. : 5,733,549

DATED : March 31, 1998

INVENTOR(S) : Shingo Yamada, Keiichi Inoue, Megumi Kitajima, Hajime Yoshimura and Ikunosuke Sakurabayashi It is certified that error appears in the above-identified patent and that said Letters Patent is hereby corrected as shown below:

Title page, item, should read--

[75]   Inventors:   Shingo Yamada; Keiichi Inoue;
Megumi Kitajim<u>a</u>; Hajime Yoshimura,
all of Sagamihara; Ikunosuke
Sakurabayashi, Omiya, all of Japan --

Signed and Sealed this

Twenty-second Day of September, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:1:

Ser Asp Ala Glu Gly Thr Ala Val
1               5

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:2:

Glu Ala Pro Ser Glu Gln Ala Pro Thr Glu Gln Arg
1               5                   10

( 2 ) INFORMATION FOR SEQ ID NO:3:

( i ) SEQUENCE CHARACTERISTICS:

(A) LENGTH: 9 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:3:

Arg Asn Pro Asp Ala Val Ala Ala Pro
1               5

(2) INFORMATION FOR SEQ ID NO:4:

(i) SEQUENCE CHARACTERISTICS:
(A) LENGTH: 6 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:4:

Asp Ala Glu Gly Thr Ala
1               5

(2) INFORMATION FOR SEQ ID NO:5:

(i) SEQUENCE CHARACTERISTICS:
(A) LENGTH: 7 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:5:

Gln Ala Pro Thr Glu Gln Arg
1               5

(2) INFORMATION FOR SEQ ID NO:6:

(i) SEQUENCE CHARACTERISTICS:
(A) LENGTH: 5 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:6:

Ala Val Ala Ala Pro
1               5

(2) INFORMATION FOR SEQ ID NO:7:

(i) SEQUENCE CHARACTERISTICS:
(A) LENGTH: 120 amino acids
(B) TYPE: amino acid
(C) STRANDEDNESS: single
(D) TOPOLOGY: unknown (ii) MOLECULE TYPE: protein (xi) SEQUENCE DESCRIPTION: SEQ ID NO:7:

Glu Gln Ala Pro Thr Glu Gln Arg Pro Gly Val Gln Glu Cys Tyr His
1               5                   10                  15
Gly Asn Gly Gln Ser Tyr Arg Gly Thr Tyr Ser Thr Thr Val Thr Gly
                20                  25                  30
Arg Thr Cys Gln Ala Trp Ser Ser Met Thr Pro His Ser His Ser Arg

```
                         35                        40                              45

Thr  Pro  Glu  Tyr  Tyr  Pro  Asn  Ala  Gly  Leu  Ile  Met  Asn  Tyr  Cys  Arg
           50                      55                     60

Asn  Pro  Asp  Ala  Val  Ala  Ala  Pro  Tyr  Cys  Tyr  Thr  Arg  Asp  Pro  Gly
 65                       70                     75                          80

Val  Arg  Trp  Glu  Tyr  Cys  Asn  Leu  Thr  Gln  Cys  Ser  Asp  Ala  Glu  Gly
                     85                     90                               95

Thr  Ala  Val  Ala  Pro  Pro  Thr  Val  Thr  Pro  Val  Pro  Ser  Leu  Glu  Ala
                100                     105                          110

Pro  Ser  Glu  Gln  Ala  Pro  Thr  Glu
            115                      120
```

(2) INFORMATION FOR SEQ ID NO:8:

(i) SEQUENCE CHARACTERISTICS:
    (A) LENGTH: 9 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:8:

```
 Cys  Ser  Asp  Ala  Glu  Gly  Thr  Ala  Val
 1                    5
```

(2) INFORMATION FOR SEQ ID NO:9:

(i) SEQUENCE CHARACTERISTICS:
    (A) LENGTH: 13 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:9:

```
 Cys  Glu  Ala  Pro  Ser  Glu  Gln  Ala  Pro  Thr  Glu  Gln  Arg
 1                    5                           10
```

(2) INFORMATION FOR SEQ ID NO:10:

(i) SEQUENCE CHARACTERISTICS:
    (A) LENGTH: 10 amino acids
    (B) TYPE: amino acid
    (C) STRANDEDNESS: single
    (D) TOPOLOGY: unknown (ii) MOLECULE TYPE: peptide (xi) SEQUENCE DESCRIPTION: SEQ ID NO:10:

```
 Cys  Arg  Asn  Pro  Asp  Ala  Val  Ala  Ala  Pro
 1                    5                       10
```